US 7,056,882 B2

(12) United States Patent
Kuberasampath et al.

(10) Patent No.: US 7,056,882 B2
(45) Date of Patent: *Jun. 6, 2006

(54) TREATMENT TO PREVENT LOSS OF AND/OR INCREASE BONE MASS IN METABOLIC BONE DISEASES

(75) Inventors: Thangavel Kuberasampath, Medway, MA (US); Charles M. Cohen, Weston, MA (US); Herrmann Oppermann, Medway, MA (US); Engin Ozkaynak, Milford, MA (US); David C. Rueger, Hopkinton, MA (US); John E. Smart, Weston, MA (US); Roy H. L. Pang, Etna, NH (US)

(73) Assignee: Curis, Inc., Cambridge, MA (US)

( * ) Notice: Subject to any disclaimer, the term of this patent is extended or adjusted under 35 U.S.C. 154(b) by 66 days.

This patent is subject to a terminal disclaimer.

(21) Appl. No.: 09/952,318

(22) Filed: Sep. 13, 2001

(65) Prior Publication Data

US 2003/0224979 A1 Dec. 4, 2003

Related U.S. Application Data

(63) Continuation of application No. 09/170,936, filed on Oct. 13, 1998, now Pat. No. 6,333,312, which is a continuation of application No. 08/432,883, filed on May 2, 1995, now abandoned, which is a continuation of application No. 08/115,914, filed on Sep. 1, 1993, now abandoned, which is a continuation of application No. 07/923,780, filed on Jul. 31, 1992, now abandoned, which is a continuation-in-part of application No. 07/752,857, filed on Aug. 30, 1991, now abandoned, which is a continuation-in-part of application No. 07/667,274, filed on Mar. 11, 1991, now abandoned.

(51) Int. Cl.
*A61K 38/18* (2006.01)
*A61K 38/16* (2006.01)

(52) U.S. Cl. .............................. 514/2; 514/12; 424/85.1
(58) Field of Classification Search .................... 514/2, 514/12; 424/85.1
See application file for complete search history.

(56) References Cited

U.S. PATENT DOCUMENTS

| 4,863,732 A | | 9/1989 | Nathan et al. | |
|---|---|---|---|---|
| 4,877,864 A | | 10/1989 | Wang et al. | |
| 4,925,833 A | | 5/1990 | McNamara et al. | |
| 4,968,590 A | | 11/1990 | Kuberasampath et al. | |
| 4,975,526 A | | 12/1990 | Kuberasampath et al. | |
| 5,011,691 A | * | 4/1991 | Oppermann et al. | 424/423 |
| 5,091,513 A | | 2/1992 | Huston et al. | |
| 5,106,626 A | | 4/1992 | Parsons et al. | |
| 5,106,748 A | | 4/1992 | Wozney et al. | |
| 5,108,753 A | * | 4/1992 | Kuberasampath et al. | 424/422 |
| 5,108,922 A | | 4/1992 | Wang et al. | |
| 5,116,738 A | | 5/1992 | Wang et al. | |
| 5,118,667 A | | 6/1992 | Adams et al. | |
| 5,141,905 A | | 8/1992 | Rosen et al. | |
| 5,154,931 A | | 10/1992 | Kruger et al. | |
| 5,187,076 A | | 2/1993 | Wozney et al. | |
| 5,208,219 A | | 5/1993 | Ogawa et al. | |
| 5,344,654 A | * | 9/1994 | Rueger et al. | 424/423 |
| 5,354,557 A | * | 10/1994 | Oppermann et al. | 424/423 |
| 5,393,739 A | | 2/1995 | Bentz et al. | |
| 5,453,419 A | | 9/1995 | Murakami et al. | |
| 5,496,552 A | * | 3/1996 | Kuberasampath et al. | 424/420 |
| 5,645,591 A | * | 7/1997 | Kuberasampath et al. | 424/423 |
| 5,674,844 A | * | 10/1997 | Kuberasampath et al. | 514/12 |
| 5,739,107 A | * | 4/1998 | Cohen et al. | 514/12 |
| 5,814,604 A | * | 9/1998 | Oppermann et al. | 514/12 |

(Continued)

FOREIGN PATENT DOCUMENTS

| CA | 2020660 | 8/1990 |
|---|---|---|
| EP | 0128041 | 12/1984 |
| EP | 0148155 | 1/1985 |
| EP | 0416578 | 9/1990 |
| EP | 0436469 | 7/1991 |
| EP | 0512844 | 11/1992 |
| EP | 0514130 | 11/1992 |
| EP | 0514720 | 11/1992 |
| WO | WO 88/00205 | 1/1988 |
| WO | WO 89/09605 | 10/1989 |
| WO | WO 89/09787 | 10/1989 |
| WO | WO 89/09788 | 10/1989 |
| WO | WO 89/10409 | 11/1989 |
| WO | WO 90/01321 | 2/1990 |
| WO | WO 90/03733 | 4/1990 |
| WO | WO 91/05802 | 5/1991 |
| WO | WO 92/00382 | 1/1992 |
| WO | WO 9200432 | 1/1992 |
| WO | WO 92/02199 | 4/1992 |
| WO | WO 92/09697 | 6/1992 |
| WO | WO 92/13565 | 8/1992 |
| WO | WO 92/14481 | 9/1992 |
| WO | WO 92/15323 | 9/1992 |
| WO | WO 92/19262 | 11/1992 |
| WO | WO 92/20371 | 11/1992 |
| WO | WO 92/21355 | 12/1992 |
| WO | WO 92/21365 | 12/1992 |
| WO | WO 92/00432 | 1/1993 |
| WO | WO 93/00050 | 1/1993 |
| WO | WO 94/03600 | 2/1994 |

OTHER PUBLICATIONS

Ngo et al., 1994, The Protein Folding Problem and Tertiary Structure Prediction, Birkhauer, Boston, pp. 491–495.*
Wells, 1990, Biochemistry 29:8509–8517.*

(Continued)

*Primary Examiner*—Elizabeth Kemmerer
(74) *Attorney, Agent, or Firm*—Fish & Neave IP Group Ropes & Gray, LLP

(57) ABSTRACT

The invention is a treatment for increasing the bone mass or preventing bone loss in an individual afflicted with a bone disease which includes administering to the individual a morphogen in a therapeutically effective amount so as to maintain or stimulate bone formation.

40 Claims, 12 Drawing Sheets

U.S. PATENT DOCUMENTS

| | | | | | |
|---|---|---|---|---|---|
| 5,840,325 | A | * | 11/1998 | Kuberasampath et al. | 424/420 |
| 5,958,441 | A | * | 9/1999 | Oppermann et al. | 424/423 |
| 6,013,856 | A | * | 1/2000 | Tucker et al. | 623/16.11 |
| 6,027,743 | A | * | 2/2000 | Khouri et al. | 424/423 |
| 6,110,482 | A | * | 8/2000 | Khouri et al. | 424/423 |
| 6,281,195 | B1 | * | 8/2001 | Rueger et al. | 514/21 |
| 6,333,312 | B1 | * | 12/2001 | Kuberasampath et al. | 514/12 |
| 6,504,079 | B1 | * | 1/2003 | Tucker et al. | 623/16.11 |
| 6,586,388 | B1 | * | 7/2003 | Oppermann et al. | 514/2 |

OTHER PUBLICATIONS

Kimmel, "Quantitative Histologic Changes in the Proximal Tibial Growth Cartilage of Aged Female Rats", Cells and Materials Supplement 1, 11–18 (1991).

Luyten et al: Purification and Partial amino acid sequence of osteogenin, a protein initiating bone differentiation. J. Biol. Chem. 264:13377–13380 (1989).

Wozney et al., "Regulation of Chondrogenesis and Osteogenesis By The BMP Proteins", Journ. of Cellular Biochemistry, Supplemental 16F, Abstract 026 (1992).

Basler et al., "Control of Cell Pattern in the Neural Tube: Regulation of Cell Differentiation by dorsalin–1, a Novel TGF.beta. Family Member", (1993), 73 Cell, 687–702.

Behringer et al., "Abnormal sexual development in transgenic mice chronically expressing Mullerian inhibiting substance", Nature, 345:167–170 (1990).

Caplan Arnold I., "Mesenchymal Stern Cells", J. Orthop Res. 9:641–650 (1991).

Cate et al., "Isolation of the Bovine and Human Genes for Mullerian Inhibiting Substance and Expression of the Human Gene in Animal Cells", Cell, 45:685–698 (1986).

Celeste et al., "Molecular Cloning of BMP–8: A Protein Present In Bovine Bone Which Is Highly Related To The BMP–5/6/7 Subfamily Of Osteoinductive Molecules", Journ. of Cellular Biochemistry, Supplement 16F, Abstract 502 (1992).

Celeste et al. "Identification of transforming growth factor —beta. superfamily members present in bone–inductive protein purified from bovine bone", Proc. Natl. Acad. Sci. 87:9843–9847 (1990).

Celeste et al., "Highly Purified Bovine Bone–Inductive Activity Contains Multiple Protein Species Related to BMP–2", 54:105, Journal of Cellular Biochemistry, (1990).

Chen et al., "Bone Morphogentic Protein–2b Stimulation of Growth and Osteogenic Phenotypes in Rat Osteoblast–like Cells: Comparsion with TGF–.beta..sub.1 ", J. Bone and Min, Res., 6:1893 (1991).

Chomcyzaski et al., "Single–Step Method of RNA Isolation by Acid Guanidinium Thiocyanate–phenol–Chloroform Extraction", Anal Biochem., 162:156–159 (1987).

D'Alessandro et al., "Purification, Characterization and Activity of Recombinant Human BMP–5", 166:Q105 Journal of Cellular Biochemistry.

Dayoff Margaret O., "A Model of Evolutionary Change in Proteins", Atlas of Protein Sequence and Structure 5:345–352, Suppl. 3 (1978).

Erben et al., "Histomorphometric Analysis of the Rat Proximal Tibal Metaphysis by Linear Scanning", Scanning Microscopy, 4: (1990).

Green et al., "Graded changes in dose of a Xenopus activin A homologue elicit stepwise transitions in embryonic cell fate", Nature 347:391–394 (1990).

Ibbotson et al., "Contrasting Effects of Parathyroid Hormone and Insulin–like Growth Factor I in an Aged Ovariectomized Rat Model of Postmenopausal Osteoporsis", J. Bone and Min. Res., 7:425–432 (1992).

Ibbotson et al., "Contrasting Effects of Parathyroid Hormone and Insulin–like Growth Factor I in an Aged Ovariectomized Rat Model of Postmenopausal Osteoporosis", J. Bone and Min. Res., 7:425–432 (1992).

Israel et al., "Expression and Characterization of Bone Morphogenetic Protein–2 in Chinese Hamster Ovary Cells", Growth Factors. vol. 7, 139–150 (1992).

Israel et al., "Expression of Recombinant BMP2 in Chinese Hamster Ovary Cells", Journal of Cellular Biochemistry, 168:Q111.

Jee, Webster S.S., "The Aged Rat Model for Bone Biology Studies: Foreword," Cells and Materials Supplement, 1: 1–2 (1991).

Katagiri et al., "The Non–Osteogenic Mouse Pluripotent Cell Line, C3H10T1/2, Is Inducted To Differentiate into Osteoblastic Cells By Recombinant Human Bone Morphogentic Protein–2," Biochemical and Biophysical Research Communications, 172:295–299 (1990).

Lee, "Identification of a Novel Member (GF–1) of the Transforming Growth Factor–.beta. Superfamily", Molecular Endocrinology, 90:1034–1040 (1990).

Lee, "Expression of growtn/differentiation factor 1 in the nervous system: Conservation of a bicistronic structure", PNAS. 88:4250–4254 (1991).

Li et al., "Age–Related Changes of Cancellous and Cortical Bone Histomorphometry in Female Sprague–Dawley Rats," Cell and Materials Supplement 1.25–35 (1991).

Lyons et al., "Patterns of expression of murine Vgr–1 and BMP–2a RNA suggest that transfroming growth factor–.beta.–like genes coordinatley regulate aspects of embryonic development", Genes & Development, 3:1657–1668 (1989).

Lyons et al., "Vgr–1. a mammalian gene related to Xenopus Vg–1, is a member of the transforming growth factor .beta. gene superfamily", PNAS, 86:4554–4558 (1989).

Malluche et al., "Renal bone disease 1990: An unmet challenge for the nephrologist" Kidney Intern., 38:193–211 (1990).

Mankin, "Rickets, Osteomalacia, and Renal Osteodystrophy", The Orthopedic Clinics of North America, 21:81–96 (1990).

Marks et al, "Bone Cell Biology: The Regulation of Development, Structure, and Function in the Skeleton," The American Journal of Anatomy, 183:1–44 (1988).

Martin et al., "Relationships Between Marrow Fat and Bone Turnover in Ovariectomized and Intact Rats", Bone, 123–131 (1991).

Mason et al., "Activin B: Precursor Sequences, Genomic Structure and in Vitro Activities", Mol. Endocrinology, 3;1352–1358 (1989).

Mason et al., "Complementary DNA sequences of ovarian follicular fluid inhibin show precursor structure and homology with transfroming growth factor–.beta.", Nature, 318:659–663 (1985).

Miller et al., "Phenotypic modulation of the Swarm Rat Chondrosarcoma induced by Morphogenetic Bone Matrix", Cancer Research, 42:2589–3594 (1987).

Moseklide et al., "The Anabolic Effects of Human Parathyroid Hormone (hPTH) on Rat Vertebral Body Mass Are also Reflected in the Quality of Bone, Assessed by Biomechanical Testing: A Comparsion Study Between hPTH–(1–34) and hPTH–(1–84)," Endocrinology, 129:(1) 421–428.

Okaynak et al. "Murine Osteogenic Protein–1 (OP–1), High levels of mRNA in Kidney" Biochem.Biophys. Res. Commun. 179:116–123 (1991).

Ozkaynak et al., "Regulation of OP–1 mRNA expression in vivo; structures of OP–3, a new member of the TGF–.beta. superfamily", J. Bone. Min. Res. Supplement 1, Abst. 1040 (1993).

Ozkaynak et al., "Osteogenic protein–2: A New Member of the Transforming Growth Factor–.beta. Superfamily Expressed in Early Embryogenesis", J. Biol. Chem. 267:25220–25227 (1992).

Ozkaynak et al., "Op–1 cDNA encodes an osteogenic protein in the TGF–.beta. family", EMBO J 9:2085–2093 (1990).

Padgett et al., "A transcript from a Drosophila pattern gene predicts a protein homologous to the transforming growth factor–.beta. family", Nature. 325:81–84 (1987).

Padgett et al., "Human BMP sequences can confer normal dorsal–ventral patterning in the Drosophila embryo", Proc. Natl. Acad. Sci. USA, vol. 90, 2905–2909 (1993).

Panganiaban et al., "Biochemical Characterication of the Drosophila dpp Protein, a Member of the Transforming Growth Factor .beta. Family of Growth Factors", Mol and Cell. Biol. 10:2669–2677 (1990).

Partiff et al., "Bone Remodeling and Bone Loss: Understanding The Pathophysiology of Osteoporsis," Clinical Obstetrics and Gynecology, 30: (4) 789–811.

Perides et al., "Regulation of Neural Cell Adhesion Molecule and L1 by the Transforming Growth Factor–.beta. Superfamily", J. of Biological Chemistry, 269:765–770 (1994).

Puchacz, E. et al., "Chroosomal Localization of the Human Osteocalcin Gene", Endocrinology, vol. 124, 2648–2650.

Raisz et al., "Pathogenesis, prevention, and Treatment of Osteoporosis," Ann. Rev. Med.. 40:251–67 (1989).

Raisz, "Hormonal Regulation of Bone Growth and Remodeling," Ciba Foundation Symposium 136, 226–238 (1988).

Reddi et al., "Biochemical sequences in the transformation of normal fibroblasts in adolescent rats", Proc. Natl. Acad. Sci. 69:1601–1605 (1972).

Ritz et al., "Genesis of Bone Disease in Uremia", Bone and Mineral Research, %:309–374.

Rogers et al., "Bone Morphogenetic proteins–2 and –4 are involved In The ACid–Induced Differentiation of Embryonal Carcinoma Cells", Mol. Biol. of the Cell, vol. 3:189, 189–496 (1992).

Rosen et al., "Development Expression of Cartilage and E–Specific Genes in the Rat Embryo", Calcified Tissue, A35:136 (1988).

Rosen et al., "Purification and Molecular Cloning of a Novel Group of BMPS and Localization of BMP MRNA in Developing Bone", Connective Tissue Research, 20:313–319 (1989).

Rosen et al., "In Vivo and In Vitro Roles of BMP in Skeletal Formation and Repair", 33:004, Journal of Cellular Biochemistry (1990).

Rosen et al., "Isolation and Characterization of BMP–Responsive Cartilage and Bone Cell Progenitors From Mouse Embryo Limb Buds", Journ. of Cellular Biochemistry, Supplement 16F, Abstract 513 (1992).

Rosenberg, "The Pathology of Metabolic Bone Disease", Radiologic Clinics of North America. 29:19–35 (1991).

Sampath et al., "Drosophila transforming growth factor .beta. superfamily proteins induce endochondral bone fromation in mammals", Proc. Natl. Acad. Sci. 90:6004–6008 (1993).

Sampath et al., "Recombinant Human Ostegenic Protein–1 (hOP–1) induces New Bone Fromation in Vivo With A Specific Activity Comparable with Natural Bovine Osteogenic Protein and Stimulates Osteoblast Proliferation and Differentiation in Vitro," J. Biol. Chem., 267:20352–20362 (1992).

Sampath et al., "Dissociative extraction and reconstituion of extracellular matrix components involved in local bone differentiation", Proc. Natl. Acad. Sci. 78:7599–7602 (1981).

Sampath et al., "Bovine Osteogine Protein Is Composed of Dimers of OP–1 and BMP–2A, Two Members of the Transforming Growth Factor–.beta. Superfamily", J. Biol. Chem. 265:13198–13205 (1990).

Sampath et al., "Insolation of osteogin, an extracellular matrix–associated bone inductive protein by heparin affinity chromatography", proc. Natl. Acad. Sci. 84:7109–7113 (1987).

Sampath et al., "Homology of bone–inductive proteins from human, monkey, bovine, and rat exttacellullar matrix", Proc. Natl. Acad. Sci. 80:6591–6595 (1983).

Schapira et al., "The Rat as a Model for Studies of the Aging Skelton", Suppl. 1, Cells and Materials. 181–188 (1991).

Schubert et al., "Activin is a nerve cell survival molecule", Nature. 344:868–870 (1990).

Schultz et al., "Neovascular Growth Factors", Eye, 5:170–180 (1991).

Smith et al., "Identification of a potent Xenopus medoderm–inducing factor as a homologue of activin A", Nature, 34,5:729–731 (1990).

Sokol et al., "Mouse Macrophage Factor Induces Head Structures and Organizes a Body Axis in Xenopus", Science. 249:261–563 (1990).

Storm et al., "Limb alterations in brachypodism mice due to mutations in a new member of the TGF.beta.–superfamily", 368 Nature. 639–643 (1994).

Tabas et al., "Bone Morphogenetic Protein: Chromosomal Localization of Human Genes for BMP1, BMP2A, and BMP3", Genomics, vol. 9, 283–289 (1991).

Takano–Yamamoto et al., "Direct effects of 17.beta.–estrasdiol on trabecular bone in ovariectomized rats", Proc. Natl. Acad. Sci. USA. 2172–2176 (1990).

Takuwa et al., "Bone Morphogenetic Protein–2 Stimulates alkaline Phosphate Activity and Collagen Synthesis In Cultured Cells, MC3T3–E1," Biochemical and Biophysical Research Communication, 174:96–101 (1991).

Thies et al., "Recombinant Human Bone Morphogenetic Protein–2 induces Osteoblastic Differentiation in W–20–17 Stromal Cells", Endocrinology, vol. 130:1, 1318–1324 (1992).

Tzamaloulas, Antonios H., "Diagnosis and Management of Bone Disorders in Chronic Renal Failure and Dialyzed Patients", Medical Clinics of North America. 74:961–974.

Urist, MR, "Bone; Formation by Autoinduction", Science 150:893–399 (1965).

Vukicevic et al., "Localization of Osteogenic Protein–1 (Bone Morphogentic Protein–7) During Human Embryonic Development High Affinity Binding To Basement Membranes", Biochemical and Biophysical Research Communications, 198:693–700 (1994).

Vukicevic et al., "Osteogenin Inhibits Proliferation and timulates Differentiation In Mouse Osteoblast–Like Cells (MC3T3–E1)", Biochem. Biophys. Res. Comm., 166:750–756 (1990).

Vukicevic et al., "Stimualtion of the expression of osteogenic and chondrogenic phenotypes in vitro by osteogin", PNAS, 86:8793–8797 (1989).

Wang et al., "Purification and Characterization of Cartilage and Bone Inducing Factors", Calcified Tissue, A37:146 (1988).

Wang et al., "Purification and characterization of other distinct bone–inducing prroteins" Proc. Natl. Acad. Sci. USA, 85:9488 (1988).

Wang et al., "Recombinant human bone morphogenetic protein induces bone formation", PNAS, 87:2220–2224 (1990).

Weeks et al., "A Maternal mRNA Localized to the Vegetal Hernisphere in Xenopus Eggs Codes for a Growth Factor Related to TGF–.beta.", Cell. 51:861–867 (1987).

Wharton et al., "Drosophila 60A gene, another transforming growth factor .beta. family member, is closely related to human bone morphogenetic proteins", PNAS, 88:9214–9218 (1991).

Wong et al., "Target cells in bone for parathormone and calcitonin are different: Enrichment for each cell type by sequential digestion of mouse calvaria and selective adhesion to polymeric surfaces", PNAS. 72:3167–3171 (1975).

Wozney et al., "Identification Through Molecular Cloning of Factors involved in In Vivo Cartilage Formation", Calcified Tissue, A37:147 (1988).

Wozney et al., "Growth Factors Influencing Bone Development," J. ell Sci. Suppl., 13:149–156 (1990).

Wozney, John M., "The Bone Morphogenetic Protein Family and Osteogenesis", Molecular Reproducing and Development, 160–167 (1992).

Wozney et al., "Novel Regulators of Bone Formation: Molecular Clones and Activities", Science, 242:1528–1534 (1988).

Wozney, John M., "Bone Morphogenetic Proteins," Progress in Growth Factor Research, 1:267–280 (1989).

Wronski et al., "The Ovariectomized Rat as an Animal Model For Postmenopausal Bone Loss," Cells and Materials Supplement 1, 69–74 (1991).

Wronski et al., "Time Course of Vertebral Osteopenia in Ovariectomized Rats", Bone, 10:295–301.

Wronski et al., "Effect of Body Weight of Osteopenia in Ovariectomized Rats", Calif Tissue Int. 40:155–159 (1987).

Yamaguchi et al., "Recombinant Human Morphogenetic Protein–2 Stimulates Osteoblastic Maturation and Inhibits Myogeneic Diffemtiation In Vitro", J. Cell. Biol., 113:681–687 (1991).

Yannas, Angew, "Biologically Active Analogues of the Extracellular Matrix: Artifical Skin and Nerves", Chem. Int. Ed. Engl., 29:20–35 (1990).

Sampath et al., "Recombinant Human Osteogenic Protein (hOP–1) Induces New Bone Formation With A Specific Activity Comparable To That Of Natural Bovine OP", Orthopaedic Research Society, 72 (1992).

Cook et al., "Healing of large Segmental Defects Using Recombinant Human Osteogenic Protein (RHOP–1)", Orthopaedic Research Society, 581 (1992).

Ozkaynak et al., "Organ Specific Expression of Selected TGF–.beta. Superfamily Members", J. Cell Biochem, Suppl 0:81 W114 (1992).

Maliakal et al., "1,25 Dihydroxyvitamin D3, Modulate The Effect Of Human Osteogenic Protein–1 (hOP–1) On Osteoblasts in Culture", Bone and Mineral Research, 7:S211 475 (1992).

Asahina et al., "Human Osteogenic Protein–1 (hOP–1) Induces Chondroblastic Differentiation of Osteoprogenitor Cells Derived From Newborn Rat Calvaria", Bone and Mineral Research. 7:S205 452 (1992).

Knutsen et al, "Evidence That Osteogenic Protein–1 (OP–1) May Modulate its Effects On Human Bone Cell Proliferation (HBC) By Regulating The Local Production Of Insulin–Like Growth Factors", Bone and Mineral Research, 7:S104 47 (1992).

Rutherford et al., "Use of Bovine Osteogenic Protein to Promote Rapid Osseointegration of Endosseous Dental Implants", Int'l Journal of Oral & Maxillofacial Implants, 7:297–301 (1992).

Lefer et al., "Anti–ischaemic and Endothelial Protective Actions of Recombinant Human Osteogenic Protein (hOP–1)", J. Mol. Cell Cardiol. 24:585–593 (1992).

Kimmel, "Quantitative Histologic Changes in the Proximal Tibial Growth Cartilage of Aged Female Rats", Cells and Materials Supplement 1, 11–18 (1991).

Luyten et al: Purification and Partial amino acid sequence of osteogin, a protein initiating bone differentiation. J. Biol. Chem. 264:13377–13380 (1989).

Wozney et al., "Regulation of Chondrogenesis and Osteogensis By The BMP Proteins", Journ. of Cellular Biochemistry, Supplemental 16F, Abstract 026 (1992).

* cited by examiner

| PROTEIN CONCENTRATION (ng/ml) | | cAMP (PICOMOLE/WELL) | |
| --- | --- | --- | --- |
| | | -PTH | +PTH |
| BACKGROUND | | 1.30 | 2.20 |
| OP-1 | 1.0 | 1.25 | 3.45 |
| | 10.0 | 1.30 | 3.80 |
| | 40.0 | 1.25 | 4.45 |
| TGF-β | 0.1 | 0.95 | 1.42 |
| | 1.0 | 0.83 | 1.25 |
| | 5.0 | 0.68 | 0.88 |

Fig. 3

TREATMENT TO PREVENT LOSS OF AND/OR INCREASE BONE MASS IN METABOLIC BONE DISEASES

RELATION TO RELATED APPLICATIONS

This application is a continuation of U.S. Ser. No. 09/170,936 filed Oct. 13, 1998, now U.S. Pat. No. 6,333,312, which is a continuation of U.S. Ser. No. 08/432,883, filed May 2, 1995, now abandoned, which is a continuation of U.S. Ser. No. 08/115,914 filed Sep. 1, 1993, now abandoned, which is a continuation of Ser. No. 07/923,780, filed Jul. 31, 1992, now abandoned, which is a continuation-in-part of U.S. Ser No. 07/752,857, filed Aug. 30, 1991, now abandoned, which is a continuation-in-part of U.S. Ser. No. 07/667,274, filed Mar. 11, 1991, now abandoned.

This invention relates to means for increasing the bone mass and/or preventing the loss of bone mass in a mammal.

BACKGROUND OF THE INVENTION

Throughout adult life, bone is continually undergoing remodeling through the interactive cycles of bone formation and resorption (bone turnover). Bone resorption typically is rapid, and is mediated by osteoclasts (bone resorbing cells), formed by mononuclear phagocytic precursor cells at bone remodeling sites. This process then is followed by the appearance of osteoblasts (bone forming cells) which form bone slowly to replace the lost bone. The activities of the various cell types that participate in the remodeling process are controlled by interacting systemic (e.g., hormones, lymphokines, growth factors, vitamins) and local factors (e.g., cytokines, adhesion molecules, lymphokines and growth factors). The fact that completion of this process normally leads to balanced replacement and renewal of bone indicates that the molecular signals and events that influence bone remodeling are tightly controlled.

A number of bone growth disorders are known which cause an imbalance in the bone remodeling cycle. Chief among these are metabolic bone diseases, such as osteoporosis, osteoplasia (osteomalacia), chronic renal failure and hyperparathyroidism, which result in abnormal or excessive loss of bone mass (osteopenia). Other bone diseases, such as Paget's disease, also cause excessive loss of bone mass at localized sites.

Osteoporosis is a structural deterioration of the skeleton caused by loss of bone mass resulting from an imbalance in bone formation, bone resorption, or both, such that the resorption dominates the bone formation phase, thereby reducing the weight-bearing capacity of the affected bone. In a healthy adult, the rate at which bone is formed and resorbed is tightly coordinated so as to maintain the renewal of skeletal bone. However, in osteoporotic individuals an imbalance in these bone remodeling cycles develops which results in both loss of bone mass and in formation of microarchitectural defects in the continuity of the skeleton. These skeletal defects, created by perturbation in the remodeling sequence, accumulate and finally reach a point at which the structural integrity of the skeleton is severely compromised and bone fracture is likely. Although this imbalance occurs gradually in most individuals as they age ("senile osteoporosis"), it is much more severe and occurs at a rapid rate in postmenopausal women. In addition, osteoporosis also may result from nutritional and endocrine imbalances, hereditary disorders and a number of malignant transformations.

Patients suffering from chronic renal (kidney) failure almost universally suffer loss of skeletal bone mass (renal osteodystrophy). While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Osteoplasia, also known as osteomalacia ("soft bones"), is a defect in bone mineralization (e.g., incomplete mineralization), and classically is related to vitamin D deficiency (1,25-dihydroxy vitamin $D_3$). The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) is known to cause malabsorption of calcium, leading to abnormal bone loss. In children, hyperparathyroidism can inhibit growth, in adults the skeleton integrity is compromised and fracture of the ribs and vertebrae are characteristic. The parathyroid hormone imbalance typically may result from thyroid adenomas or gland hyperplasia, or may result from prolonged pharmacological use of a steroid. Secondary hyperparathyroidism also may result from renal osteodystrophy. In the early stages of the disease osteoclasts are stimulated to resorb bone in response to the excess hormone present. As the disease progresses, the trabecular bone ultimately is resorbed and marrow is replaced with fibrosis, macrophages and areas of hemorrhage as a consequence of microfractures. This condition is referred to clinically as osteitis fibrosa.

Paget's disease (osteitis deformans) is a disorder currently thought to have a viral etiology and is characterized by excessive bone resorption at localized sites which flare and heal but which ultimately are chronic and progressive, and may lead to malignant transformation. The disease typically affects adults over the age of 25.

To date, osteopenia treatments are based on inhibiting further bone resorption, e.g., by 1) inhibiting the differentiation of hemopoietic mononuclear cells into mature osteoclasts, 2) by directly preventing osteoclast-mediated bone resorption, or 3) by affecting the hormonal control of bone resorption. Drug regimens used for the treatment of osteoporosis include calcium supplements, estrogen, calcitonin and diphosphonates. Vitamin $D_3$ and its metabolites, known to enhance calcium and phosphate absorption, also are being tried. None of the current therapies stimulate regeneration of new bone tissue. In addition, all of these agents have only a transient effect on bone remodeling. Thus, while in some cases the progression of the disease may be halted or slowed, patients with significant bone deterioration remain actively at risk. This is particularly prevalent in disorders such as osteoporosis where early diagnosis is difficult and/or rare and significant structural deterioration of the bone already may have occurred.

It is an object of the present invention to develop methods and compositions for inhibiting or preventing the loss of bone mass and/or for increasing bone formation in an individual who, for example, is afflicted with a disease which decreases skeletal bone mass, particularly where the disease causes an imbalance in bone remodeling. Another object is to enhance bone growth in children suffering from bone disorders, including metabolic bone diseases. Still another object is to prevent or inhibit bone deterioration in individuals at risk for loss of bone mass, including postmenopausal women, aged individuals, and patients undergoing dialysis. Yet another object is to provide methods and compositions for repairing defects in the microstructure of structurally compromised bone, including repairing bone fractures. Thus, the invention is aimed at stimulating bone formation and increasing bone mass, optionally over prolonged periods of time, and particularly to decrease the occurrence of new fractures resulting from structural deterioration of the skeleton. These and other objects and features of the invention will be apparent from the description, drawings, and claims which follow.

SUMMARY OF THE INVENTION

The present invention provides methods and compositions for inhibiting loss of bone mass, and/or for stimulating bone formation in mammals, particularly humans.

In one aspect, the invention features a therapeutic treatment method and composition for preventing loss of bone mass and/or for increasing bone mass in a mammal which includes administering to the individual a therapeutically effective morphogen in an amount and for a time sufficient to inhibit the loss of bone mass, and/or to increase bone mass in the individual.

In another aspect, the invention features a therapeutic treatment method and composition for preventing loss of bone mass and/or for increasing bone mass in a mammal which includes administering to the mammal a compound that stimulates in vivo a therapeutically effective concentration of an endogenous morphogen in the body of the mammal sufficient to prevent loss of and/or to increase bone mass in the individual. These compounds are referred to herein as morphogen-stimulating agents, and are understood to include substances which, when administered to a mammal, act on tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

The morphogens described herein are believed to play a significant role in maintaining appropriate bone mass in an individual. Thus, a morphogen may be administered according to the invention to any individual who requires assistance in maintaining appropriate bone mass and/or who suffers from a bone remodeling imbalance. For example, the morphogen or morphogen-stimulating agent may be administered according to the invention to an adult suffering from renal failure to prevent bone deterioration which is associated with that disease, e.g., to correct bone loss due to late stage kidney failure. Similarly, the administration of a morphogen to a child suffering from renal failure is expected not only to alleviate loss of bone mass in the child, but also to stimulate bone formation and thus growth. In addition, administration of a morphogen or morphogen-stimulating agent to an individual suffering from defects in skeletal microstructure is expected to result in repair of that defect, and to enhance the weight-bearing capacity of the treated bone.

Accordingly, in another aspect of the invention, the treatment methods and compositions of the invention may be used to treat a bone fracture or any disease which causes or results in bone fractures or other defects in skeletal microstructure, including loss of bone mass, and which compromise the weight-bearing capacity of bone. Such diseases include, for example, chronic renal failure and other kidney diseases, particularly those requiring dialysis; osteomalacia; vitamin D deficiency-induced osteopenia or osteoporosis; postmenopausal or senile osteoporosis; hyperparathyroidism and Paget's disease.

In still another aspect, the invention provides methods and compositions for protecting an individual at risk for the loss or deterioration of skeletal bone mass by prophylactic administration of a morphogen or morphogen-stimulating agent. Individuals at risk include postmenopausal females, aged individuals, and individuals undergoing dialysis, particularly prolonged or chronic dialysis.

In one preferred embodiment of the invention, the morphogen or morphogen-stimulating agent is administered systemically to the individual, e.g., orally or parenterally. In another embodiment of the invention, the morphogen may be provided directly to the bone, e.g., by injection to the bone periosteum or endosteum. Direct injection is particularly useful for repairing defects in the microstructure of the bone, including bone fractures.

In any treatment method of the invention, "administration of morphogen" refers to the administration of the morphogen, either alone or in combination with other molecules. For example, the mature form of the morphogen may be provided in association with its precursor "pro" domain, which is known to enhance the solubility of the protein. Other useful molecules known to enhance protein solubility include casein and other milk components, as well as various serum proteins. Additional useful molecules which may be associated with the morphogen or morphogen-stimulating agent include tissue targeting molecules capable of directing the morphogen or morphogen-stimulating agent to bone. Tissue targeting molecules envisioned to be useful in the treatment protocols of this invention include tetracycline, diphosphonates, and antibodies or other binding proteins which interact specifically with surface molecules on bone tissue cells.

Still another useful tissue targeting molecule is the morphogen precursor "pro" domain, particularly that of OP-1, BMP2 or BMP4. These proteins are found naturally associated with bone tissue but likely are synthesized in other tissues and targeted to bone tissue after secretion from the synthesizing tissue. For example, the primary source of OP-1 synthesis appears to be the tissue of the urinary tract (e.g., renal tissue), while the protein has been shown to be active in bone tissue (see below.) Moreover, the protein has been identified in serum, saliva and various milk forms. In addition, the secreted form of the protein comprises the mature dimer in association with the pro domain of the intact morphogen sequence. Accordingly, the associated morphogen pro domains may act to target specific morphogens to different tissues in vivo.

Associated tissue targeting or solubility-enhancing molecules also may be covalently linked to the morphogen using standard chemical means, including acid-labile linkages, which likely will be preferentially cleaved in the acidic environment of bone remodeling sites.

The morphogens or morphogen-stimulating agents also may be administered together with other "co-factors" known to have a beneficial effect on bone remodeling, including parathyroid hormone, vitamin $D_3$, prostaglandins, dexamethasone, IGF (I, II) and their binding proteins, and other agents known to enhance osteoblast activity. Other useful confactors include calcitonin and estrogen and other agents which inhibit bone resorption.

Among the morphogens useful in this invention are proteins originally identified as osteogenic proteins, such as the OP-1, OP-2 and CBMP2 proteins, as well as amino acid sequence-related proteins such as DPP (from Drosophila), Vg1 (from Xenopus), Vgr-1 (from mouse, see U.S. Pat. No. 5,011,691 to Oppermann et al.), GDF-1 (from mouse, see Lee (1991) *PNAS* 88:4250–4254), all of which are presented in Table II and Seq. ID Nos.5–14), and the recently identified 60A protein (from Drosophila, Seq. ID No. 24, see Wharton et al. (1991) *PNAS* 88:9214–9218.) The members of this family, which include members of the TGF-b super-family of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences of the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins are defined essentially by residues 18–263 (hOP2) and residues 18–260 (mOP2). (Another cleavage site also occurs 21 residues further upstream for both OP-2 proteins.) |
| "CBMP2" | refers generically to the morphogenically active proteins expressed from a DNA sequence encoding the CBMP2 proteins, including allelic and species variants |

TABLE I-continued

| | |
|---|---|
| | thereof, e.g., human CBMP2A ("CBMP2A (fx)", Seq ID No. 9) or human CBMP2B DNA ("CBMP2B (fx)", Seq. ID No. 10). The amino acid sequence for the full length proteins, referred to in the literature collectively as BMP2A and BMP2B, or BMP2 and BMP4, appear in Wozney, et al. (1988) Science 242: 1528–1534. The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408. |
| "DPP (fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81–84. The pro domain likely extends from the signal peptide cleavage site to residue 456; the mature protein likely is defined by residues 457–588. |
| "Vg1 (fx)" | refers to protein sequences encoded by the Xenopus Vg1 gene and defining the conserved seven cysteine skeleton (Seq. ID No. 12). The amino acid sequence for the full length protein appears in Weeks (1987) Cell 51: 861–867. The pro domain likely extends from the signal peptide cleavage site to residue 246; the mature protein likely is defined by residues 247–360. |
| "Vgr-1 (fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554–4558. The pro domain likely extends from the signal peptide cleavage site to residue 299; the mature protein likely is defined by residues 300–438. |
| "GDF-1 (fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The pro domain likely extends from the signal peptide clavage site to residue 214; the mature protein likely is defined by residues 215–372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A (fx)" refers to the protein sequences defining the conserved seven cysteine skeleton (residues 354 to 455 of Seq. ID No. 24.) The pro domain likely extends from the signal peptide cleavage site to residue 324; the mature protein likely is defined by residues 325–455. |
| "BMP3 (fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528–1534. The pro domain likely extends from the signal peptide cleavage site to residue 290; the mature protein likely is defined by residues 291–472. |

TABLE I-continued

"BMP5 (fx)"  refers to protein sequences encoded by the human BMP5 gene and defining the conserved seven cysteine skeleton (Seq. ID No. 27). The amino acid sequence for the full length protein appears in Celeste, et al. (1991) PNAS 87: 9843–9847. The pro domain likely extends from the signal peptide cleavage site to residue 316; the mature protein likely is defined by residues 317–454.

"BMP6 (fx)"  refers to protein sequences encoded by the human BMP6 gene and defining the conserved seven cysteine skeleton (Seq. ID No. 28). The amino acid sequence for the full length protein appear sin Celeste, et al. (1990) PNAS 87: 9843–5847. The pro domain likely includes extends from the signal peptide cleavage site to residue 374; the mature sequence likely includes residues 375–513.

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it also is anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, a-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2).

In another preferred aspect, these sequences further comprise the following additional sequence at their N-terminus:

```
Cys Xaa Xaa Xaa Xaa        (Seq. ID No. 15)
 1           5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

Generic Sequence 3

```
Leu Tyr Val Xaa Phe
 1           5

Xaa Xaa Xaa Gly Trp Xaa Xaa Trp Xaa
             10

Xaa Ala Pro Xaa Gly Xaa Xaa Ala
 15              20

Xaa Tyr Cys Xaa Gly Xaa Cys Xaa
     25              30

Xaa Pro Xaa Xaa Xaa Xaa Xaa
             35

Xaa Xaa Xaa Asn His Ala Xaa Xaa
     40              45

Xaa Xaa Leu Xaa Xaa Xaa Xaa Xaa
             50

Xaa Xaa Xaa Xaa Xaa Xaa Xaa Cys
     55              60

Cys Xaa Pro Xaa Xaa Xaa Xaa Xaa
             65

Xaa Xaa Xaa Leu Xaa Xaa Xaa
 70              75

Xaa Xaa Xaa Xaa Val Xaa Leu Xaa
             80

Xaa Xaa Xaa Xaa Met Xaa Val Xaa
 85              90

Xaa Cys Gly Cys Xaa
         95
``` wherein each Xaa is independently selected from a group of one or more specified amino acids defined as follows: "Res."

means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4

```
Cys Xaa Xaa Xaa Xaa Leu Tyr Val Xaa Phe
 1               5                   10

Xaa Xaa Xaa Gly Trp Xaa Xaa Trp Xaa
            15

Xaa Ala Pro Xaa Gly Xaa Xaa Ala
 20             25

Xaa Tyr Cys Xaa Gly Xaa Cys Xaa
        30              35

Xaa Pro Xaa Xaa Xaa Xaa Xaa
            40

Xaa Xaa Xaa Asn His Ala Xaa Xaa
            45              50

Xaa Xaa Leu Xaa Xaa Xaa Xaa Xaa
                55

Xaa Xaa Xaa Xaa Xaa Xaa Xaa Cys
 60                         65

Cys Xaa Pro Xaa Xaa Xaa Xaa Xaa
            70
```

```
          -continued
Xaa Xaa Xaa Leu Xaa Xaa Xaa
 75                 80

Xaa Xaa Xaa Xaa Val Xaa Leu Xaa
            85

Xaa Xaa Xaa Xaa Met Xaa Val Xaa
 90                         95

Xaa Cys Gly Cys Xaa
        100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14 and 32), human BMP3 (Seq. ID No. 26), human BMP5 (Seq. ID No. 27), human BMP6 (Seq. ID No. 28) and 60A (from Drosophila, Seq. ID No.

24). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

Generic Sequence 5

```
Leu Xaa Xaa Xaa Phe
 1           5

Xaa Xaa Xaa Gly Trp Xaa Xaa Trp Xaa
           10

Xaa Xaa Pro Xaa Xaa Xaa Xaa Ala
 15              20

Xaa Tyr Cys Xaa Gly Xaa Cys Xaa
     25              30

Xaa Pro Xaa Xaa Xaa Xaa
         35

Xaa Xaa Xaa Asn His Ala Xaa Xaa
     40              45

Xaa Xaa Xaa Xaa Xaa Xaa Xaa
             50

Xaa Xaa Xaa Xaa Xaa Xaa Xaa Cys
     55              60

Cys Xaa Pro Xaa Xaa Xaa Xaa
         65

Xaa Xaa Xaa Leu Xaa Xaa Xaa
 70              75

Xaa Xaa Xaa Xaa Val Xaa Leu Xaa
             80

Xaa Xaa Xaa Xaa Met Xaa Val Xaa
 85              90

Xaa Cys Xaa Cys Xaa
         95
``` wherein each Xaa is independently selected from a group of one or more specified amino acids defined as follows: "Res." means "residue" and Xaa at res.2 (Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

```
Cys Xaa Xaa Xaa Xaa Leu Xaa Xaa Xaa Phe
 1               5                  10

Xaa Xaa Xaa Gly Trp Xaa Xaa Trp Xaa
             15

Xaa Xaa Pro Xaa Xaa Xaa Xaa Ala
 20              25

Xaa Tyr Cys Xaa Gly Xaa Cys Xaa
     30              35

Xaa Pro Xaa Xaa Xaa Xaa
         40

Xaa Xaa Xaa Asn His Ala Xaa Xaa
     45              50

Xaa Xaa Xaa Xaa Xaa Xaa Xaa
             55

Xaa Xaa Xaa Xaa Xaa Xaa Xaa Cys
     60              65

Cys Xaa Pro Xaa Xaa Xaa Xaa
         70

Xaa Xaa Xaa Leu Xaa Xaa Xaa
 75              80

Xaa Xaa Xaa Xaa Val Xaa Leu Xaa
             85

Xaa Xaa Xaa Xaa Met Xaa Val Xaa
 90              95

Xaa Cys Xaa Cys Xaa
         100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17 (Asp, Arg, Asn or Glu); Xaa at res.19 (Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40= (Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58= (Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74 (Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Table II, below, and Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J. Mol. Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods and compositions of this invention is disclosed in copending U.S. patent application Ser. No. 752,764, filed Aug. 30, 1991, and Ser. No. 667,274, filed Mar. 11, 1991, the disclosures of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of enhancing bone formation and/or inhibiting abnormal bone deterioration in a variety of mammals, including humans, for use in maintaining appropriate bone mass and bone remodeling in developing and adult bone tissue.

BRIEF DESCRIPTION OF THE DRAWINGS

The foregoing and other objects and features of this invention, as well as the invention itself, may be more fully understood from the following description, when read together with the accompanying drawings, in which:

FIG. 3 compares the alkaline phosphatase induction effect of hOP-1 and TGF-β on rat osteoblasts;

DETAILED DESCRIPTION OF THE INVENTION

Figure 1:
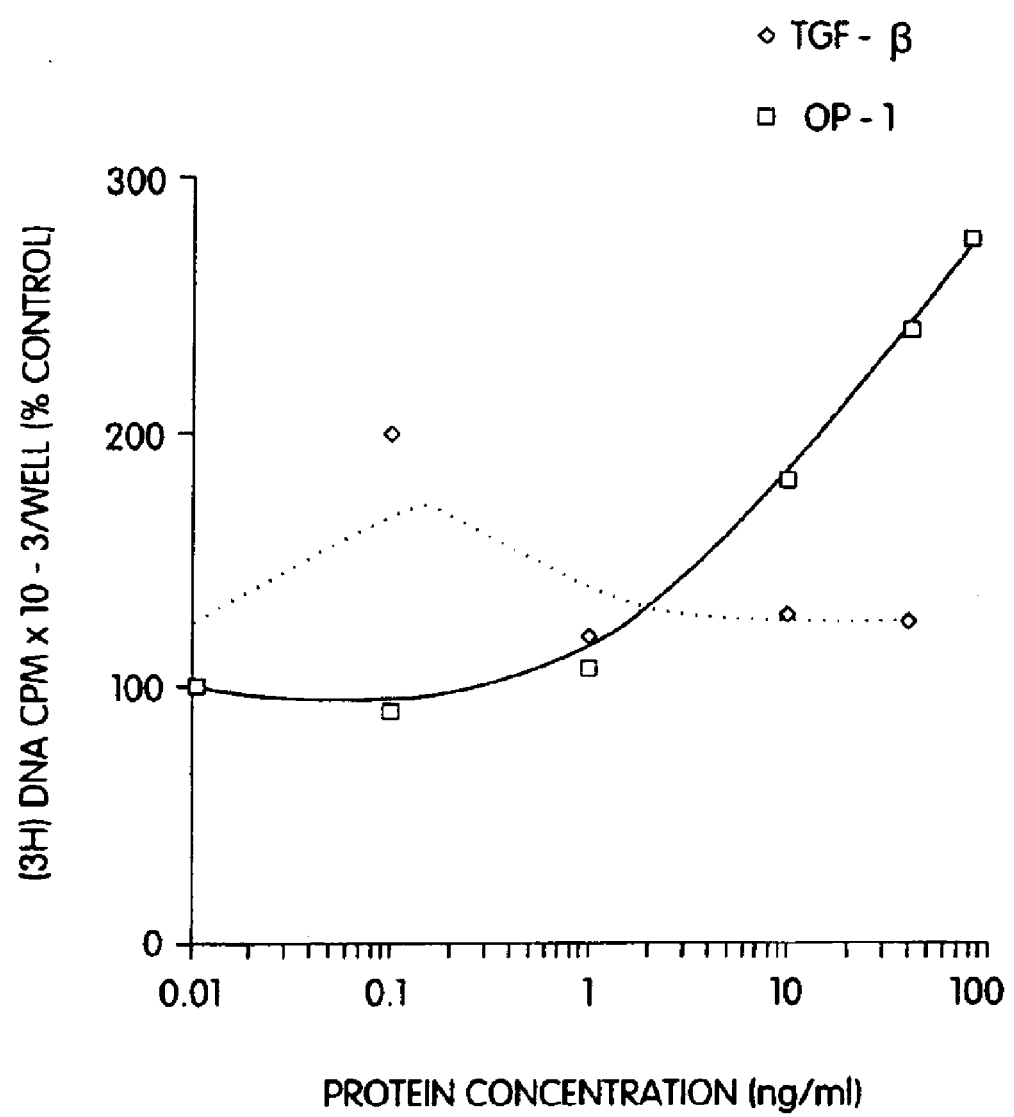
FIG. 1 compares the mitogenic effect of hOP-1 and TGF-β on rat osteoblasts.

It now has been discovered that the proteins described herein are effective agents for preventing loss of bone mass and/or for stimulating bone formation when provided systemically or injected directed into bone tissue in a mammal. As described herein, these proteins ("morphogens") may be used in the treatment of metabolic bone diseases and other disorders that cause an imbalance of the bone remodeling cycle, and/or which cause deterioration of the skeletal microstructure.

The invention is based on the discovery of a family of morphogenic proteins capable of inducing tissue morphogenesis in a mammal. More particularly, the invention is based on the discovery that these proteins play an important role, not only in embryogenesis, but also in the growth, maintenance and repair of bone tissue in juvenile and adult mammals.

It has been shown that implantation of a morphogen (including OP-1, CBMP2, DPP and 60A protein, and various biosynthetic constructs, such as COP5 and COP7) together with a suitable matrix in subcutaneous sites in mammals induces a sequence of cellular events which leads to the formation of fully functional new bone, as determined by the specific activity of alkaline phosphatase, calcium content and histology of day 12 implants (see, for example, U.S. Pat. Nos. 4,968,590 and 5,011,691, and U.S. Ser. Nos. 667,274 and 752,857, the disclosures of which are incorporated herein by reference.) The morphogen-containing implants recruit nearby mesenchymal stem cells and trigger their differentiation into chondrocytes within 5–7 days. Upon capillary invasion, the chondrocytes hypertrophy, become calcified and subsequently are replaced by newly formed bone within 9–12 days. The mineralized bone then is remodeled extensively and becomes occupied by ossicles filled with functional bone marrow elements by 14–21 days.

As described herein, the morphogens provided herein stimulate the proliferation, growth and differentiation of osteoblasts in vitro (see Examples 2–7, below), and can induce bone formation in osteoporotic bone tissue in vivo when provided systemically to a mammal, or directly to bone tissue, without an associated matrix carrier (see Examples 8, 9, below.) In addition, the morphogens inhibit multinucleation of activated early mononuclear phagocytic cells (see Example 12, below). Moreover, inhibition of endogenous morphogen activity can inhibit normal skeleton development in a mammal (see Example 13, below.)

As described in Example 1 and in detail in copending U.S. Ser. Nos. 752,764 and 752,861, the disclosures of which are incorporated herein by reference, the naturally-occurring morphogens are widely distributed in the different tissues of the body. For example, as determined by northern blot hybridization, OP-1 is expressed primarily in the tissue of the urogental tract (e.g., renal and bladder tissues). By contrast, Vgr-1, BMP3, BMP4 and BMP5 appear to be expressed primarily in the heart and lung. BMP5 also appears to be expressed significantly in liver tissue. GDF-1 appears to be expressed primarily in brain tissue. (See, for example, Ozkaynak et al. (1992) JBC, in publicalion.) Moreover, the tissue of synthesis may differ from the natural site of action of specific morphogens. For example, although OP-1 appears to be primarily synthesized in renal tissue, the protein is active in bone tissue. In addition, at least one morphogen, OP-1, is present in a number of body fluids, including saliva, milk (including mammary gland extract, colostrum and 57-day milk) and serum (see Example 11, below.) Accordingly, without being limited to a given theory, the morphogens described herein may behave as endocrine factors, e.g., proteins secreted from a factor-producing tissue in response to particular stimuli, and capable of being transported to, and acting on, a distant tissue. These findings further distinguish morphogens from other members of the TGF-β superfamily of proteins, including TGF-β, which act as local or autocrine factors produced by the tissue on which they act.

The pro domain may function to enhance protein solubility and/or to assist in tissue targeting of morphogens to particular tissues. For example, the mature, active form of OP-1 appears to be secreted from cells in association with the pro domain of the intact sequence. Accordingly, while, as explained herein, the morphogens useful in this invention have significant amino acid sequence homologies within the active domains and are similar in their ability to induce tissue morphogenesis, without being limited to any theory, it is hypothesized that the sequence variation within the morphogenic protein family members may reflect the different specific roles each morphogen plays in specific tissues under natural occurring conditions. For example, the significant sequence variation within the pro domains may mean that these regions of the protein sequence are important for targeting specific morphogens to different tissues for morphogenic activity therein.

Accordingly, the present invention comprises two fundamental aspects. In one aspect, the methods and compositions of this invention comprise a morphogen which, when administered to an individual, is capable of inhibiting loss of bone mass and/or stimulating bone formation in the individual. In another aspect, the methods and compositions of the invention comprise a morphogen-stimulating agent which, when administered to an individual, is capable of inducing the expression and/or secretion of sufficient endogenous morphogen within the individual to provide therapeutically effective concentrations capable of inhibiting loss of bone mass and/or stimulating bone formation in the individual.

Example 14 describes an assay for screening compounds to identify candidate morphogen-stimulating agents. A detailed description of useful screening assays for identifying candidate morphogen-stimulating agents also is provided in U.S. Ser. No. 752,861, the disclosure of which is incorporated herein by reference. Candidate agents then may be tested for their efficacy in vivo using, for example, the osteoporosis model described in Examples 8 and 9 below.

Provided below are detailed descriptions of suitable morphogens useful in the methods and compositions of this invention, as well as methods for the administration and application of these morphogens and/or of morphogen-stimulating agents. Also provided are numerous, nonlimiting examples which 1) illustrate the suitability of the morphogens and morphogen-stimulating agents described herein as therapeutic agents for inhibiting abnormal bone loss and/or for enhancing bone formation in a human, and 2) provide assays with which to test candidate morphogens and morphogen-stimulating agents for their efficacy.

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, the disclosures of which are hereby incorporated by reference. As disclosed therein, the morphogens may be purified from naturally-sourced material or recombinantly produced from procaryotic or eucaryotic host cells, using the genetic sequences disclosed therein. Alternatively, novel morphogenic sequences may be identified following the procedures disclosed therein.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence

```
     Cys Xaa Xaa Xaa Xaa       (Seq. ID No. 15)
      1           5
```

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID No. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | | |
|---|---|---|---|---|---|---|---|---|
| hOP-1 | Cys | Lys | Lys | His | Glu | Leu | Tyr | Val |
| mOP-1 | | | | | | | | |
| hOP-2 | | Arg | Arg | | | | | |
| mOP-2 | | Arg | Arg | | | | | |
| DPP | | Arg | Arg | | Ser | | | |
| Vgl | | | Lys | Arg | His | | | |
| Vgr-1 | | | | | Gly | | | |
| CBMP-2A | | | Arg | | Pro | | | |
| CBMP-2B | | Arg | Arg | | Ser | | | |
| BMP3 | ... | Ala | Arg | Arg | Tyr | ... | Lys | ... |
| GDF-1 | .. | Arg | Ala | Arg | Arg | .. | .. | .. |
| 60A | | Gln | Met | Glu | Thr | | | |
| BMP5 | | | | | | | | |
| BMP6 | | Arg | | | | | | |
| | 1 | | | | 5 | | | |
| hOP-1 | Ser | Phe | Arg | Asp | Leu | Gly | Trp | Gln | Asp |
| mOP-1 | | | | | | | | | |
| hOP-2 | | | Gln | | | | | Leu | |
| mOP-2 | Ser | | | | | | | Leu | |
| DPP | Asp | | Ser | | Val | | | Asp | |
| Vgl | Glu | | Lys | | Val | | | | Asn |
| Vgr-1 | | | Gln | | Val | | | | |
| CBMP-2A | Asp | | Ser | | Val | | | Asn | |
| CBMP-2B | Asp | | Ser | | Val | | | Asn | |
| BMP3 | Asp | ... | Ala | ... | Ile | ... | ... | Ser | Glu |
| GDF-1 | .. | .. | .. | Glu | Val | .. | .. | His | Arg |
| 60A | Asp | | Lys | | | | | His | |
| BMP5 | | | | | | | | | |
| BMP6 | | | Gln | | | | | | |
| | | | 10 | | | | | 15 | |
| hOP-1 | Trp | Ile | Ile | Ala | Pro | Glu | Gly | Tyr | Ala |
| mOP-1 | | | | | | | | | |
| hOP-2 | | Val | | | | Gln | | | Ser |
| mOP-2 | | Val | | | | Gln | | | Ser |
| DPP | | | | Val | | Leu | | | Asp |
| Vgl | | Val | | | | Gln | | | Met |
| Vgr-1 | | | | | | Lys | | | |
| CBMP-2A | | Val | | | | Pro | | | His |
| CBMP-2B | | Val | | | | Pro | | | Gln |
| BMP3 | ... | ... | ... | Ser | ... | Lys | Ser | Phe | Asp |
| GDF-1 | .. | Val | .. | .. | .. | Arg | .. | Phe | Leu |
| 60A | | | | | | | | | Gly |
| BMP5 | | | | | | | | | |
| BMP6 | | | | | | Lys | | | |
| | | | | 20 | | | | | 25 |
| hOP-1 | Ala | Tyr | Tyr | Cys | Glu | Gly | Glu | Cys | Ala |
| mOP-1 | | | | | | | | | |
| hOP-2 | | | | | | | | | Ser |
| mOP-2 | | | | | | | | | |

TABLE II-continued

| | | | | | | | |
|---|---|---|---|---|---|---|---|
| DPP | | | His | Lys | | Pro | |
| Vgl | Asn | | Tyr | | | Pro | |
| Vgr-1 | Asn | | Asp | | | Ser | |
| CBMP-2A | Phe | | His | Glu | | Pro | |
| CBMP-2B | Phe | | His | Asp | | Pro | |
| BMP3 | ... | ... ... | ... Ser | ... Ala | ... | Gln | |
| GDF-1 | .. Asn | .. .. | Gln .. | Gln | .. | .. | |
| 60A | Phe | | Ser | | | Asn | |
| BMP5 | Phe | | Asp | | | Ser | |
| BMP6 | Asn | | Asp | | | Ser | |
| | | | 30 | | | 35 | |

| | | | | | | | |
|---|---|---|---|---|---|---|---|
| hOP-1 | Phe | Pro | Leu | Asn | Ser | Tyr | Met Asn Ala |
| mOP-1 | | | | | | | |
| hOP-2 | | | | Asp | | Cys | |
| mOP-2 | | | | Asp | | Cys | |
| DPP | | | Ala | Asp | His | Phe | Ser |
| Vgl | Tyr | | Thr | Glu | Ile | Leu | Gly |
| Vgr-1 | | | Ala | His | | | |
| CBMP-2A | | | Ala | Asp | His | Leu | Ser |
| CBMP-2B | | | Ala | Asp | His | Leu .. | Ser |
| GDF-1 | Leu .. | Val | Ala | Leu | Ser | Gly | Ser** .. |
| BMP3 | ... ... | Met | Pro | Lys | Ser | Leu | Lys Pro |
| 60A | | | Ala | His | | | |
| BMP5 | | | Ala | His | Met | | |
| BMPG | | | Ala | His | Met | | |
| | | | | | | 40 | |

| | | | | | | | |
|---|---|---|---|---|---|---|---|
| hOP-1 | Thr | Asn | His | Ala | Ile | Val Gln Thr Leu |
| mOP-1 | | | | | | |
| hOP-2 | | | | | Leu | Ser |
| mOP-2 | | | | | Leu | Ser |
| DPP | | | | Val | | |
| Vgl | Ser | | | | Leu | |
| Vgr-1 | | | | | | |
| CBMP-2A | | | | | | |
| CBMP-2B | | | | | | |
| BMP3 | Ser ... | ... ... | Thr | Ile | ... | Ser Ile |
| GDF-1 | Leu .. | . | .. | Val | Leu | Arg Ala .. |
| 60A | | | | | | |
| BMP5 | | | | | | |
| BMP6 | | | | | | |
| | 45 | | | | 50 | |

| | | | | | | | |
|---|---|---|---|---|---|---|---|
| hOP-1 | Val | His | Phe | Ile | Asn | Pro | Glu Thr Val |
| mOP-1 | | | | | | | Asp |
| hOP-2 | | His | Leu | Met | Lys | | Asn Ala |
| mOP-2 | | His | Leu | Met | Lys | | Asp Val |
| DPP | | Asn | Asn | Asn | | | Gly Lys |
| Vgl | | Ser | | | Glu | | Asp Ile |
| Vgr-1 | | Val | Met | | | | Tyr |
| CBMP-2A | | Asn | Ser | Val | | Ser --- | Lys Ile |
| CBMP-2B | | Asn | Ser | Val | | Ser --- | Ser Ile |
| BMP3 | ... | Arg | Ala**Gly | Val | Val | Pro | Gly Ile |
| GDF-1 | Met .. | Ala | Ala | Ala | .. | | Gly Ala Ala |
| 60A | | Leu | Leu | Glu | | | Lys Lys |
| BMP5 | | Leu | Met | Phe | | | Asp His |
| BMP6 | | Leu | Met | | | | Tyr |
| | 55 | | | | 60 | | |

| | | | | | | | |
|---|---|---|---|---|---|---|---|
| hOP-1 | Pro | Lys | Pro | Cys | Cys | Ala | Pro Thr Gln |
| mOP-1 | | | | | | | |
| hOP-2 | | Ala | | | | | Lys |
| mOP-2 | | Ala | | | | | Lys |
| DPP | | Ala | | Val | | | |
| Vgl | Leu | | | Val | | | Lys |
| Vgr-1 | | | | | | | Lys |
| CBMP-2A | | Ala | | Val | | | Glu |
| CBMP-2B | | Ala | | Val | | | Glu |
| BMP3 | ... Glu | ... | ... | ... Val | ... | Glu | Lys |
| GDF-1 | Asp Leu | .. | .. | .. Val | .. | Ala | Arg |
| 60A | | | | | | | Arg |
| BMP5 | | | | | | | Lys |
| BMP6 | | | | | | | Lys |
| | | 65 | | | | | 70 |

| | | | | | | | |
|---|---|---|---|---|---|---|---|
| hOP-1 | Leu | Asn | Ala | Ile | Ser | Val | Leu Tyr Phe |
| mOP-1 | | | | | | | |
| hOP-2 | | Ser | | Thr | | | Tyr |
| mOP-2 | | Ser | | Thr | | | Tyr |
| Vgl | Met Ser | Pro | | | Met | | Phe Tyr |
| Vgr-1 | Val | | | | | | |
| DPP | | Asp Ser | Val | Ala | Met | | Leu |
| CBMP-2A | | Ser | | | Met | | Leu |
| CBMP-2B | | Ser | | | Met | | Leu |
| BMP3 | Met Ser | Ser | Leu | ... | Ile | ... | Phe Tyr |
| GDF-1 | .. Ser | Pro | .. | . | .. | .. | Phe .. |
| 60A | ... Gly | ... | Leu | Pro | ... | ... | ... His |
| BMP5 | ... ... | ... | ... | ... | ... | ... | ... ... |
| BMP6 | ... ... | ... | ... | ... | ... | ... | ... ... |
| | | | | 75 | | | 80 |

| | | | | | | | |
|---|---|---|---|---|---|---|---|
| hOP-1 | Asp | Asp | Ser | Ser | Asn | Val | Ile Leu Lys |
| mOP-1 | | | | | | | |
| hOP-2 | | Ser | | Asn | | | Arg |
| mOP-2 | | Ser | | Asn | | | Arg |
| DPP | Asn | | Gln | | Thr | | Val |
| Vgl | | Asn | Asn | Asp | | | Val Arg |
| Vgr-1 | | | Asn | | | | |
| CBMP-2A | | Glu | Asn | Glu | Lys | | Val |
| CBMP-2B | | Glu | Tyr | Asp | Lys | | Val |
| BMP3 | ... | Glu | Asn | Lys | ... | ... | Val ... ... |
| GDF-1 | .. | Asn .. | Asp | .. | .. | Val .. | Arg |
| 60A | Leu | Asn | Asp | Glu | | | Asn |
| BMP5 | | | | | | | |
| BMP6 | | Asn | | | | | |
| | | | | | 85 | | |

| | | | | | | | |
|---|---|---|---|---|---|---|---|
| hOP-1 | Lys | Tyr | Arg | Asn | Met | Val | Val Arg |
| mOP-1 | | | | | | | |
| hOP-2 | | His | | | | | Lys |
| mOP-2 | | His | | | | | Lys |
| DPP | Asn | | Gln | Glu | | Thr | Val |
| Vgl | His | | Glu | | | Ala | Asp |
| Vgr-1 | | | | | | | |
| CBMP-2A | Asn | | Gln | Asp | | | Glu |
| CBMP-2B | Asn | | Gln | Glu | | | Glu |
| BMP3 | Val | ... | Pro | ... | ... | Thr | ... Glu |
| GDF-1 | Gln .. | | Glu | Asp .. | .. | .. | Asp |
| 60A | | | | | Ile | | Lys |
| BMP5 | | | | | | | |
| BMPG | | | Trp | | | | |
| | 90 | | | | | 95 | |

| | | | | |
|---|---|---|---|---|
| hOP-1 | Ala | Cys | Gly | Cys | His |
| mOP-1 | | | | | |
| hOP-2 | | | | | |
| mOP-2 | | | | | |
| DPP | Gly | | | Arg | |
| Vgl | Glu | | | Arg | |
| Vgr-1 | | | | | |
| CBMP-2A | Gly | | | Arg | |
| CBMP-2B | Gly | | | Arg | |
| BMP3 | Ser | ... Ala | ... | Arg | |
| GDF-1 | Glu .. | .. | .. | Arg | |
| 60A | Ser | | | | |
| BMP5 | Ser | | | | |
| BMP6 | | | | | |
| | | | 100 | | |

**Between residues 56 and 57 of BMP3 is a Val residue; between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP-1 sequence described therein, the GDF-1 sequence shares greater than 70% amino acid sequence homology (or "similarity") with the hOP-1 sequence, where "homology" or "similarity" includes allowed conservative amino acid changes within the sequence as defined by Dayoff, et al., *Atlas of Protein*

Sequence and Structure vol. 5, supp. 3, pp. 345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP-1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. Formulations and Methods for Administering Therapeutic Agents

The morphogens may be provided to an individual by any suitable means, preferably directly, parenterally or orally. Where the morphogen is to be provided directly (e.g., locally, as by injection, to a bone tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (9.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, association of the mature dimer with the pro domain of the morphogen increases solubility of the protein significantly. In fact, the endogenous protein is thought to be transported in this form. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferablly bioresorbable polymers, including, for example, hyaluronic acid, collagen, tricalcium phosphate, polybutyrate, lactide and lactide/glycolide copolymers, may be useful excipients to control the release of the morphogen in vivo. Other potentially useful parenteral delivery systems for these morphogens include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration.

Alternatively, the morphogens described herein may be administered orally. Oral administration of proteins as therapeutics generally is not practiced as most proteins readily are degraded by digestive enzymes and acids in the mammalian digestive system before they can be absorbed into the bloodstream. However, the morphogens described herein typically are acid-stable and protease-resistant (see, for example, U.S. Pat. No. 4,968,590.) In addition, at least one morphogen, OP-1, has been identified in bovine mammary gland extract, colostrum and milk (see Example 10, below) as well as saliva. Moreover, the OP-1 purified from mammary gland extract has been shown to be morphogenically active. Specifically, this protein has been shown to induce endochondral bone formation in mammals when implanted subcutaneously in association with a suitable matrix material, using a standard in vivo bone assay, such as is disclosed in U.S. Pat. No. 4,968,590. In addition, endogenous morphogen also has been detected in the bloodstream (see Example 11). These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with the pro domain of the intact sequence and/or by association with one or more milk components. Accordingly, the compounds provided herein also may be associated with molecules capable of enhancing their solubility in vitro or in vivo, including, for example, part or all of a morphogen pro domain, and casein, as described above.

The compounds provided herein also may be associated with molecules capable of targeting the morphogen or morphogen-stimulating agent to bone tissue. For example, tetracycline and diphosphonates are known to bind to bone mineral, particularly at zones of bone remodeling, when they are provided systemically in a mammal. Alternatively, an antibody or other binding protein that interacts specifically with a surface molecule on bone tissue cells also may be used. Such targeting molecules further may be covalently associated to the morphogen or morphogen-stimulating agent with, for example, an acid labile bond such as an Asp-Pro linkage, using standard chemical means well known in the art. Because the local environment at bone remodeling sites is acidic, acid-labile linkages are expected to be preferentially cleaved at these sites, yielding active morphogen or morphogen-stimulating agent at the desired site. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences which diverge significantly in the sequences which define the pro domain. Accordingly, the pro domain may be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of pro domains, which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting morphogen to bone tissue is part or all of a morphogen pro domain, particularly part or all of the pro domains of OP-1, BMP2 or BMP4, all of which proteins are found naturally associated with bone tissue.

Finally, the morphogens or morphogen-stimulating agents provided herein may be administered alone or in combination with other molecules known to have a beneficial effect on maintaining appropriate bone remodeling cycles in an individual at risk for excessive bone loss. Examples of useful cofactors include vitamin $D_3$, calcitonin, prostaglandins, parathyroid hormone, dexamethasone, estrogen and IGF.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated for parenteral or oral administration to humans or other mammals in therapeutically effective amounts, e.g., amounts which provide appropriate concentrations of a morphogen to bone tissue for a time sufficient to inhibit loss of bone mass and/or to stimulate bone formation in individuals suffering from metabolic bone diseases and other bone remodeling disorders as described above. Therapeutic concentrations also are sufficient to repair fractures and other defects in skeletal microstructure, and to enhance maintenance of appropriate bone mass in developing juveniles and adults, including protecting individuals at risk for bone mass deterioration.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of bone loss or defect, the overall health status of the particular patient, the relative biological efficacy of the compound selected, the formulation of the compound excipients, and its route of administration. In general terms, the compounds of this invention may be provided in an aqueous physiological buffer solution containing about 0.1 to 10% w/v compound for parenteral administration. Typical dose ranges are from about 10 ng/kg to about 1 g/kg of body weight per day; a preferred dose range is from about 0.1 µg/kg to 100 mg/kg of body weight per day. Optimally, the morphogen dosage given in all cases is between 2–20 µg of protein per kilogram weight of the patient per day. Currently preferred dose ranges for local injection of soluble morphogen to bone tissue are 0.1–50 µg morphogen/injection. No obvious morphogen-induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalties.

III. EXAMPLES

Example 1

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) *PNAS* 86:4554–4558 for a description of the cDNA sequence). Similarly, particularly useful mOP-1-specific probe sequences are the BstX1-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-Pst1 fragment, an 0.3 Kb fragment containing a portion of the 3'untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al.

((1987) *Anal. Biochem* 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 752,764, and in Ozkaynak, et al., (1991) *Biochem. Biophys. Res. Commn.* 179:116–123, and Ozkaynak, et al. (1992) (JBC, in press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2

Mitogenic Effect of Morphogen on Rat and Human Osteoblasts

The ability of a morphogen to induce proliferation of osteoblasts may be determined in vitro using the following assay. In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast culture obtained from established cell lines. Unless otherwise indicated, all chemicals referenced are standard, commercially available reagents, readily available from a number of sources, including Sigma Chemical, Co., St. Louis; Calbiochem, Corp., San Diego, and Aldrich Chemical Co., Milwaukee.

Rat osteoblast-enriched primary cultures were prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) *PNAS* 72:3167–3171. Rat osteoblast single cell suspensions then were plated onto a multi-well plate (e.g., a 48 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells were incubated for 24 hours at 37° C., at which time the growth medium was replaced with alpha MEM containing 1% FBS and the cells incubated for an additional 24 hours so that cells were in serum-deprived growth medium at the time of the experiment.

The cell culture then was divided into three groups: (1) wells which received 0.1, 1.0, 10.0, 40 and 80.0 ng of morphogen; (2) wells which received 0.1, 1.0, 10.0 and 40 ng of a local-acting growth factor; and (3) the control group, which received no growth factors. In this example, OP-1 was the morphogen tested, and TGF-β was the local-acting growth factor. The cells then were incubated for an additional 18 hours after which the wells were pulsed with 2 mCi/well of $^3$H-thymidine and incubated for six more hours. The excess label then was washed off with a cold solution of 0.15 M NaCl, 250 µl of 10% tricholoracetic acid then was added to each well and the wells incubated at room temperature for 30 minutes. The cells then were washed three times with cold distilled water, and lysed by the addition of 250 µl of 1% sodium dodecyl sulfate (SDS) for a period of 30 minutes at 37° C. The cell lysates then were harvested using standard means well known in the art, and the incorporation of $^3$H-thymidine into cellular DNA was determined by liquid scintillation as an indication of mitogenic activity of the cells. The results, shown in FIG. 1, demonstrate that OP-1 (identified in the figure by squares) stimulates .sup.$^3$H-thymidine incorporation into DNA, and thus promotes osteoblast cell proliferation. The mitogenesis stimulated by 40 ng of OP-1 in serum-free medium was equivalent to the mitogenic effect of 10% fresh serum alone. By contrast, the effect of TGF-β (indicated by diamonds in FIG. 1) is transient and biphasic. At high concentrations, TGF-β has no significant effect on osteoblast cell proliferation. This system may be used to test other morphogens for their effect on cell proliferation.

The in vitro effect of a morphogen on osteoblast proliferation also was tested on human primary osteoblasts (obtained from bone tissue of a normal adult patient and prepared as described above) and on osteosarcoma-derived cells, and in all cases induced cell proliferation. In addition, similar experiments, performed using BMP4 (BMP2B) and BMP3 shows these morphogens also can stimulate osteoblast proliferation and growth. (See Chen et al., (1991) *J. Bone and Min. Res.* 6: 1387–1393, and Vukicevic, (1989) *PNAS* 86: 8793–8797.)

The effect of a given morphogen on bone cell growth and/or development also may be tested using a variety of bone cell markers: e.g., collagen synthesis, alkaline phosphatase activity, parathyroid hormone-mediated cyclic AMP (cAMP) production, osteocalcin synthesis, and by assessing the rate of mineralization in osteoblasts. Of these, alkaline phosphatase activity, parathyroid hormone-mediated cAMP production, osteocalcin synthesis and mineralization promotion are specific markers for the differentiated osteoblast phenotype. Experimental systems for testing these parameters as well as collagen synthesis are described below in Examples 3–7. In all cases morphogen alone stimulated expression of these phenotype-specific markers. In Examples 3–7 OP-1 was the morphogen tested. Similar experiments, performed using BMP4 (BMP2B) shows that this morphogen also induces osteoblast differentiation. (See Chen, et al. (1991) *T. Bone and Min. Res.* 6: 1387–1392, and Vukicevic, (1989) *PNAS* 86: 8793–8797.)

Example 3

Effect of Morphogen on Collagen Synthesis in Rat Osteoblasts

The effect of a morphogen on collagen production in rat osteoblasts in vitro may be determined as follows.

Rat osteoblasts were prepared and cultured in a multi-well plate as described for Example 2. In this example a 24-well plate was used. The cultured cells then were divided into three groups: (1) wells which received 1, 10 or 40 ng of morphogen per ml of medium; (2) wells which received 1, 10 or 40 ng of a local-acting growth factor per ml of medium; and (3) a control group which received no growth factors. In this example, OP-1 was the morphogen tested, and TGF-β was the local-acting growth factor.

Figure 2:
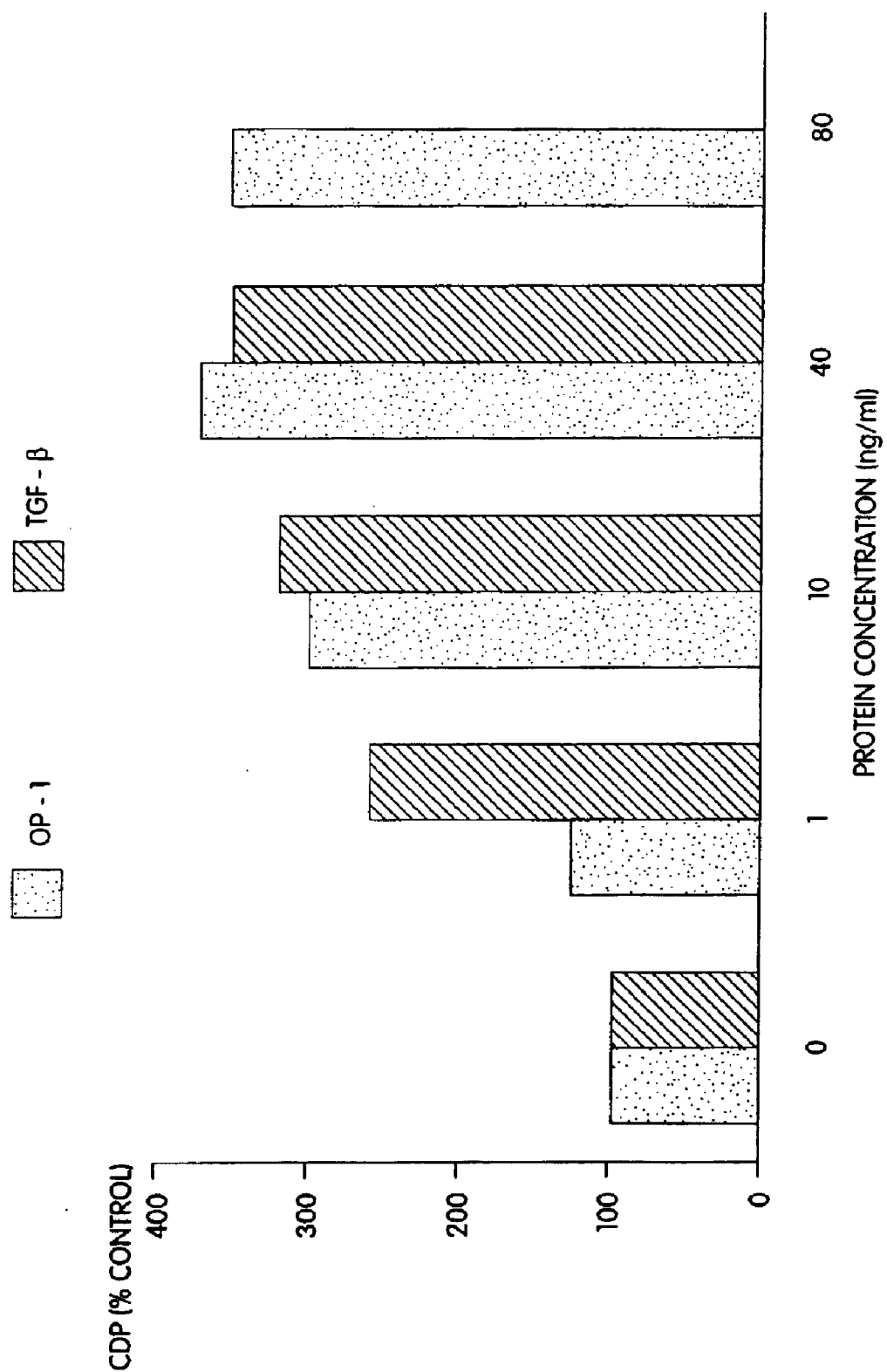
FIG. 2 illustrates the effect of human osteogenic protein-1 (hOP-1) on the collagen synthesis of osteoblasts.

The samples were incubated for 68 hours at 37° C. with 5% $CO_2$ in a humidified incubator. Twenty-five (25) μCi of $^3H$ proline were added into each well and incubated for six additional hours. The cells then were frozen at −20° C. until the collagen assay was performed. The cells then were assayed for collagen production by detecting incorporation of $^3H$-proline into total collagenase-digestible protein (CDP). The results, shown in FIG. 2, demonstrate that OP-1 stimulates type-I collagen synthesis, as measured by $^3H$-proline incorporation into total CDP. Thus, OP-1 promotes collagen synthesis in vitro by preosteoblasts and mature osteoblasts.

Example 4

Alkaline Phosphatase Induction of Osteoblasts by Morphogen 4.1 Morphogen-Specific Alkaline Phosphatase Induction Since alkaline phosphatase production is an indicator of bone formation by differentiated, functional osteoblasts, a morphogen may be assessed for its potential osteogenic effects using this osteoblast marker in the following in vitro test system.

Rat osteoblasts were prepared and cultured in a multi-well plate as described for Example 2. In this example a 24-well plate was used. The cultured cells then were divided into three groups: (1) wells which received varying concentrations of morphogen; (2) wells which received varying concentrations of a local-acting growth factor; and (3) a control group which received no growth factors. In this example OP-1 was the morphogen tested at the following concentrations: 0.1, 1.0, 10.0, 40.0 or 80.0 ng/ml medium; and TGF-β was the local-acting growth factor, tested at 0.1, 1.0, 10.0, 40.0 or 80.0 ng/ml medium. The cells then were incubated for 72 hours. After the incubation period the cell layer was extracted with 0.5 ml of 1% Triton X-100. The resultant cell extract was centrifuged, 100 μl of the extract was added to 90 μl of paranitrosophenylphospate (PNPP)/glycerine mixture and incubated for 30 minutes in a 37° C. water bath and the reaction stopped with 100 μl NaOH. The samples then were run through a plate reader (e.g., Dynatech MR700 plate reader, and absorbance measured at 400 nm, using p-nitrophenol as a standard) to determine the presence and amount of alkaline phosphate activity. Protein concentrations were determined by the Biorad method. Alkaline phosphatase activity was calculated in units/μg protein, where 1 unit=1 mmol p-nitrophenol liberated/30 minutes at 37° C.

The results, shown in FIG. 3, illustrate that morphogen alone stimulates the production of alkaline phosphatase in osteoblasts, and thus promotes the growth and expression of the osteoblast differentiated phenotype. In the figure, squares represent OP-1 concentrations, and diamonds represent TGF-β concentrations.

4.2. Long Term Effect of Morphogen on the Production of Alkaline Phosphatase by Rat Osteoblasts In order to determine the long term effect of a morphogen on the production of alkaline phosphatase by rat osteoblasts, the following assay may be performed.

Figure 4:
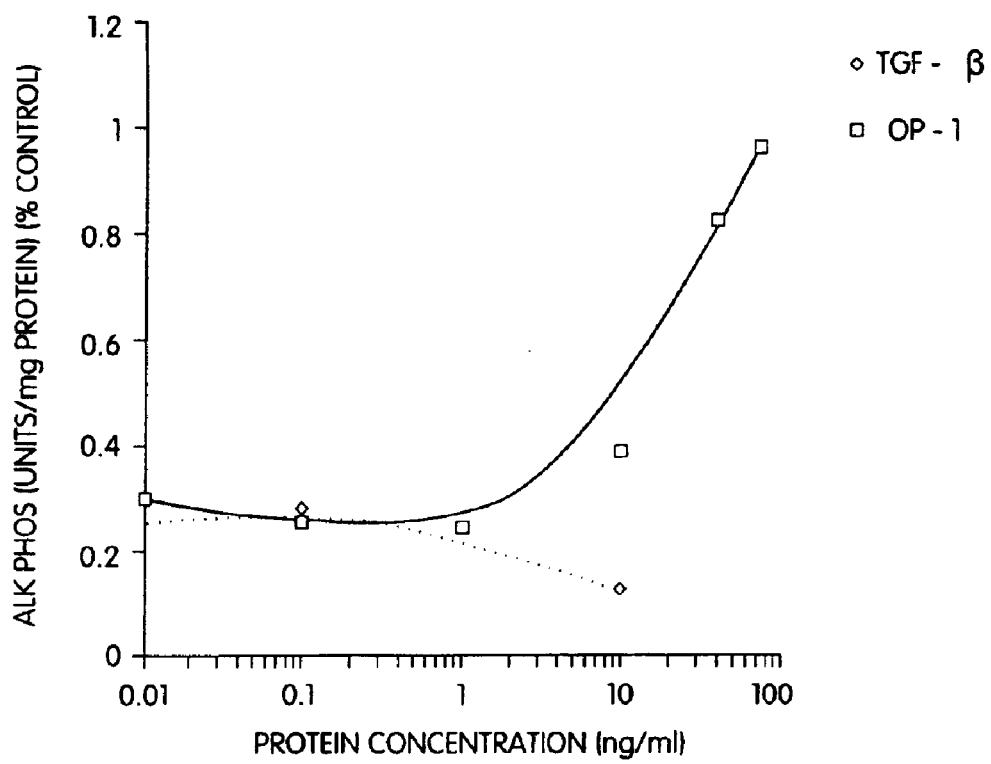
FIG. 4 shows the long-term effect of hOP-1 on the production of alkaline posphatase by rat osteoblasts.

Rat osteoblasts were prepared and cultured in multi-well plates as described in Example 2. In this example six sets of 24 well plates are plated with 50,000 rat osteoblasts per well. The wells in each plate, prepared as described above, then were divided into three groups: (1) those which received 1 ng of morphogen per ml of medium; (2) those which received 40 ng of morphogen/ml of medium; and (3) those which received 80 ng of morphogen/ml of medium. Each plate then was incubated for different lengths of time: 0 hours (control time), 24 hours, 48 hours, 96 hours, 120 hours and 144 hours. After each incubation period, the cell layer was extracted with 0.5 ml of 1% Triton X-100. The resultant cell extract was centrifuged, and alkaline phosphatase activity determined as for Example 4, using paranitrosophenylphosphate (PNPP). The results, shown in FIG. 4, illustrate that morphogen alone stimulates the production of alkaline phosphatase in osteoblasts, that increasing doses of OP-1 further increase the level of alkaline phosphatase production, and that the morphogen-stimulated elevated levels of alkaline phosphatase in the treated osteoblasts lasts for an extended period of time. In the figure, circles represent 1 ng OP-1; squares, 40 ng OP-1; and diamonds, 80 ng OP-1.

Example 5

Morphogen-Induced Parathyroid Hormone Mediated cAMP Production in Rat Osteoblasts The effect of a morphogen on parathyroid hormone-mediated cAMP production in rat osteoblasts in vitro may be determined as follows.

Figure 5:
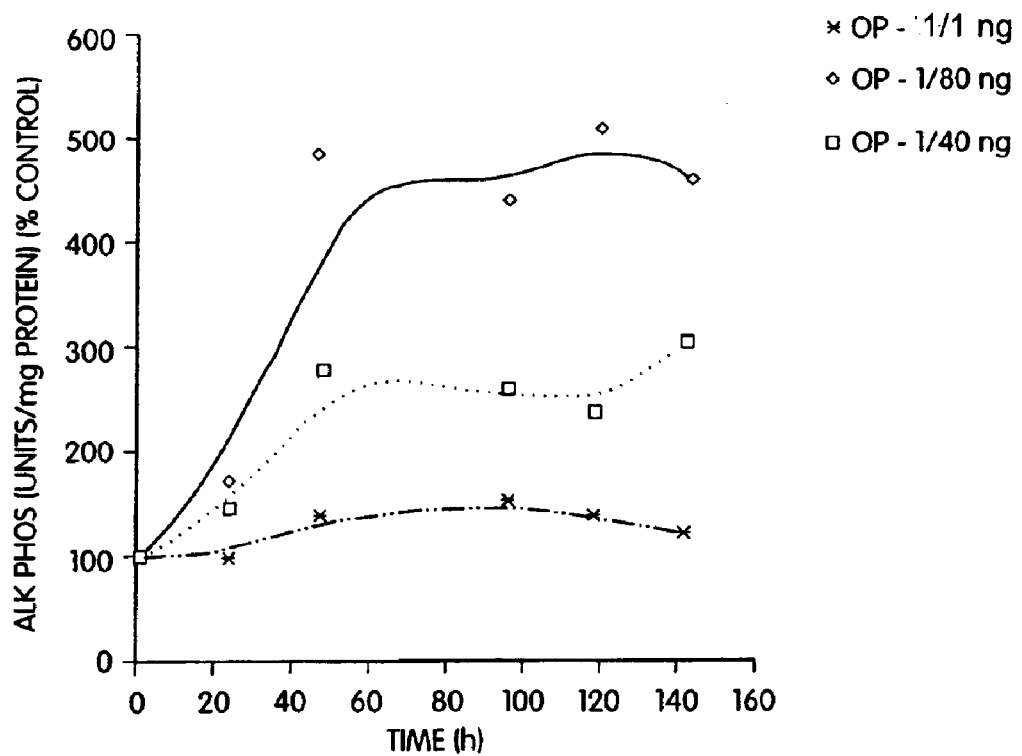
FIG. 5 shows the effect of hOP-1 on parathyroid hormone-mediated cAMP production using rat osteoblasts in culture.

Rat osteoblasts were prepared and cultured in a multiwell plate as described for Example 2 above. In this example a 24-well plate was used. The cultured cells then were divided into three groups: (1) wells which received varying concentrations of morphogen (in this example, OP-1, at 1.0, 10.0 and 40.0 ng/ml medium); (2) wells which received varying concentrations of a local-acting growth factor (in this example, TGF-β, at 0.1, 1.0, and 5.0 ng/ml medium); and (3) a control group which received no growth factors. The plate was then incubated for another 72 hours. At the end of the 72 hours the cells were treated with medium containing 0.5% bovine serum albumin (BSA) and 1 mM 3-isobutyl-1-methyl xanthine for 20 minutes followed by the addition into half of the wells of human recombinant parathyroid hormone (hPTH, Sigma, St. Louis) at a concentration of 200 ng/ml for 10 minutes. The cell layer was extracted from each well with 0.5 ml of 1% Triton X-100. The cAMP levels were then determined using a radioimmunoassay kit (Amersham, Arlington Heights, Ill.). The results, shown in FIG. 5, demonstrate that morphogen alone stimulates an increase in the PTH-mediated cAMP response, and thus promotes the growth and expression of the osteoblast differentiated phenotype.

Example 6

Effect of Morphogen on Osteocalcin Synthesis and the Rate of Mineralization by Osteoblasts in Culture Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to assay morphogen efficacy in vitro.

Rat osteoblasts are prepared and cultured in a multi-well plate as for Example 2. In this example cells were cultured in a 24-well plate. In this experiment the medium was supplemented with 10%FBS, and on day 2, cells were fed with fresh medium supplemented with fresh 10 mM b-glycerophosphate (Sigma, Inc.). Beginning on day 5 and twice weekly thereafter, cells were fed with a complete mineralization medium containing all of the above components plus fresh L(+)-ascorbate, at a final concentration of 50 μg/ml medium. Morphogen then was added to the wells directly. In this example, OP-1 in 50% acetonitrile (or 50% ethanol) containing 0.1% trifluoroacetic acid (TFA) was added at no more than 5 μl morphogen/ml medium. Control wells received solvent vehicle only. The cells then were re-fed and the conditioned medium sample diluted 1:1 in standard radioimmunoassay buffer containing standard protease inhibitors and stored at −20° C. until assayed for osteocalcin. Osteocalcin synthesis then was measured by standard radioimmoassay using a commercially available rat osteocalcin-specific antibody.

Mineralization was determined on long term cultures (13 day) using a modified von Kossa staining technique on fixed cell layers: cells were fixed in fresh 4% paraformaldehyde at 23° C. for 10 mn, following rinsing cold 0.9% NaCl. Fixed cells then were stained for endogenous alkaline phosphatase at pH 9.5 for 10 min, using a commercially available kit (Sigma, Inc.) Purple stained cells then were dehydrated with methanol and air dried. after 30 min incubation in 3% $AgNO_3$ in the dark, $H_2O$-rinsed samples were exposed for 30 sec to 254 nm UV light to develop the black silver-stained phosphate nodules. Individual mineralized foci (at least 20 mm in size) were counted under a dissecting microscope and expressed as nodules/culture (see FIG. 6B).

Figure 6A:
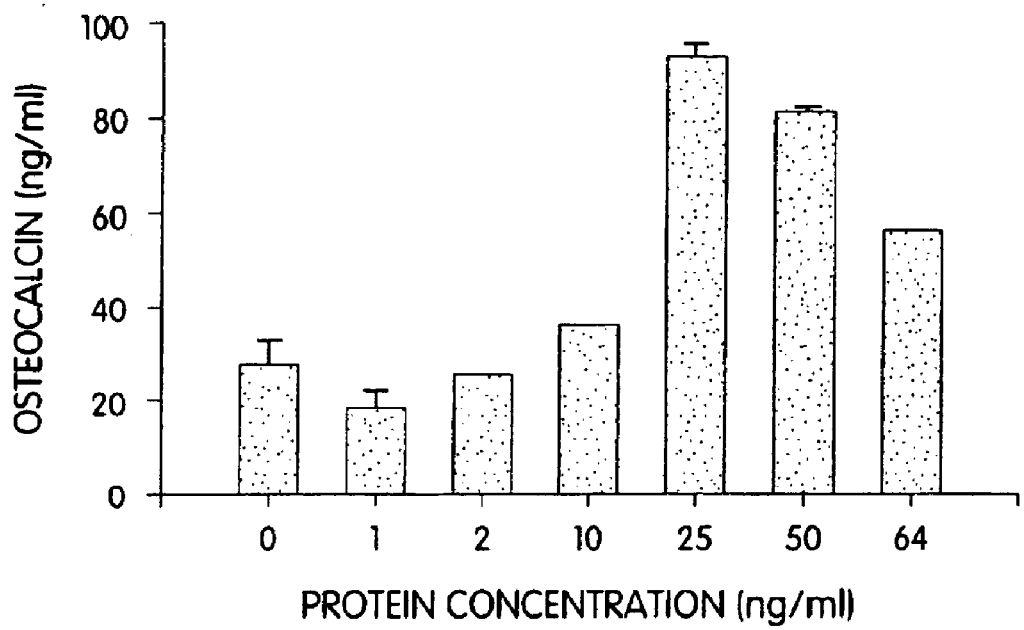
FIGS. 6A and B graphs the effect of morphogen on osteoclacin synthesis (A), and the effect of morphogen on the rate of mineralization (B)
Figure 6B:
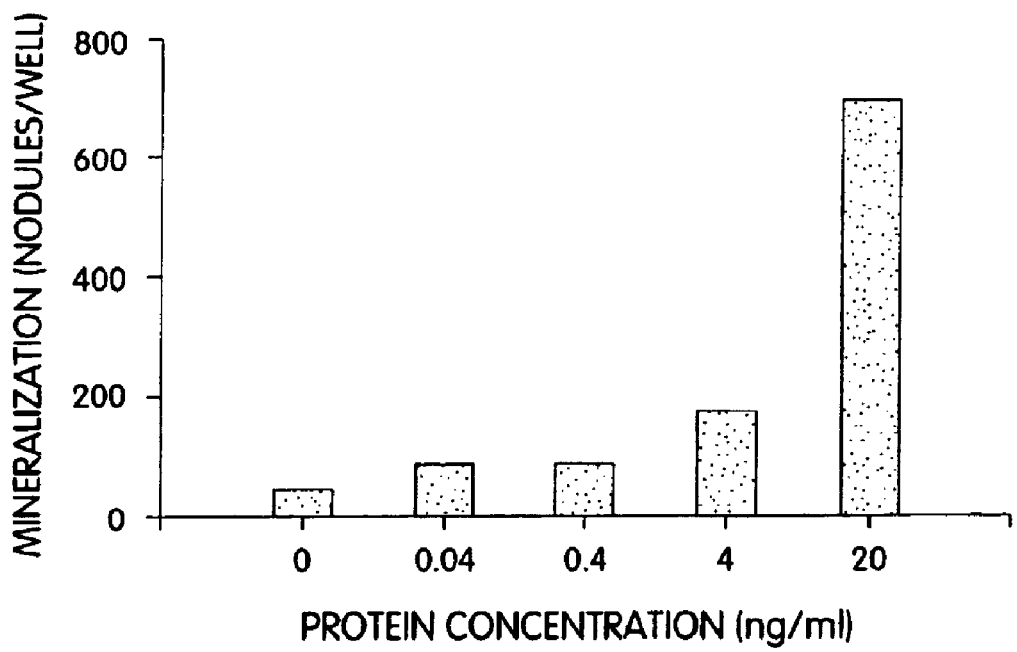

As can be seen in FIG. 6A OP-1 stimulates osteocalcin synthesis in oseoblast cultures. The increased osteocalcin synthesis in response to OP-1 is dose dependent and showed a 5-fold increase over the basal level using 25 ng of OP-1/10 ml medium after 13 days of incubation. The enhanced osteocalcin synthesis also can be confirmed by detecting the elevated osteocalcin mRNA message (20-fold increase) using a rat osteocalcin-specific probe. In addition, the increase in osteoclacin synthesis correlates with increased mineralization in long term osteoblast cultures as determined by the appearance of mineral nodules (compare FIGS. 6A and 6B.) OP-1 increases the initial mineralization rate about 20-fold compared to untreated cultures. Similar experiments performed using TGF-β indicate that TGF-β does not induce osteocalcin synthesis or promote the mineralization process. Thus, morphogen alone promotes the growth and expression of the osteoblast differentiated phenotype.

Example 7

Effect of Morphogen on Bone Derived Growth Factor Induction in vitro

IGF-I and IGF-II are bone-derived growth factors involved in coupling bone formation with bone resorption in the bone remodeling cycle. The effect of morphogen on the production of these and other bone-derived growth factors, including TGF-β, may be evaluated using the following procedure.

Rat or human osteoblasts were prepared and cultured in a multiwell plate as for Example 2. The wells of the plate were divided in to groups in which different concentrations of morphogen were added (e.g., 0, 1, 10, and 100 ng). In this example, OP-1 was the morphogen used. The plate then was incubated for a prescribed period of time, e.g., 72 hours, and the level of IGF detected, e.g., by immunolocalization, using a commercially available antibody specific for IGFs. OP-1 induced the level of both IGF-I and IGF-II significantly. Greater than six fold IGF-I and two fold IGF-II were induced following exposure to 100 ng OP-1/ml. In addition, OP-1 stimulated production of the IGF-I stimulating factor, BP3 (IGF-I binding protein 3).

Example 8

Effect of Morphogen on Trabecular Bone in Ovariectomized (OVX) Rats

As indicated above, serum alkaline phosphatase and osteocalcin levels are indicators of bone formation within an individual. In order to determine the effect of a morphogen on bone production in vivo, these parameters are measured under conditions which promote osteoporosis, e.g., wherein osteoporosis is induced by ovary removal in rats.

Forty Long-Evans rats (Charles River Laboratories, Wilmington) weighing about 200 g each are ovariectomized (OVX) using standard surgical procedures, and ten rats are sham-operated. The ovariectomization of the rats produces an osteoporotic condition within the rats as a result of decreased estrogen production. Food and water are provided ad libitum. Eight days after ovariectomy, the rats, prepared as described above, were divided into five groups: (A), 10 sham-operated rats; (B), 10 ovariectomized rats receiving 1 ml of phosphate-buffered saline (PBS) i.v. in the tail vein; (C) 10 ovariectomized rats receiving about 1 mg of $17bE_2$ (17-b-estradiol $E_2$) by intravenous injection through the tail vein; (D) 9 ovariectomized rats receiving daily injections of approximately 2 μg of morphogen by tail vein for 22 days; and (E) 9 ovariectomized rats receiving daily injections of approximately 20 μg of morphogen by tail vein for 22 days. In this example, OP-1 was the morphogen tested.

On the 15th and 21st day of the study, each rat was injected with 5 mg of tetracycline, and on day 22, the rats were sacrificed. The body weights, uterine weights, serum alkaline phosphate levels, serum calcium levels and serum osteocalcin levels then were determined for each rat. The results are shown in Tables III and IV.

TABLE III

Body Weights, Uterine Weights and Alkaline Phosphatase

| Group | Body Weights | Uterine Weights | Alk. Phosphatase |
|---|---|---|---|
| A-SHAM | 250.90 ± 17.04 | 0.4192 ± 0.10 | 43.25 ± 6.11 |
| B-OVX + PBS | 273.40 ± 16.81 | 0.1650 ± 0.04 | 56.22 ± 6.21 |
| C-OVX + E2 | 241.66 ± 21.54 | 0.3081 ± 0.03 | 62.66 ± 4.11 |
| D-OVX + OP-1 (2 μg) | 266.67 ± 10.43 | 0.1416 ± 0.03 | 58.09 ± 12.97 |
| E-OVX + OP-1 (20 μg) | 272.40 ± 20.48 | 0.1481 ± 0.05 | 66.24 ± 15.74 |

TABLE IV

Serum Calcium and Serum Osteocalcin Levels

| Group | Serum Calcium (ng/dl) | Serum Osteocalcin (ng/ml) |
| --- | --- | --- |
| A-SHAM | 8.82 ± 1.65 | 64.66 ± 14.77 |
| B-OVX + PBS | 8.95 ± 1.25 | 69.01 ± 10.20 |
| C-OVX + E2 | 9.20 ± 1.39 | 67.13 ± 17.33 |
| D-OVX + OP-1 (2 μg) | 8.77 ± 0.95 | 148.50 ± 84.11 |
| E-OVX + OP-1 (20 μg) | 8.67 ± 1.94 | 182.42 ± 52.11 |

The results presented in Table III and IV show that intravenous injection of morphogen into ovariectomized rats produces a significant increase in serum alkaline phosphatase and serum osteocalcin levels and demonstrates that systemic administration of the morphogen stimulates bone formation in osteoporotic bone.

Example 9

Histomorphometric Analysis of Morphogen on the Tibia Diaphysis in Ovariectomized (OVX) Rats Fifteen female Long-Evans rats weighing about 160 g were ovariectomized (OVX) to produce an osteoporotic condition and five rats were sham operated (Charles River Laboratories, Wilmington, Mass.) as described for Example 8. Food and water were provided ad libitum. Twenty-two days after ovariectomy, the rats were divided into four groups: (A) sham-operated (1 ml of PBS by intravenous injection through tail vein (5 rats); (B) OVX, into which nothing was injected (5 rats); (C) OVX, receiving about 1 mg of 17bE$_2$ by intravenous injection through the tail vein (5 rats), and (D) OVX, receiving about 1 μg of morphogen by intravenous injection through the tail vein (5 rats). In this example, OP-1 was morphogen tested.

The rats were injected daily as described for seven days, except no injections were given on the thirteenth day. The rats then were sacrificed on the nineteenth day. The tibial diaphyseal long bones then were removed and fixed in ethanol and histomorphometric analysis was carried out using standard procedures well known in the art. The results are shown in Table V.

TABLE V

| MEASUREMENT | (A) CONTROL | (B) OVX | (C) OVX + E$_2$ | (D) OVX + OP-1 |
| --- | --- | --- | --- | --- |
| Longitudinal Growth Rate (μm/day) | 20.2 ± 0.3 | 19.4 ± 0.2 | 4.9 ± 0.5 | 17.9 ± 0.9 |
| Cancellous Bone Volume (BV/TV, bone vol/total vol) | 20.2 ± 1.5 | 13.0 ± 1.6 | 13.7 ± 2.1 | 16.6 ± 1.8 |
| Cancellous Bone Perimeter (μm) | 16.2 ± 1.8 | 9.6 ± 0.9 | 11.5 ± 1.1 | 12.2 ± 0.7 |
| Labeled Cancellous Perimeter (%) | 35.5 ± 1.5 | 51.9 ± 5.6 | 58.0 ± 4.2 | 39.2 ± 1.9 |
| Mineral Apposition Rate (μm/day) | 1.76 ± 0.14 | 2.25 ± 0.16 | 1.87 ± 0.08 | 1.86 ± 0.20 |

The results presented in Table V confirm the results of Example 8, that intravenous injection of OP-1 into ovariectomized rats stimulates bone growth for bone which had been lost due to the drop in estrogen within the individual rat. Specifically, the inhibition of cancellous bone volume in OVX rats is repaired by the systemically provided morphogen. In addition, in morphogen-treated rats the labelled cancellous perimeter and mineral apposition rate now return to levels measured in the control, sham-operated rats. Moreover, morphogen treatment does not inhibit longitudinal bone growth, unlike estrogen treatment, which appears to inhibit bone growth significantly. Accordingly, systemic administration of a morphogen in therapeutically effective concentrations effectively inhibits loss of bone mass in a mammal without inhibiting natural bone formation.

Example 10

Determination of the Presence of Morphogen in Body Fluids

OP-1 has been identified in saliva, human blood serum, and various milk forms, including mammary gland extract, colostrum, and 57-day bovine milk. Moreoever, as described below, the body fluid extracted protein is morphogenically active. The discovery that the morphogen naturally is present in milk, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, indicates that the protein plays a significant role in tissue development, including skeletal development of juveniles (see Example 13, below).

10.1 Morphogen Detection in Milk

OP-1 was partially purified from rat mammary gland extract and bovine colostrum and 57 day milk by passing these fluids over a series of chromatography columns: (e.g., cation-exchange, affinity and reverse phase). At each step the eluant was collected in fractions and these were tested for the presence of OP-1 by standard immunoblot. Immunoreactive fractions then were combined and purified further. The final, partially purified product then was examined for the presence of OP-1 by Western blot analysis using OP-1-specific antisera, and tested for in vivo and in vitro activity.

OP-1 purified from the different milk sources were characterized by Western blotting using antibodies raised against OP-1 and BMP2. Antibodies were prepared using standard immunology protocols well known in the art, and as described generally in Example 14, below, using full-length *E. coli*-produced OP-1 and BMP2 as the immunogens.

Figure 7:
FIG. 7 shows Western Blot analysis of bovine colostrum using OP-1 and BMP2-specific antibodies.

As shown in FIG. 7 OP-1 purified from colostrum reacts with the anti-OP-1 antibody, but not with anti-BMP2 antibody. In FIG. 7 lane 1 contains reduced, purified, recombinantly-produced OP-1; lane 2 contains purified bovine colostrum, and lane 3 contains reduced COP-16, a biosynthetic contruct having morphogenic activity and an amino acid sequence modeled on the proteins described herein, but having highest amino acid sequence homology with BMP2 (see U.S. Pat. No. 5,011,691 for the COP-16 amino acid sequence.) In FIG. 7A the gel was probed with anti-OP-1 antibody; in FIG. 17B, the gel was probed with anti-BMP2 antibody. As can be seen in the figure, anti-OP-1 antibody hybridizes only with protein in lanes 1 and 2, but not 3; while anti-BMP2 antibody hybridizes with lane 3 only.

Column-purified mammary gland extract and 57-day milk also reacts specifically with anti-OP-1 antibodies, including antibody raised against the full length E. coli OP-1, full length mammalian-produced OP-1, and the OP-1 Ser-17-Cys peptide (e.g., the OP-1 N-terminal 17 amino acids).

The morphogenic activity of OP-1 purified from mammary gland extract was evaluated in vivo as follows. A sample was prepared from each OP-1 immunoreactive fraction of the mammary gland extract-derived OP-1 final product by lyophilizing a portion (33%) of the fraction and resuspending the protein in 220 μl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation.

Figure 8A:
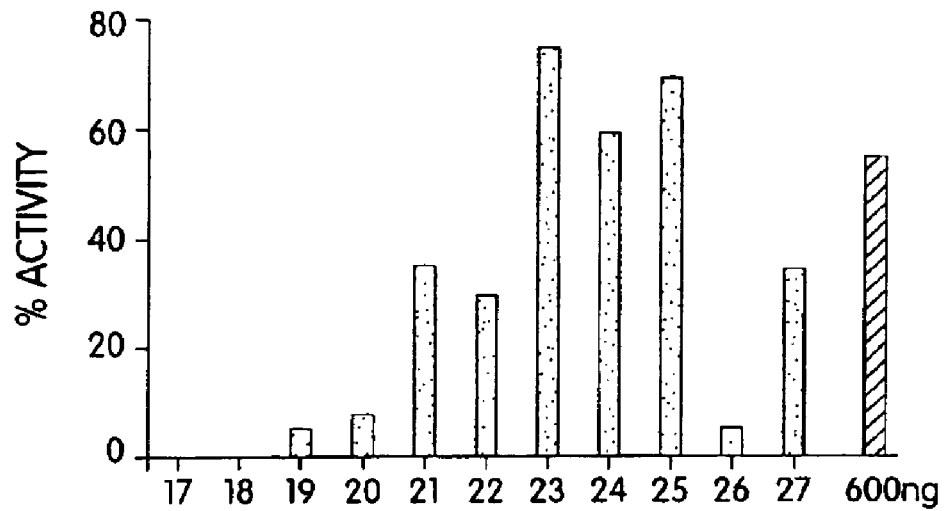
FIGS. 8A and B show results of in vivo and in vitro activity assays, respectively, for mammary extract purified OP-1.

The results are presented in FIG. 8A, where "% activity" refers to the percent of bone formation/total area covered by bone in the histology sample. In the figure, solid bars represent implants using mammary extract-derived OP-1, each bar corresponding to an immunoreactive fraction of the purified product, the fraction number being indicated on the x-axis. The hatched bar represents an implant using recombinantly produced OP-1 (600 ng). As can be seen in the figure, all immunoreactive fractions are osteogenically active.

Figure 8B:
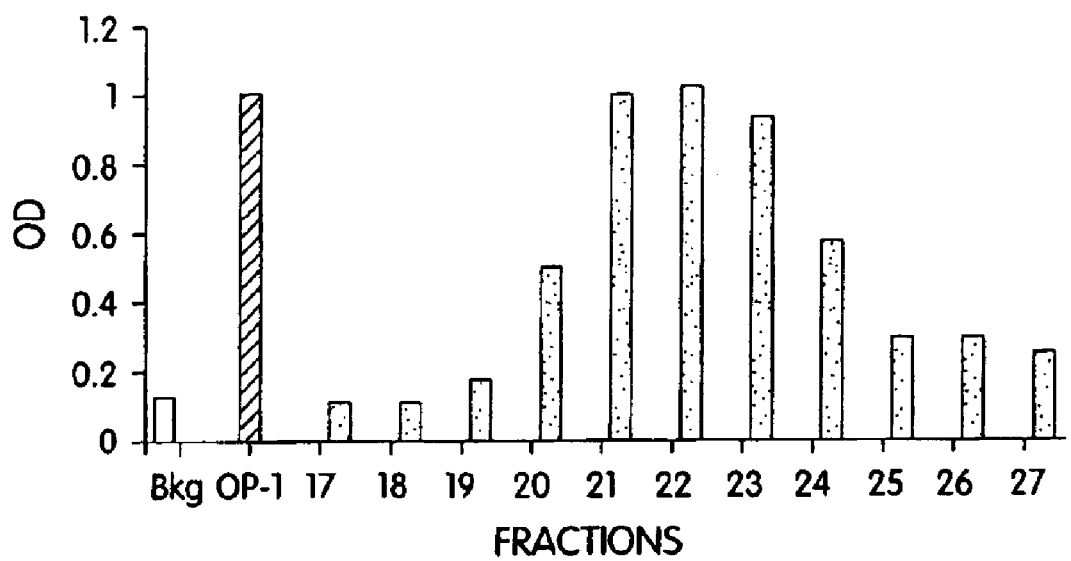

Similarly, the morphogenic activity of OP-1 purified from mammary gland extract was evaluated in vitro by measuring alkaline phosphatase activity in vitro using the following assay. Test samples were prepared as for the in vivo assay, using 15–20% of individual immunoreactive fractions collected from the final product. Alkaline phosphatase activity was tested as described above in Example 4. The results, presented in FIG. 8B, indicate that the immunoreactive fractions can stimulate alkaline phosphatase activity in vitro. Moreover, the activity correlates well with that produced by highly purified, recombinantly produced, OP-1. In FIG. 8B solid bars represent assays performed with mammary gland-purified OP-1, each bar corresponding to an immunoreactive fraction of column-purified OP-1, the fraction numbers being indicated on the x-axis; the hatched bar represents the assay performed with purified, recombinantly-produced OP-1 (100 ng ml); and the cross-hatched bar represents background.

10.2 Morphogen Detection in Serum

Morphogen may be detected in serum using morphogen-specific antibodies. The assay may be performed using any standard immunoassay, such as Western blot (immunoblot) and the like. Preferably, the assay is performed using an affinity column to which the morphogen-specific antibody is bound and through which the sample serum then is poured, to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and the results confirmed by N-terminal sequencing. Preferably, the affinity column is prepared using monoclonal antibodies. Morphogen concentrations in serum or other fluid samples then may be determined using standard protein quantification techniques, including by spectrophotometric absorbance or by quantitation of conjugated antibody.

Presented below is a sample protocol for identifying OP-1 in serum. Following this general methodology other morphogens may be detected in body fluids, including serum. The identification of morphogen in serum further indicates that systemic administration is a suitable means for providing therapeutic concentrations of a morphogen to an individual, and that morphogens likely behave systemically as endocrine-like factors. Finally, using this protocol, fluctuations in endogenous morphogen levels can be detected, and these altered levels may be used as an indicator of bone tissue dysfunction. Alternatively, fluctuations in morphogen levels may be assessed by monitoring morphogen transcription levels, either by standard northern blot analysis as described in Example 1, or by in situ hybridization, using a labelled probe capable of hybridizing specifically to morphogen RNA, and standard RNA hybridization protocols well described in the art and described generally in Example 1.

Figure 9:
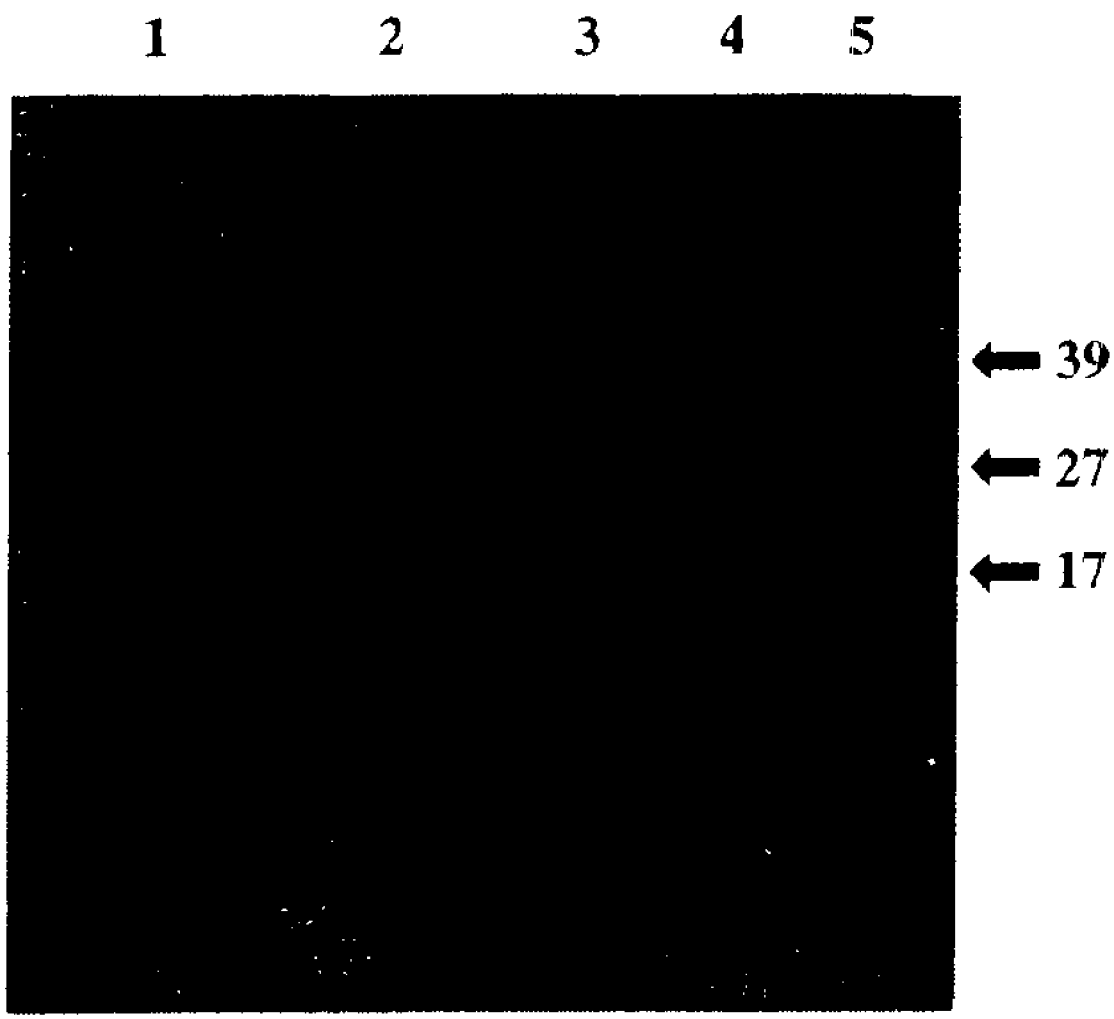
FIG. 9 is a photomicrograph of an immunoblot showing the presence of hOP-1 in serum.

OP-1 was detected in human serum using the following assay. A monoclonal antibody raised against mammalian, recombinantly produced OP-1 using standard immunology techniques well described in the art and described generally in Example 14, was immobilized by passing the antibody over an agarose-activated gel (e.g., Affi-Gel™, from Bio-Rad Laboratories, Richmond, Calif., prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP-1 by standard immunoblot using an OP-1 specific antibody as for Example 10.A. FIG. 9 is an immunoblot showing OP-1 in human sera under reducing and oxidized conditions. In the figure, lanes 1 and 4 are OP-1 standards, run under oxidized (lane 1) and reduced (lane 4) conditions. Lane 5 shows molecular weight markers at 17, 27 and 39 kDa. Lanes 2 and 3 are human sera OP-1, run under oxidized (lane 2) and reduced (lane 3) conditions.

Morphogens may be used in diagnostic applications by comparing the quantity of morphogen present in a body fluid sample with a predetermined reference value, with fluctuations in fluid morphogen levels indicating a change in the status of bone tissue. Alternatively, fluctuations in the level of endogenous morphogen antibodies may be detected by this method, most likely in serum, using an antibody or other binding protein capable of interacting specifically with the endogenous morphogen antibody. Detected fluctuations in the levels of the endogenous antibody may be used as indicators of a change in tissue status.

Example 11

Morphogen-Induced Periosteal and Endosteal Bone Formation

Osteoclast-induced bone resorption occurs primarily at the endosteal surface of bone tissue. Accordingly, in bone remodeling disorders the marrow cavity is enlarged unnaturally, weakening the weight bearing capacity of the remaining bone. The following example provides means for evaluating the ability of the morphogens described herein to increase endosteal and preiosteal bone mass in a mammal. In this example, both periosteal and endosteal bone formation are induced by direct injection of a morphogen in a biocompatible solution directly to the bone tissue. As demonstrated below, morphogens can induce new bone formation and increase bone mass at both surfaces when provided to the bone by direct injection. Direct injection may be a preferred mode of administration for providing therapeutically effective concentrations to reduce an enlarged marrow cavity, and/or to repair fractures and other damage to bone tissue microstructure.

Figure 10A:
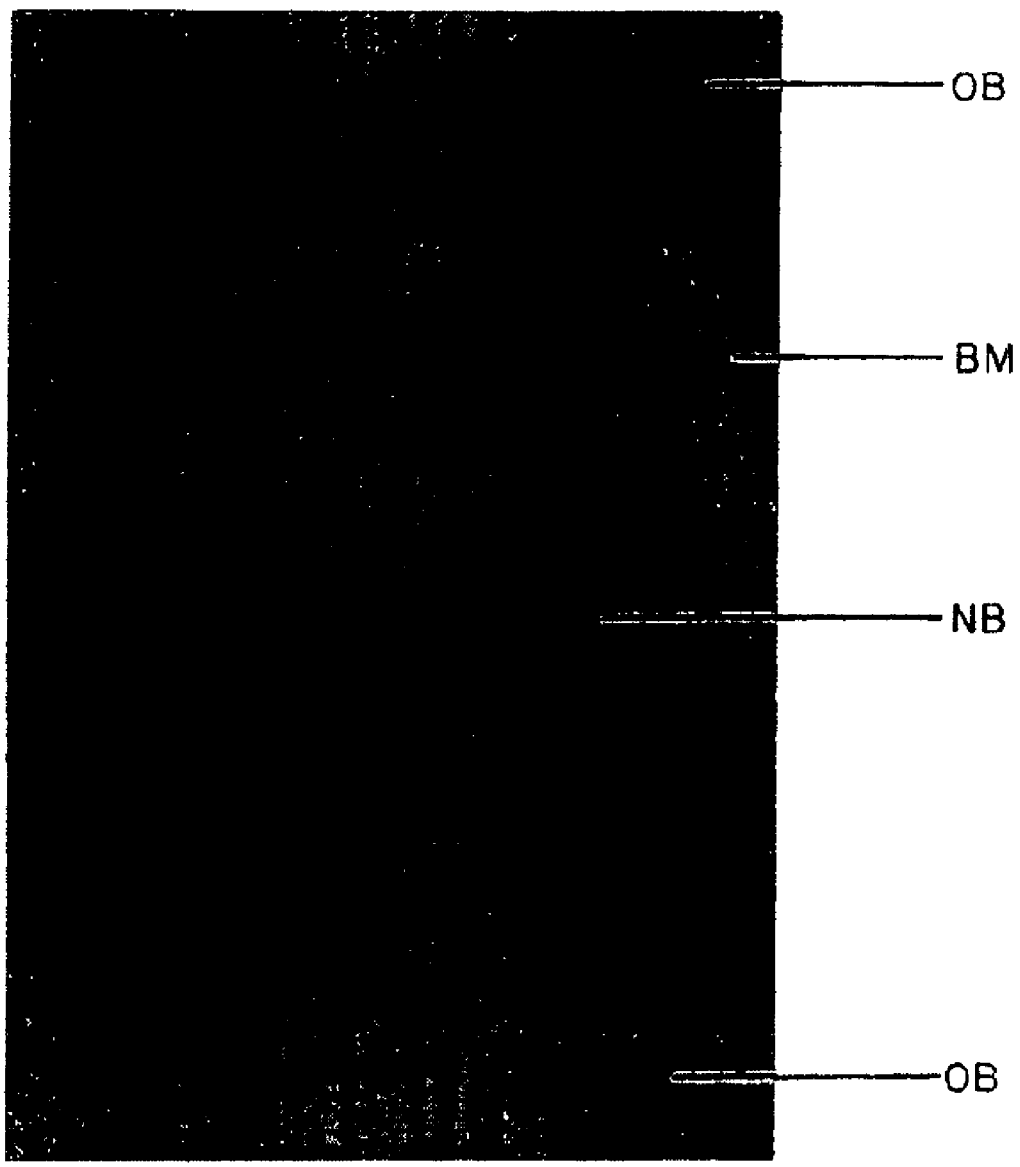
FIGS. 10(A and B) are photomicrographs showing new endosteum bone formation following morphogen injection onto the endosteal surface (A), and new periosteum bone formation following morphogen injection onto the periosteal surface (B)
Figure 10B:
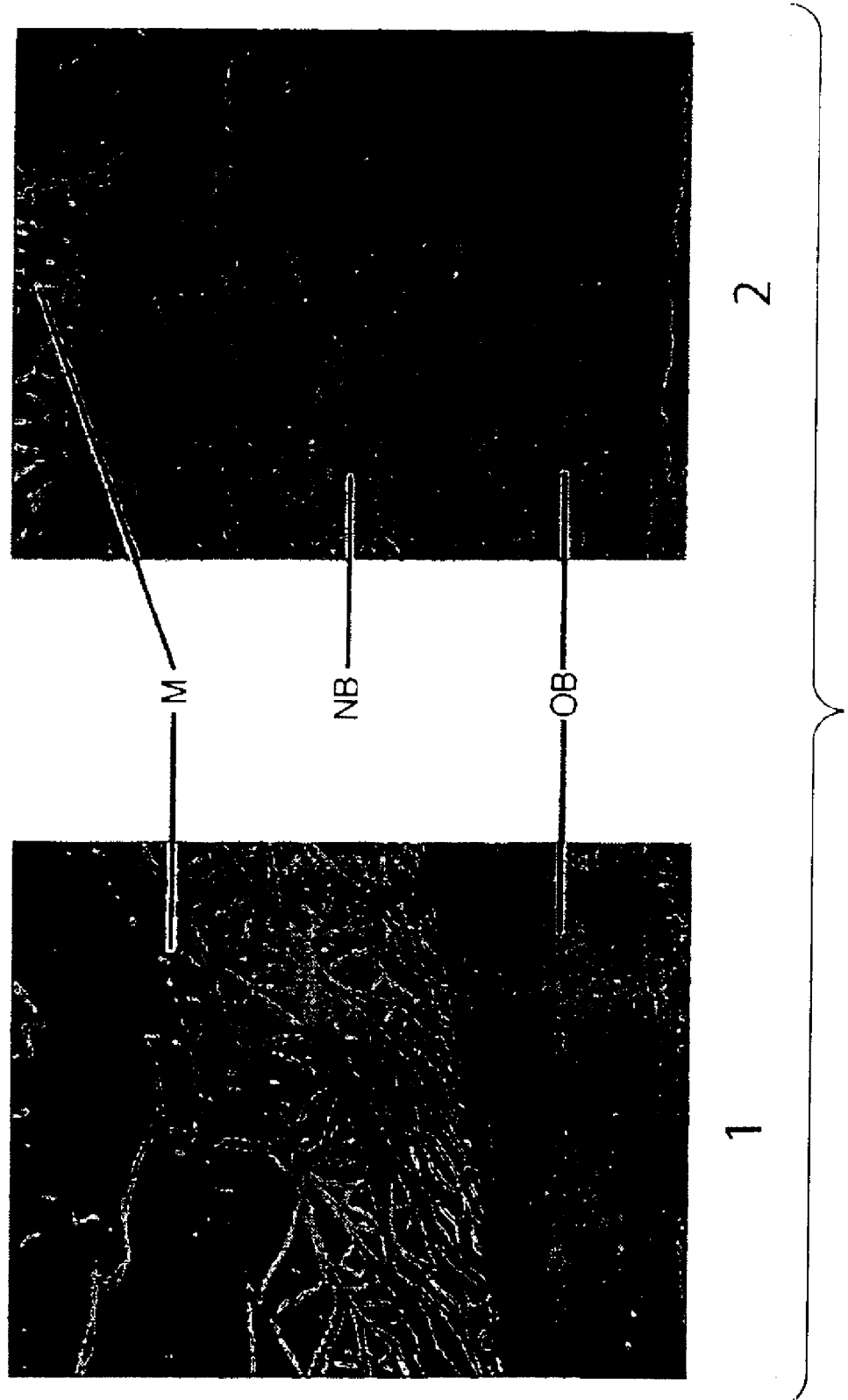

Morphogen was provided to either the periosteum (outer or peripheral bone surface) and endosteum (interior bone surface, e.g., that surface lining the marrow cavity) of a rat femur by a single injection in each case. Specifically, morphogen (e.g., OP-1, 2–20 µg) was provided to the bone tissue as an insoluble colloidal suspension in phosphate-buffered saline. Endosteal injection was performed through a microhole made with a hand-held orthopedic drill. After 7 days, the treated bones were removed and prepared for histological evaluation as described in U.S. Pat. No. 4,968,590. As little as 2 µg morphogen is sufficient to induce new bone formation at the site of injection within 4–7 days. In addition, bone induction is dose-dependent. Photomicrographs of the histology are presented in FIG. 10. In the figure, "ob" means old bone, "bm" means bone marrow, "nb" means new bone, and "m" means muscle. FIG. 10A shows new bone formed following injection of morphogen to the endosteal surface. As can be seen in the figure, new bone has formed within the bone marrow cavity, filling in the periphery of the cavity. FIG. 10B shows new bone formed following injection of morphogen to the periosteal surface, replacing the muscle normally present.

Example 12

Effect of Morphogen on Bone Resorption

The effect of morphogen on bone resorption may be evaluated using rat osteoclasts on bovine bone slices, in the presence and absence of morphogen, and the effect of morphogen on pit formation (resorption index) determined. Under standard conditions rat osteoclasts begin resorbing the bone tissue, causing pit formation on the bone slice surface. In this experiment OP-1 was the morphogen tested, at concentrations of 0, 5, 10, 20, 40, 50, and 100 ng/ml.

Figure 11:
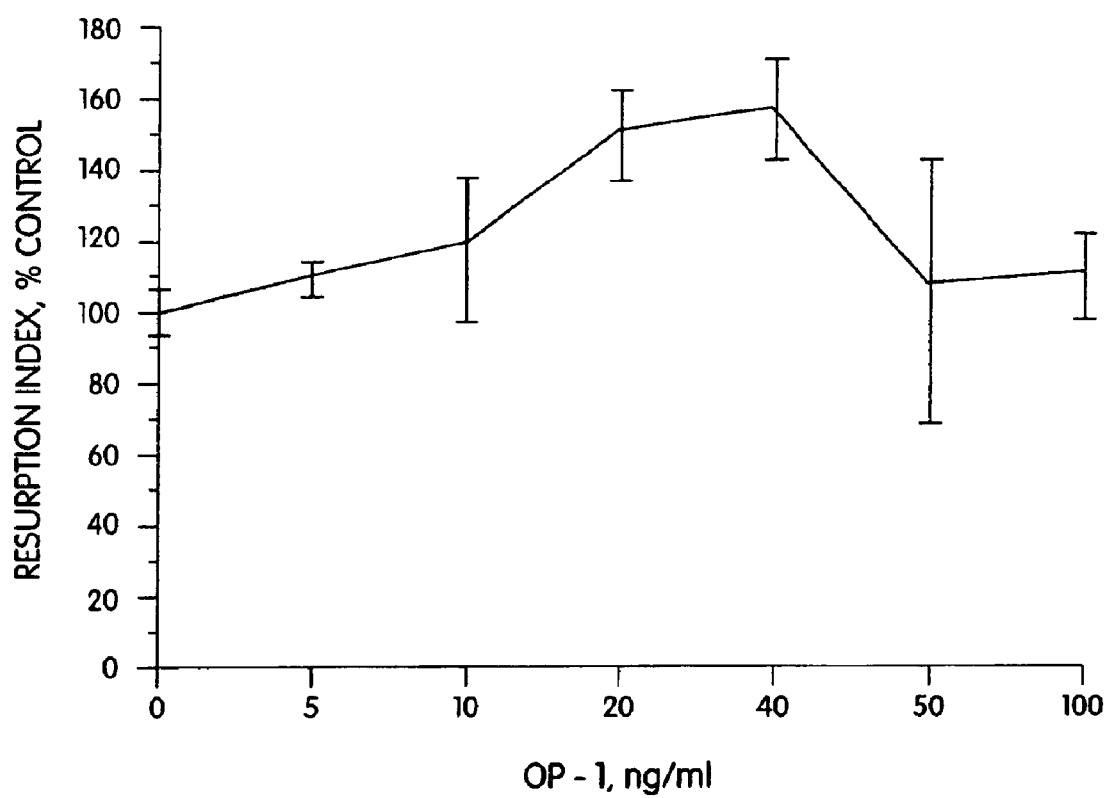
FIG. 11 is a graphic representation of the dose-dependent effect of morphogen on bone resorption.

The results are presented in FIG. 11, where the resorption index is calculated as a percent of the control (e.g., bone resorption in the absence of morphogen), calculated as the number of pits per a given slice surface area. Below 40 ng bone resorption is enhanced; above 40 ng, OP-1 has no apparent effect on bone resorption. The results highlight the integral role the morphogen plays in bone remodeling. OP-1 is stored in bone tissue in vivo. In a normal bone remodeling cycle, the local concentration of OP-1 at the surface likely is low when osteoclasts begin resorbing bone, and the low concentration may enhance and/or stimulate bone resorption. As resorption continues, the local concentration of OP-1 at the surface likely increases, to a concentration that no longer has an effect on osteoclasts, but continues to affect osteoblast growth and activity (see Examples 2–7), stimulating bone growth.

Figure 12B:
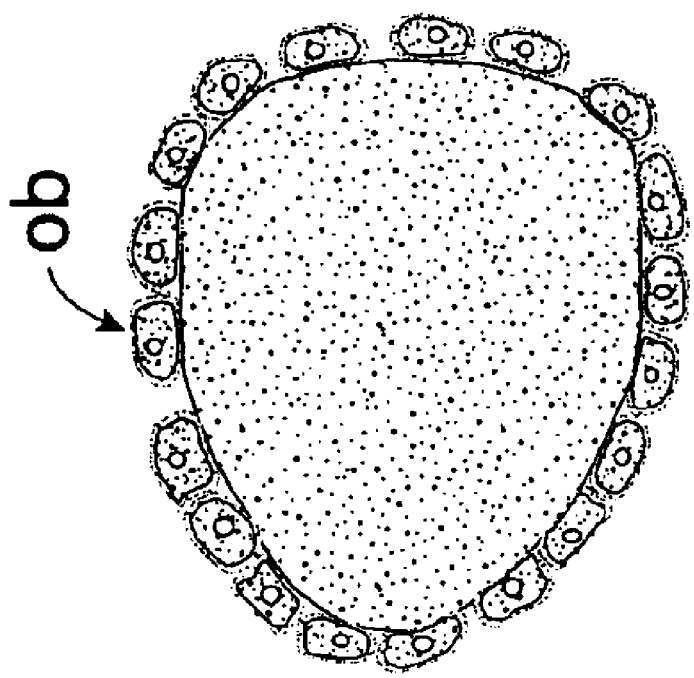
FIGS. 12(A and B) are schematic representations of morphogen inhibition of early mononuclear phagocytic cell multinuclearization in vivo.
Figure 12A:
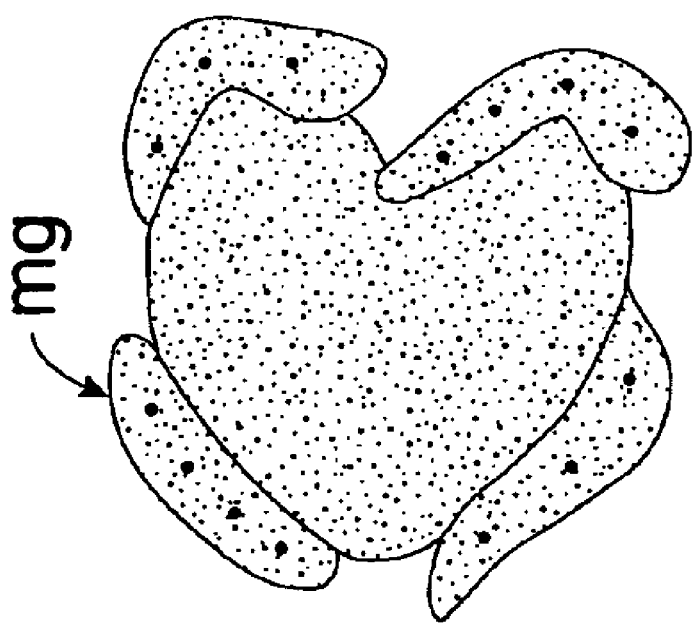

In addition, morphogens can inhibit multinucleation of mononuclear phagocytic cells under conditions where these cells normally would be activated. For example, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. FIG. 12 illustrates this effect of morphogens, in a schematic representation of histology results of a titanium oxide substrate implanted subcutaneously. In the figure, "mg" means mononuclear giant cells and "ob" means osteoblasts. The substrate represented in FIG. 12B was implanted together with morphogen (OP-1) and newly formed osteoblasts are evident surrounding the substrate. By contrast, the substrate represented in FIG. 12A was implanted without morphogen and extensive multinucleated giant cell formation is evident surrounding the substrate. Accordingly, the morphogens' effect in inhibiting excessive bone mass loss in a mammal also may include inhibiting activation of these cells.

Example 13

Effect of Morphogen Neutralization on Bone Growth

The effect of the morphogens described herein on bone growth in developing mammals also may be evaluated using neutralizing antibodies specific for particular morphogens and assessing the effect of these antibodies on bone development. Specifically, anti-morphogen monoclonal and/or polyclonal antibodies may be prepared using standard methodologies including, for example, the protocol provided in Example 14, below.

Purified antibodies then are provided regularly to new born mice, e.g., 10–100 µg/injection/day for 10–15 days. At 10 or 21 days, the mice are sacrificed and the effect of morphogen on bone development assessed by body weight, gross visual examination and histology. In this example, anti-OP-1 antibodies were used. Morphogen neutralization significantly stunted body growth, including bone growth, as indicated by the reduced body weight and reduced bone length of the treated mammals.

Similarly, morphogen activity may be assessed in fetal development in the mouse model using the following assay. Single lip injections comprising _10–100 µg/injection of morphogen-specific antibody are administered to pregnant female mice during each day of the gestation period and bone development in treated and control new mice evaluated by standard histomorphometric analysis at birth. Similarly, single lip injections also may be provided to juvenile and adult mice (e.g., 10–100 µg) over a prolonged time (e.g., 10–15 days) to evaluate the effect on bone growth and bone integrity and to evaluate the onset of osteoporosis. The antibodies are anticipated to inhibit tissue morphogenesis, including bone growth and bone development, in the developing embryos.

Example 14

Screening Assay for Candidate Compounds which Alter Endogenous Morphogen Levels

Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A detailed description also may be found in U.S. Ser. No. 752,861, incorporated hereinabove by reference.

14.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for morphogen production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo morphogen synthesis, some cultures are labeled according to conventional procedures with an $^{35}$S-methionine/$^{35}$S-cysteine mixture for 6–24 hours and then evaluated for morphogenic protein synthesis by conventional immunoprecipitation methods.

14.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 µg/100 µl of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant is added to each well in triplicate and incubated at 37° C. for 30 min. After incubation, 100 µl biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1 Tween 20. 100 µl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 µl substrate (ELISA Amplification System Kit, Life Technologies, Inc., Bethesda, Md.) is added to each well incubated at room temperature for 15 min. Then, 50 µl amplifier (from the same amplification system kit) is added and incubated for another 15 min at room temperature. The reaction is stopped by the addition of 50 µl 0.3 M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 ug/500 µl $E.$ $coli$-produced OP-1 monomer (amino acids 328–431 in SEQ ID NO:5) in 0.1% SDS mixed with 500 µl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 µg of antigen and bled (15 ml per bleed) at days seven and ten after boosting.

Monoclonal antibody specific for a given morphogen may be prepared as follows. A mouse is given two injections of $E. coli$ produced OP-1 monomer. The first injection contains 100 µg of OP-1 in complete Freund's adjuvant and is given subcutaneously. The second injection contains 50 µg of OP-1 in incomplete adjuvant and is given intraperitoneally. The mouse then receives a total of 230 µg of OP-1 (amino acids 307–431 in SEQ ID NO:5) in four intraperitoneal injections at various times over an eight month period. One week prior to fusion, both mice are boosted intraperitoneally with 100 µg of OP-1 (307–431) and 30 µg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to commercially available myeloma cells at a ratio of 1:1 using PEG 1500 (Boeringer Mannheim, Germany), and the cell fusion is plated and screened for OP-1-specific antibodies using OP-1 (307–431) as antigen. The cell fusion and monoclonal screening then are according to standard procedures well described in standard texts widely available in the art.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

SEQUENCE LISTING

<160> NUMBER OF SEQ ID NOS: 33

<210> SEQ ID NO 1
<211> LENGTH: 97
<212> TYPE: PRT
<213> ORGANISM: Artificial Sequence
<220> FEATURE:
<223> OTHER INFORMATION: Generic Sequence 1
<220> FEATURE:
<221> NAME/KEY: MISC_FEATURE
<222> LOCATION: (1)..(97)
<223> OTHER INFORMATION: Xaa=one of the 20 naturally-occurring L-isomer,
      a-amino acids or a derivative thereof

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa

<210> SEQ ID NO 2
<211> LENGTH: 97
<212> TYPE: PRT
<213> ORGANISM: Artificial Sequence
<220> FEATURE:
<223> OTHER INFORMATION: Generic Sequence 2
<220> FEATURE:
<221> NAME/KEY: MISC_FEATURE
<222> LOCATION: (1)..(97)
<223> OTHER INFORMATION: Xaa=one of the 20 naturally-occurring L-isomer,
      a-amino acids or a derivative thereof

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa

<210> SEQ ID NO 3
<211> LENGTH: 97
<212> TYPE: PRT
<213> ORGANISM: Artificial Sequence

```
<220> FEATURE:
<223> OTHER INFORMATION: Generic Sequence 3
<220> FEATURE:
<221> NAME/KEY: MISC_FEATURE
<222> LOCATION: (4)
<223> OTHER INFORMATION: Xaa=Ser, Asp or Glu
<220> FEATURE:
<221> NAME/KEY: MISC_FEATURE
<222> LOCATION: (6)
<223> OTHER INFORMATION: Xaa=Arg, Gln, Ser, or Lys
<220> FEATURE:
<221> NAME/KEY: MISC_FEATURE
<222> LOCATION: (7)
<223> OTHER INFORMATION: Xaa=Asp or Glu
<220> FEATURE:
<221> NAME/KEY: MISC_FEATURE
<222> LOCATION: (8)
<223> OTHER INFORMATION: Xaa=Leu or Val
<220> FEATURE:
<221> NAME/KEY: MISC_FEATURE
<222> LOCATION: (11)
<223> OTHER INFORMATION: Xaa=Gln, Leu, Asp, His, or Asn
<220> FEATURE:
<221> NAME/KEY: MISC_FEATURE
<222> LOCATION: (12)
<223> OTHER INFORMATION: Xaa=Asp, Arg or Asn
<220> FEATURE:
<221> NAME/KEY: MISC_FEATURE
<222> LOCATION: (14)
<223> OTHER INFORMATION: Xaa=Ile or Val
<220> FEATURE:
<221> NAME/KEY: MISC_FEATURE
<222> LOCATION: (15)
<223> OTHER INFORMATION: Xaa=Ile or Val
<220> FEATURE:
<221> NAME/KEY: MISC_FEATURE
<222> LOCATION: (19)
<223> OTHER INFORMATION: Xaa=Glu, Gln, Leu, Lys, Pro, or Arg
<220> FEATURE:
<221> NAME/KEY: MISC_FEATURE
<222> LOCATION: (20)
<223> OTHER INFORMATION: Xaa=Tyr or Phe
<220> FEATURE:
<221> NAME/KEY: MISC_FEATURE
<222> LOCATION: (21)
<223> OTHER INFORMATION: Xaa=Ala, Ser, Asp, Met, His, Leu, or Gln
<220> FEATURE:
<221> NAME/KEY: MISC_FEATURE
<222> LOCATION: (23)
<223> OTHER INFORMATION: Xaa=Tyr, Asn or Phe
<220> FEATURE:
<221> NAME/KEY: MISC_FEATURE
<222> LOCATION: (26)
<223> OTHER INFORMATION: Xaa=Glu, His, Tyr, Asp, or Gln
<220> FEATURE:
<221> NAME/KEY: MISC_FEATURE
<222> LOCATION: (28)
<223> OTHER INFORMATION: Xaa=Glu, Lys, Asp, or Gln
<220> FEATURE:
<221> NAME/KEY: MISC_FEATURE
<222> LOCATION: (30)
<223> OTHER INFORMATION: Xaa=Ala, Ser, Pro, or Gln
<220> FEATURE:
<221> NAME/KEY: MISC_FEATURE
<222> LOCATION: (31)
<223> OTHER INFORMATION: Xaa=Phe, Leu or Tyr
<220> FEATURE:
<221> NAME/KEY: MISC_FEATURE
<222> LOCATION: (33)
<223> OTHER INFORMATION: Xaa=Leu or Val
<220> FEATURE:
<221> NAME/KEY: MISC_FEATURE
<222> LOCATION: (34)
<223> OTHER INFORMATION: Xaa=Asn, Asp, Ala, or Thr
<220> FEATURE:
<221> NAME/KEY: MISC_FEATURE
<222> LOCATION: (35)
<223> OTHER INFORMATION: Xaa=Ser, Asp, Glu, Leu, or Ala
<220> FEATURE:
```

```
<221> NAME/KEY: MISC_FEATURE
<222> LOCATION: (36)
<223> OTHER INFORMATION: Xaa=Tyr, Cys, His, Ser, or Ile
<220> FEATURE:
<221> NAME/KEY: MISC_FEATURE
<222> LOCATION: (37)
<223> OTHER INFORMATION: Xaa=Met, Phe, Gly, or Leu
<220> FEATURE:
<221> NAME/KEY: MISC_FEATURE
<222> LOCATION: (38)
<223> OTHER INFORMATION: Xaa=Asn or Ser
<220> FEATURE:
<221> NAME/KEY: MISC_FEATURE
<222> LOCATION: (39)
<223> OTHER INFORMATION: Xaa=Ala, Ser or Gly
<220> FEATURE:
<221> NAME/KEY: MISC_FEATURE
<222> LOCATION: (40)
<223> OTHER INFORMATION: Xaa=Thr, Leu or Ser
<220> FEATURE:
<221> NAME/KEY: MISC_FEATURE
<222> LOCATION: (44)
<223> OTHER INFORMATION: Xaa=Ile or Val
<220> FEATURE:
<221> NAME/KEY: MISC_FEATURE
<222> LOCATION: (45)
<223> OTHER INFORMATION: Xaa=Val or Leu
<220> FEATURE:
<221> NAME/KEY: MISC_FEATURE
<222> LOCATION: (46)
<223> OTHER INFORMATION: Xaa=Gln or Arg
<220> FEATURE:
<221> NAME/KEY: MISC_FEATURE
<222> LOCATION: (47)
<223> OTHER INFORMATION: Xaa=Thr, Ala or Ser
<220> FEATURE:
<221> NAME/KEY: MISC_FEATURE
<222> LOCATION: (49)
<223> OTHER INFORMATION: Xaa=Val or Met
<220> FEATURE:
<221> NAME/KEY: MISC_FEATURE
<222> LOCATION: (50)
<223> OTHER INFORMATION: Xaa=His or Asn
<220> FEATURE:
<221> NAME/KEY: MISC_FEATURE
<222> LOCATION: (51)
<223> OTHER INFORMATION: Xaa=Phe, Leu, Asn, Ser, Ala, or Val
<220> FEATURE:
<221> NAME/KEY: MISC_FEATURE
<222> LOCATION: (52)
<223> OTHER INFORMATION: Xaa=Ile, Met, Asn, Ala, or Val
<220> FEATURE:
<221> NAME/KEY: MISC_FEATURE
<222> LOCATION: (53)
<223> OTHER INFORMATION: Xaa=Asn, Lys, Ala, or Glu
<220> FEATURE:
<221> NAME/KEY: MISC_FEATURE
<222> LOCATION: (54)
<223> OTHER INFORMATION: Xaa=Pro or Ser
<220> FEATURE:
<221> NAME/KEY: MISC_FEATURE
<222> LOCATION: (55)
<223> OTHER INFORMATION: Xaa=Glu, Asp, Asn, or Gly
<220> FEATURE:
<221> NAME/KEY: MISC_FEATURE
<222> LOCATION: (56)
<223> OTHER INFORMATION: Xaa=Thr, Ala, Val, Lys, Asp, Tyr, Ser, or Ala
<220> FEATURE:
<221> NAME/KEY: MISC_FEATURE
<222> LOCATION: (57)
<223> OTHER INFORMATION: Xaa=Val, Ala or Ile
<220> FEATURE:
<221> NAME/KEY: MISC_FEATURE
<222> LOCATION: (58)
<223> OTHER INFORMATION: Xaa=Pro or Asp
<220> FEATURE:
<221> NAME/KEY: MISC_FEATURE
<222> LOCATION: (59)
<223> OTHER INFORMATION: Xaa=Lys or Leu
```

```
<220> FEATURE:
<221> NAME/KEY: MISC_FEATURE
<222> LOCATION: (60)
<223> OTHER INFORMATION: Xaa=Pro or Ala
<220> FEATURE:
<221> NAME/KEY: MISC_FEATURE
<222> LOCATION: (63)
<223> OTHER INFORMATION: Xaa=Ala or Val
<220> FEATURE:
<221> NAME/KEY: MISC_FEATURE
<222> LOCATION: (65)
<223> OTHER INFORMATION: Xaa=Thr or Ala
<220> FEATURE:
<221> NAME/KEY: MISC_FEATURE
<222> LOCATION: (66)
<223> OTHER INFORMATION: Xaa=Gln, Lys, Arg, or Glu
<220> FEATURE:
<221> NAME/KEY: MISC_FEATURE
<222> LOCATION: (67)
<223> OTHER INFORMATION: Xaa=Leu, Met or Val
<220> FEATURE:
<221> NAME/KEY: MISC_FEATURE
<222> LOCATION: (68)
<223> OTHER INFORMATION: Xaa=Asn, Ser or Asp
<220> FEATURE:
<221> NAME/KEY: MISC_FEATURE
<222> LOCATION: (69)
<223> OTHER INFORMATION: Xaa=Ala, Pro or Ser
<220> FEATURE:
<221> NAME/KEY: MISC_FEATURE
<222> LOCATION: (70)
<223> OTHER INFORMATION: Xaa=Ile, Thr or Val
<220> FEATURE:
<221> NAME/KEY: MISC_FEATURE
<222> LOCATION: (71)
<223> OTHER INFORMATION: Xaa=Ser or Ala
<220> FEATURE:
<221> NAME/KEY: MISC_FEATURE
<222> LOCATION: (72)
<223> OTHER INFORMATION: Xaa=Val or Met
<220> FEATURE:
<221> NAME/KEY: MISC_FEATURE
<222> LOCATION: (74)
<223> OTHER INFORMATION: Xaa=Tyr or Phe
<220> FEATURE:
<221> NAME/KEY: MISC_FEATURE
<222> LOCATION: (75)
<223> OTHER INFORMATION: Xaa=Phe, Tyr or Leu
<220> FEATURE:
<221> NAME/KEY: MISC_FEATURE
<222> LOCATION: (76)
<223> OTHER INFORMATION: Xaa=Asp or Asn
<220> FEATURE:
<221> NAME/KEY: MISC_FEATURE
<222> LOCATION: (77)
<223> OTHER INFORMATION: Xaa=Asp, Glu, Asn, or Ser
<220> FEATURE:
<221> NAME/KEY: MISC_FEATURE
<222> LOCATION: (78)
<223> OTHER INFORMATION: Xaa=Ser, Gln, Asn, or Tyr
<220> FEATURE:
<221> NAME/KEY: MISC_FEATURE
<222> LOCATION: (79)
<223> OTHER INFORMATION: Xaa=Ser, Asn, Asp, or Glu
<220> FEATURE:
<221> NAME/KEY: MISC_FEATURE
<222> LOCATION: (80)
<223> OTHER INFORMATION: Xaa=Asn, Thr or Lys
<220> FEATURE:
<221> NAME/KEY: MISC_FEATURE
<222> LOCATION: (82)
<223> OTHER INFORMATION: Xaa=Ile or Val
<220> FEATURE:
<221> NAME/KEY: MISC_FEATURE
<222> LOCATION: (84)
<223> OTHER INFORMATION: Xaa=Lys or Arg
<220> FEATURE:
<221> NAME/KEY: MISC_FEATURE
<222> LOCATION: (85)
```

<223> OTHER INFORMATION: Xaa=Lys, Asn, Gln, or His
<220> FEATURE:
<221> NAME/KEY: MISC_FEATURE
<222> LOCATION: (86)
<223> OTHER INFORMATION: Xaa=Tyr or His
<220> FEATURE:
<221> NAME/KEY: MISC_FEATURE
<222> LOCATION: (87)
<223> OTHER INFORMATION: Xaa=Arg, Gln or His
<220> FEATURE:
<221> NAME/KEY: MISC_FEATURE
<222> LOCATION: (88)
<223> OTHER INFORMATION: Xaa=Asn, Glu or Asp
<220> FEATURE:
<221> NAME/KEY: MISC_FEATURE
<222> LOCATION: (90)
<223> OTHER INFORMATION: Xaa=Val, Thr or Ala
<220> FEATURE:
<221> NAME/KEY: MISC_FEATURE
<222> LOCATION: (92)
<223> OTHER INFORMATION: Xaa=Arg, Lys, Val, Asp, or Glu
<220> FEATURE:
<221> NAME/KEY: MISC_FEATURE
<222> LOCATION: (93)
<223> OTHER INFORMATION: Xaa=Ala, Gly or Glu
<220> FEATURE:
<221> NAME/KEY: MISC_FEATURE
<222> LOCATION: (97)
<223> OTHER INFORMATION: Xaa=His or Arg

<400> SEQUENCE: 3

Leu Tyr Val Xaa Phe Xaa Xaa Xaa Gly Trp Xaa Xaa Trp Xaa Xaa Ala
1               5                   10                  15

Pro Gly Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Leu
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Leu Xaa Xaa Xaa Xaa Xaa Xaa Xaa Xaa
65                  70                  75                  80

Val Xaa Leu Xaa Xaa Xaa Xaa Xaa Met Xaa Val Xaa Xaa Cys Gly Cys
            85                  90                  95

Xaa

<210> SEQ ID NO 4
<211> LENGTH: 102
<212> TYPE: PRT
<213> ORGANISM: Artificial Sequence
<220> FEATURE:
<223> OTHER INFORMATION: Generic Sequence 4
<220> FEATURE:
<221> NAME/KEY: MISC_FEATURE
<222> LOCATION: (2)
<223> OTHER INFORMATION: Xaa=Lys or Arg
<220> FEATURE:
<221> NAME/KEY: MISC_FEATURE
<222> LOCATION: (3)
<223> OTHER INFORMATION: Xaa=Lys or Arg
<220> FEATURE:
<221> NAME/KEY: MISC_FEATURE
<222> LOCATION: (4)
<223> OTHER INFORMATION: Xaa=His or Arg
<220> FEATURE:
<221> NAME/KEY: MISC_FEATURE
<222> LOCATION: (5)
<223> OTHER INFORMATION: Xaa=Glu, Ser, His, Gly, Arg, or Pro
<220> FEATURE:
<221> NAME/KEY: MISC_FEATURE
<222> LOCATION: (9)
<223> OTHER INFORMATION: Xaa=Ser, Asp or Glu

```
<220> FEATURE:
<221> NAME/KEY: MISC_FEATURE
<222> LOCATION: (11)
<223> OTHER INFORMATION: Xaa=Arg, Gln, Ser, or Lys
<220> FEATURE:
<221> NAME/KEY: MISC_FEATURE
<222> LOCATION: (12)
<223> OTHER INFORMATION: Xaa=Asp or Glu
<220> FEATURE:
<221> NAME/KEY: MISC_FEATURE
<222> LOCATION: (13)
<223> OTHER INFORMATION: Xaa=Leu or Val
<220> FEATURE:
<221> NAME/KEY: MISC_FEATURE
<222> LOCATION: (16)
<223> OTHER INFORMATION: Xaa=Gln, Leu, Asp, His, or Asn
<220> FEATURE:
<221> NAME/KEY: MISC_FEATURE
<222> LOCATION: (17)
<223> OTHER INFORMATION: Xaa=Asp, Arg or Asn
<220> FEATURE:
<221> NAME/KEY: MISC_FEATURE
<222> LOCATION: (19)
<223> OTHER INFORMATION: Xaa=Ile or Val
<220> FEATURE:
<221> NAME/KEY: MISC_FEATURE
<222> LOCATION: (20)
<223> OTHER INFORMATION: Xaa=Ile or Val
<220> FEATURE:
<221> NAME/KEY: MISC_FEATURE
<222> LOCATION: (23)
<223> OTHER INFORMATION: Xaa=Glu, Gln, Leu, Lys, Pro, or Arg
<220> FEATURE:
<221> NAME/KEY: MISC_FEATURE
<222> LOCATION: (25)
<223> OTHER INFORMATION: Xaa=Tyr or Phe
<220> FEATURE:
<221> NAME/KEY: MISC_FEATURE
<222> LOCATION: (26)
<223> OTHER INFORMATION: Xaa=Ala, Ser, Asp, Met, His, Leu, or Gln
<220> FEATURE:
<221> NAME/KEY: MISC_FEATURE
<222> LOCATION: (28)
<223> OTHER INFORMATION: Xaa=Tyr, Asn or Phe
<220> FEATURE:
<221> NAME/KEY: MISC_FEATURE
<222> LOCATION: (31)
<223> OTHER INFORMATION: Xaa=Glu, His, Tyr, Asp, or Gln
<220> FEATURE:
<221> NAME/KEY: MISC_FEATURE
<222> LOCATION: (33)
<223> OTHER INFORMATION: Xaa=Glu, Lys, Asp, or Gln
<220> FEATURE:
<221> NAME/KEY: MISC_FEATURE
<222> LOCATION: (35)
<223> OTHER INFORMATION: Xaa=Ala, Ser, Pro, or Gln
<220> FEATURE:
<221> NAME/KEY: MISC_FEATURE
<222> LOCATION: (36)
<223> OTHER INFORMATION: Xaa=Phe, Leu or Tyr
<220> FEATURE:
<221> NAME/KEY: MISC_FEATURE
<222> LOCATION: (38)
<223> OTHER INFORMATION: Xaa=Leu or Val
<220> FEATURE:
<221> NAME/KEY: MISC_FEATURE
<222> LOCATION: (39)
<223> OTHER INFORMATION: Xaa=Asn, Asp, Ala, or Thr
<220> FEATURE:
<221> NAME/KEY: MISC_FEATURE
<222> LOCATION: (40)
<223> OTHER INFORMATION: Xaa=Ser, Asp, Glu, Leu, or Ala
<220> FEATURE:
<221> NAME/KEY: MISC_FEATURE
<222> LOCATION: (41)
<223> OTHER INFORMATION: Xaa=Tyr, Cys, His, Ser, or Ile
<220> FEATURE:
<221> NAME/KEY: MISC_FEATURE
<222> LOCATION: (42)
```

-continued

```
<223> OTHER INFORMATION: Xaa=Met, Phe, Gly, or Leu
<220> FEATURE:
<221> NAME/KEY: MISC_FEATURE
<222> LOCATION: (43)
<223> OTHER INFORMATION: Xaa=Asn or Ser
<220> FEATURE:
<221> NAME/KEY: MISC_FEATURE
<222> LOCATION: (44)
<223> OTHER INFORMATION: Xaa=Ala, Ser or Gly
<220> FEATURE:
<221> NAME/KEY: MISC_FEATURE
<222> LOCATION: (45)
<223> OTHER INFORMATION: Xaa=Thr, Leu or Ser
<220> FEATURE:
<221> NAME/KEY: MISC_FEATURE
<222> LOCATION: (49)
<223> OTHER INFORMATION: Xaa=Ile or Val
<220> FEATURE:
<221> NAME/KEY: MISC_FEATURE
<222> LOCATION: (50)
<223> OTHER INFORMATION: Xaa=Val or Leu
<220> FEATURE:
<221> NAME/KEY: MISC_FEATURE
<222> LOCATION: (51)
<223> OTHER INFORMATION: Xaa=Gln or Arg
<220> FEATURE:
<221> NAME/KEY: MISC_FEATURE
<222> LOCATION: (52)
<223> OTHER INFORMATION: Xaa=Thr, Ala or Ser
<220> FEATURE:
<221> NAME/KEY: MISC_FEATURE
<222> LOCATION: (54)
<223> OTHER INFORMATION: Xaa=Val or Met
<220> FEATURE:
<221> NAME/KEY: MISC_FEATURE
<222> LOCATION: (55)
<223> OTHER INFORMATION: Xaa=His or Asn
<220> FEATURE:
<221> NAME/KEY: MISC_FEATURE
<222> LOCATION: (56)
<223> OTHER INFORMATION: Xaa=Phe, Leu, Asn, Ser, Ala, or Val
<220> FEATURE:
<221> NAME/KEY: MISC_FEATURE
<222> LOCATION: (57)
<223> OTHER INFORMATION: Xaa=Ile, Met, Asn, Ala, or Val
<220> FEATURE:
<221> NAME/KEY: MISC_FEATURE
<222> LOCATION: (58)
<223> OTHER INFORMATION: Xaa=Asn, Lys, Ala, or Glu
<220> FEATURE:
<221> NAME/KEY: MISC_FEATURE
<222> LOCATION: (59)
<223> OTHER INFORMATION: Xaa=Pro or Ser
<220> FEATURE:
<221> NAME/KEY: MISC_FEATURE
<222> LOCATION: (60)
<223> OTHER INFORMATION: Xaa=Glu, Asp, Asn, or Gly
<220> FEATURE:
<221> NAME/KEY: MISC_FEATURE
<222> LOCATION: (61)
<223> OTHER INFORMATION: Xaa=Thr, Ala, Val, Lys, Asp, Tyr, Ser, or Ala
<220> FEATURE:
<221> NAME/KEY: MISC_FEATURE
<222> LOCATION: (62)
<223> OTHER INFORMATION: Xaa=Val, Ala or Ile
<220> FEATURE:
<221> NAME/KEY: MISC_FEATURE
<222> LOCATION: (63)
<223> OTHER INFORMATION: Xaa=Pro or Asp
<220> FEATURE:
<221> NAME/KEY: MISC_FEATURE
<222> LOCATION: (64)
<223> OTHER INFORMATION: Xaa=Lys or Leu
<220> FEATURE:
<221> NAME/KEY: MISC_FEATURE
<222> LOCATION: (65)
<223> OTHER INFORMATION: Xaa=Pro or Ala
<220> FEATURE:
<221> NAME/KEY: MISC_FEATURE
```

```
<222> LOCATION: (68)
<223> OTHER INFORMATION: Xaa=Ala or Val
<220> FEATURE:
<221> NAME/KEY: MISC_FEATURE
<222> LOCATION: (70)
<223> OTHER INFORMATION: Xaa=Thr or Ala
<220> FEATURE:
<221> NAME/KEY: MISC_FEATURE
<222> LOCATION: (71)
<223> OTHER INFORMATION: Xaa=Gln, Lys, Arg, or Glu
<220> FEATURE:
<221> NAME/KEY: MISC_FEATURE
<222> LOCATION: (72)
<223> OTHER INFORMATION: Xaa=Leu, Met or Val
<220> FEATURE:
<221> NAME/KEY: MISC_FEATURE
<222> LOCATION: (73)
<223> OTHER INFORMATION: Xaa=Asn, Ser or Asp
<220> FEATURE:
<221> NAME/KEY: MISC_FEATURE
<222> LOCATION: (74)
<223> OTHER INFORMATION: Xaa=Ala, Pro or Ser
<220> FEATURE:
<221> NAME/KEY: MISC_FEATURE
<222> LOCATION: (75)
<223> OTHER INFORMATION: Xaa=Ile, Thr or Val
<220> FEATURE:
<221> NAME/KEY: MISC_FEATURE
<222> LOCATION: (76)
<223> OTHER INFORMATION: Xaa=Ser or Ala
<220> FEATURE:
<221> NAME/KEY: MISC_FEATURE
<222> LOCATION: (77)
<223> OTHER INFORMATION: Xaa=Val or Met
<220> FEATURE:
<221> NAME/KEY: MISC_FEATURE
<222> LOCATION: (79)
<223> OTHER INFORMATION: Xaa=Tyr or Phe
<220> FEATURE:
<221> NAME/KEY: MISC_FEATURE
<222> LOCATION: (80)
<223> OTHER INFORMATION: Xaa=Phe, Tyr or Leu
<220> FEATURE:
<221> NAME/KEY: MISC_FEATURE
<222> LOCATION: (81)
<223> OTHER INFORMATION: Xaa=Asp or Asn
<220> FEATURE:
<221> NAME/KEY: MISC_FEATURE
<222> LOCATION: (82)
<223> OTHER INFORMATION: Xaa=Asp, Glu, Asn, or Ser
<220> FEATURE:
<221> NAME/KEY: MISC_FEATURE
<222> LOCATION: (83)
<223> OTHER INFORMATION: Xaa=Ser, Gln, Asn, or Tyr
<220> FEATURE:
<221> NAME/KEY: MISC_FEATURE
<222> LOCATION: (84)
<223> OTHER INFORMATION: Xaa=Ser, Asn, Asp, or Glu
<220> FEATURE:
<221> NAME/KEY: MISC_FEATURE
<222> LOCATION: (85)
<223> OTHER INFORMATION: Xaa=Asn, Thr or Lys
<220> FEATURE:
<221> NAME/KEY: MISC_FEATURE
<222> LOCATION: (87)
<223> OTHER INFORMATION: Xaa=Ile or Val
<220> FEATURE:
<221> NAME/KEY: MISC_FEATURE
<222> LOCATION: (89)
<223> OTHER INFORMATION: Xaa=Lys or Arg
<220> FEATURE:
<221> NAME/KEY: MISC_FEATURE
<222> LOCATION: (90)
<223> OTHER INFORMATION: Xaa=Lys, Asn, Gln, or His
<220> FEATURE:
<221> NAME/KEY: MISC_FEATURE
<222> LOCATION: (91)
<223> OTHER INFORMATION: Xaa=Tyr or His
<220> FEATURE:
```

```
<221> NAME/KEY: MISC_FEATURE
<222> LOCATION: (92)
<223> OTHER INFORMATION: Xaa=Arg, Gln or His
<220> FEATURE:
<221> NAME/KEY: MISC_FEATURE
<222> LOCATION: (93)
<223> OTHER INFORMATION: Xaa=Asn, Glu or Asp
<220> FEATURE:
<221> NAME/KEY: MISC_FEATURE
<222> LOCATION: (95)
<223> OTHER INFORMATION: Xaa=Val, Thr or Ala
<220> FEATURE:
<221> NAME/KEY: MISC_FEATURE
<222> LOCATION: (97)
<223> OTHER INFORMATION: Xaa=Arg, Lys, Val, Asp, or Glu
<220> FEATURE:
<221> NAME/KEY: MISC_FEATURE
<222> LOCATION: (98)
<223> OTHER INFORMATION: Xaa=Ala, Gly or Glu
<220> FEATURE:
<221> NAME/KEY: MISC_FEATURE
<222> LOCATION: (102)
<223> OTHER INFORMATION: Xaa=His or Arg

<400> SEQUENCE: 4

Cys Xaa Xaa Xaa Leu Tyr Val Xaa Phe Xaa Xaa Xaa Gly Trp Xaa
 1               5                  10                  15

Xaa Trp Xaa Xaa Ala Pro Gly Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Leu Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu

Arg Asn Met Val Val Arg Ala Cys Gly Cys His
       130                 135

<210> SEQ ID NO 6
<211> LENGTH: 139
<212> TYPE: PRT
<213> ORGANISM: Mus musculus

<400> SEQUENCE: 6

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Arg Asn Met Val Val Arg Ala Cys Gly Cys His
    130                 135

<210> SEQ ID NO 7
<211> LENGTH: 139
<212> TYPE: PRT
<213> ORGANISM: Homo sapiens

<400> SEQUENCE: 7

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

<210> SEQ ID NO 8
<211> LENGTH: 139
<212> TYPE: PRT
<213> ORGANISM: Mus musculus -continued

<400> SEQUENCE: 8

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Val Ile Leu Arg Lys His
        115                 120                 125

Arg Asn Met Val Val Lys Ala Cys Gly Cys His
    130                 135

<210> SEQ ID NO 9
<211> LENGTH: 101
<212> TYPE: PRT
<213> ORGANISM: Homo sapiens

<400> SEQUENCE: 9

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

<210> SEQ ID NO 10
<211> LENGTH: 101
<212> TYPE: PRT
<213> ORGANISM: Homo sapiens

<400> SEQUENCE: 10

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
    50                  55                  60

Cys Cys Val Pro Thr Glu Leu Ser Ala Ile Ser Met Leu Tyr Leu Asp

```
            65                  70                  75                  80
        Glu Tyr Asp Lys Val Val Leu Lys Asn Tyr Gln Glu Met Val Val Glu
                        85                  90                  95

Gly Cys Gly Cys Arg
                    100

<210> SEQ ID NO 11
<211> LENGTH: 102
<212> TYPE: PRT
<213> ORGANISM: Drosophila melanogaster

<400> SEQUENCE: 11

Cys Arg Arg His Ser Leu Tyr Val Asp Phe Ser Asp Val Gly Trp Asp
        1               5                   10                  15

Asp Trp Ile Val Ala Pro Leu Gly Tyr Asp Ala Tyr Tyr Cys His Gly
                        20                  25                  30

Lys Cys Pro Phe Pro Leu Ala Asp His Phe Asn Ser Thr Asn His Ala
                    35                  40                  45

Val Val Gln Thr Leu Val Asn Asn Met Asn Pro Gly Lys Val Pro Lys
                50                  55                  60

Ala Cys Cys Val Pro Thr Gln Leu Asp Ser Val Ala Met Leu Tyr Leu
        65                  70                  75                  80

Asn Asp Gln Ser Thr Val Val Leu Lys Asn Tyr Gln Glu Met Thr Val
                        85                  90                  95

Val Gly Cys Gly Cys Arg
                    100

<210> SEQ ID NO 12
<211> LENGTH: 102
<212> TYPE: PRT
<213> ORGANISM: Xenopus laevis

<400> SEQUENCE: 12

Cys Lys Lys Arg His Leu Tyr Val Glu Phe Lys Asp Val Gly Trp Gln
        1               5                   10                  15

Asn Trp Val Ile Ala Pro Gln Gly Tyr Met Ala Asn Tyr Cys Tyr Gly
                        20                  25                  30

Glu Cys Pro Tyr Pro Leu Thr Glu Ile Leu Asn Gly Ser Asn His Ala
                    35                  40                  45

Ile Leu Gln Thr Leu Val His Ser Ile Glu Pro Glu Asp Ile Pro Leu
                50                  55                  60

Pro Cys Cys Val Pro Thr Lys Met Ser Pro Ile Ser Met Leu Phe Tyr
        65                  70                  75                  80

Asp Asn Asn Asp Asn Val Val Leu Arg His Tyr Glu Asn Met Ala Val
                        85                  90                  95

Asp Glu Cys Gly Cys Arg
                    100

<210> SEQ ID NO 13
<211> LENGTH: 102
<212> TYPE: PRT
<213> ORGANISM: Mus musculus

<400> SEQUENCE: 13

Cys Lys Lys His Glu Leu Tyr Val Ser Phe Gln Asp Leu Gly Trp Gln
        1               5                   10                  15

Asp Trp Ile Ile Ala Pro Lys Gly Tyr Ala Ala Asn Tyr Cys Asp Gly
                        20                  25                  30
```

```
Glu Cys Ser Phe Pro Leu Asn Ala His Met Asn Ala Thr Asn His Ala
            35                  40                  45

Ile Val Gln Thr Leu Val His Leu Met Asn Pro Glu Tyr Val Pro Lys
 50                  55                  60

Pro Cys Cys Ala Pro Thr Lys Leu Asn Ala Ile Ser Val Leu Tyr Phe
 65                  70                  75                  80

Asp Asp Asn Ser Asn Val Ile Leu Lys Lys Tyr Arg Asn Met Val Val
                85                  90                  95

Arg Ala Cys Gly Cys His
            100

<210> SEQ ID NO 14
<211> LENGTH: 106
<212> TYPE: PRT
<213> ORGANISM: Homo sapiens

<400> SEQUENCE: 14

Cys Arg Ala Arg Arg Leu Tyr Val Ser Phe Arg Glu Val Gly Trp His
 1               5                  10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
 50                  55                  60

Ala Ala Asp Leu Pro Cys Cys Val Pro Ala Arg Leu Ser Pro Ile Ser
 65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105

<210> SEQ ID NO 15
<211> LENGTH: 5
<212> TYPE: PRT
<213> ORGANISM: Artificial Sequence
<220> FEATURE:
<223> OTHER INFORMATION: Generic Sequence 4
<220> FEATURE:
<221> NAME/KEY: MISC_FEATURE
<222> LOCATION: (2)
<223> OTHER INFORMATION: Xaa=Lys or Arg
<220> FEATURE:
<221> NAME/KEY: MISC_FEATURE
<222> LOCATION: (3)
<223> OTHER INFORMATION: Xaa=Lys or Arg
<220> FEATURE:
<221> NAME/KEY: MISC_FEATURE
<222> LOCATION: (4)
<223> OTHER INFORMATION: Xaa=His or Arg
<220> FEATURE:
<221> NAME/KEY: MISC_FEATURE
<222> LOCATION: (5)
<223> OTHER INFORMATION: Xaa=Glu, Ser, His, Gly, Arg, or Pro

<400> SEQUENCE: 15

Cys Xaa Xaa Xaa Xaa
 1               5

<210> SEQ ID NO 16
<211> LENGTH: 1822
<212> TYPE: DNA
<213> ORGANISM: Homo sapiens
```

```
<220> FEATURE:
<221> NAME/KEY: CDS
<222> LOCATION: (49)..(1341)
<223> OTHER INFORMATION:

<400> SEQUENCE: 16
ggtgcgggcc cggagcccgg agcccgggta gcgcgtagag ccggcgcg atg cac gtg          57
                                                     Met His Val
                                                      1 cgc tca ctg cga gct gcg gcg ccg cac agc ttc gtg gcg ctc tgg gca         105
Arg Ser Leu Arg Ala Ala Ala Pro His Ser Phe Val Ala Leu Trp Ala
  5              10                  15 ccc ctg ttc ctg ctg cgc tcc gcc ctg gcc gac ttc agc ctg gac aac         153
Pro Leu Phe Leu Leu Arg Ser Ala Leu Ala Asp Phe Ser Leu Asp Asn
 20              25                  30                  35 gag gtg cac tcg agc ttc atc cac cgg cgc ctc cgc agc cag gag cgg         201
Glu Val His Ser Ser Phe Ile His Arg Arg Leu Arg Ser Gln Glu Arg
                 40                  45                  50 cgg gag atg cag cgc gag atc ctc tcc att ttg ggc ttg ccc cac cgc         249
Arg Glu Met Gln Arg Glu Ile Leu Ser Ile Leu Gly Leu Pro His Arg
             55                  60                  65 ccg cgc ccg cac ctc cag ggc aag cac aac tcg gca ccc atg ttc atg         297
Pro Arg Pro His Leu Gln Gly Lys His Asn Ser Ala Pro Met Phe Met
         70                  75                  80 ctg gac ctg tac aac gcc atg gcg gtg gag gag ggc ggc ggg ccc ggc         345
Leu Asp Leu Tyr Asn Ala Met Ala Val Glu Glu Gly Gly Gly Pro Gly
 85                  90                  95 ggc cag ggc ttc tcc tac ccc tac aag gcc gtc ttc agt acc cag ggc         393
Gly Gln Gly Phe Ser Tyr Pro Tyr Lys Ala Val Phe Ser Thr Gln Gly
100                 105                 110                 115 ccc cct ctg gcc agc ctg caa gat agc cat ttc ctc acc gac gcc gac         441
Pro Pro Leu Ala Ser Leu Gln Asp Ser His Phe Leu Thr Asp Ala Asp
                120                 125                 130 atg gtc atg agc ttc gtc aac ctc gtg gaa cat gac aag gaa ttc ttc         489
Met Val Met Ser Phe Val Asn Leu Val Glu His Asp Lys Glu Phe Phe
            135                 140                 145 cac cca cgc tac cac cat cga gag ttc cgg ttt gat ctt tcc aag atc         537
His Pro Arg Tyr His His Arg Glu Phe Arg Phe Asp Leu Ser Lys Ile
        150                 155                 160 cca gaa ggg gaa gct gtc acg gca gcc gaa ttc cgg atc tac aag gac         585
Pro Glu Gly Glu Ala Val Thr Ala Ala Glu Phe Arg Ile Tyr Lys Asp
    165                 170                 175 tac atc cgg gaa cgc ttc gac aat gag acg ttc cgg atc agc gtt tat         633
Tyr Ile Arg Glu Arg Phe Asp Asn Glu Thr Phe Arg Ile Ser Val Tyr
180                 185                 190                 195 cag gtg ctc cag gag cac ttg ggc agg gaa tcg gat ctc ttc ctg ctc         681
Gln Val Leu Gln Glu His Leu Gly Arg Glu Ser Asp Leu Phe Leu Leu
                200                 205                 210 gac agc cgt acc ctc tgg gcc tcg gag gag ggc tgg ctg gtg ttt gac         729
Asp Ser Arg Thr Leu Trp Ala Ser Glu Glu Gly Trp Leu Val Phe Asp
            215                 220                 225 atc aca gcc acc agc aac cac tgg gtg gtc aat ccg cgg cac aac ctg         777
Ile Thr Ala Thr Ser Asn His Trp Val Val Asn Pro Arg His Asn Leu
        230                 235                 240 ggc ctg cag ctc tcg gtg gag acg ctg gat ggg cag agc atc aac ccc         825
Gly Leu Gln Leu Ser Val Glu Thr Leu Asp Gly Gln Ser Ile Asn Pro
    245                 250                 255 aag ttg gcg ggc ctg att ggg cgg cac ggg ccc cag aac aag cag ccc         873
Lys Leu Ala Gly Leu Ile Gly Arg His Gly Pro Gln Asn Lys Gln Pro
260                 265                 270                 275
```

-continued

| | |
|---|---|
| ttc atg gtg gct ttc ttc aag gcc acg gag gtc cac ttc cgc agc atc<br>Phe Met Val Ala Phe Phe Lys Ala Thr Glu Val His Phe Arg Ser Ile<br>          280                   285                290 | 921 |
| cgg tcc acg ggg agc aaa cag cgc agc cag aac cgc tcc aag acg ccc<br>Arg Ser Thr Gly Ser Lys Gln Arg Ser Gln Asn Arg Ser Lys Thr Pro<br>295                   300                   305 | 969 |
| aag aac cag gaa gcc ctg cgg atg gcc aac gtg gca gag aac agc agc<br>Lys Asn Gln Glu Ala Leu Arg Met Ala Asn Val Ala Glu Asn Ser Ser<br>          310                   315                320 | 1017 |
| agc gac cag agg cag gcc tgt aag aag cac gag ctg tat gtc agc ttc<br>Ser Asp Gln Arg Gln Ala Cys Lys Lys His Glu Leu Tyr Val Ser Phe<br>325                   330                   335 | 1065 |
| cga gac ctg ggc tgg cag gac tgg atc atc gcg cct gaa ggc tac gcc<br>Arg Asp Leu Gly Trp Gln Asp Trp Ile Ile Ala Pro Glu Gly Tyr Ala<br>340                   345                 350               355 | 1113 |
| gcc tac tac tgt gag ggg gag tgt gcc ttc cct ctg aac tcc tac atg<br>Ala Tyr Tyr Cys Glu Gly Glu Cys Ala Phe Pro Leu Asn Ser Tyr Met<br>                360                   365                370 | 1161 |
| aac gcc acc aac cac gcc atc gtg cag acg ctg gtc cac ttc atc aac<br>Asn Ala Thr Asn His Ala Ile Val Gln Thr Leu Val His Phe Ile Asn<br>375                   380                   385 | 1209 |
| ccg gaa acg gtg ccc aag ccc tgc tgt gcg ccc acg cag ctc aat gcc<br>Pro Glu Thr Val Pro Lys Pro Cys Cys Ala Pro Thr Gln Leu Asn Ala<br>          390                   395                400 | 1257 |
| atc tcc gtc ctc tac ttc gat gac agc tcc aac gtc atc ctg aag aaa<br>Ile Ser Val Leu Tyr Phe Asp Asp Ser Ser Asn Val Ile Leu Lys Lys<br>405                   410                   415 | 1305 |
| tac aga aac atg gtg gtc cgg gcc tgt ggc tgc cac tagctcctcc<br>Tyr Arg Asn Met Val Val Arg Ala Cys Gly Cys His<br>420                   425                   430 | 1351 |
| gagaattcag acccttggg gccaagtttt tctggatcct ccattgctcg ccttggccag | 1411 |
| gaaccagcag accaactgcc ttttgtgaga ccttcccctc cctatcccca actttaaagg | 1471 |
| tgtgagagta ttaggaaaca tgagcagcat atggcttttg atcagttttt cagtggcagc | 1531 |
| atccaatgaa caagatccta caagctgtgc aggcaaaacc tagcaggaaa aaaaacaac | 1591 |
| gcataaagaa aaatggccgg gccaggtcat tggctgggaa gtctcagcca tgcacggact | 1651 |
| cgtttccaga ggtaattatg agcgcctacc agccaggcca cccagccgtg ggaggaaggg | 1711 |
| ggcgtggcaa ggggtgggca cattggtgtc tgtgcgaaag gaaaattgac ccggaagttc | 1771 |
| ctgtaataaa tgtcacaata aaacgaatga atgaaaaaaa aaaaaaaaaa a | 1822 |

<210> SEQ ID NO 17
<211> LENGTH: 431
<212> TYPE: PRT
<213> ORGANISM: Homo sapiens

<400> SEQUENCE: 17

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
             20                   25                  30

Leu Asp Asn Glu Val His Ser Ser Phe Ile His Arg Arg Leu Arg Ser
                35                   40                45

Gln Glu Arg Arg Glu Met Gln Arg Glu Ile Leu Ser Ile Leu Gly Leu
        50                   55                  60

Pro His Arg Pro Arg Pro His Leu Gln Gly Lys His Asn Ser Ala Pro
65                 70                   75                  80

```
Met Phe Met Leu Asp Leu Tyr Asn Ala Met Ala Val Glu Glu Gly Gly
                85                  90                  95
Gly Pro Gly Gly Gln Gly Phe Ser Tyr Pro Tyr Lys Ala Val Phe Ser
            100                 105                 110
Thr Gln Gly Pro Pro Leu Ala Ser Leu Gln Asp Ser His Phe Leu Thr
        115                 120                 125
Asp Ala Asp Met Val Met Ser Phe Val Asn Leu Val Glu His Asp Lys
130                 135                 140
Glu Phe Phe His Pro Arg Tyr His Arg Glu Phe Arg Phe Asp Leu
145                 150                 155                 160
Ser Lys Ile Pro Glu Gly Ala Val Thr Ala Ala Glu Phe Arg Ile
                165                 170                 175
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
    210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Lys Ala Thr Glu Val His Phe
        275                 280                 285
Arg Ser Ile Arg Ser Thr Gly Ser Lys Gln Arg Ser Gln Asn Arg Ser
    290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 18
<211> LENGTH: 1873
<212> TYPE: DNA
<213> ORGANISM: Mus musculus
<220> FEATURE:
<221> NAME/KEY: CDS
<222> LOCATION: (104)..(1393)
<223> OTHER INFORMATION:

<400> SEQUENCE: 18
ctgcagcaag tgacctcggg tcgtggaccg ctgccctgcc ccctccgctg ccacctgggg    60
```

-continued

```
cggcgcgggc cggtgcccc ggatcgcgcg tagagccggc gcg atg cac gtg cgc       115
                                            Met His Val Arg
                                            1 tcg ctg cgc gct gcg gcg cca cac agc ttc gtg gcg ctc tgg gcg cct      163
Ser Leu Arg Ala Ala Ala Pro His Ser Phe Val Ala Leu Trp Ala Pro
 5              10                  15                  20 ctg ttc ttg ctg cgc tcc gcc ctg gcc gat ttc agc ctg gac aac gag      211
Leu Phe Leu Leu Arg Ser Ala Leu Ala Asp Phe Ser Leu Asp Asn Glu
             25                  30                  35 gtg cac tcc agc ttc atc cac cgg cgc ctc cgc agc cag gag cgg cgg      259
Val His Ser Ser Phe Ile His Arg Arg Leu Arg Ser Gln Glu Arg Arg
         40                  45                  50 gag atg cag cgg gag atc ctg tcc atc tta ggg ttg ccc cat cgc ccg      307
Glu Met Gln Arg Glu Ile Leu Ser Ile Leu Gly Leu Pro His Arg Pro
     55                  60                  65 cgc ccg cac ctc cag gga aag cat aat tcg gcg ccc atg ttc atg ttg      355
Arg Pro His Leu Gln Gly Lys His Asn Ser Ala Pro Met Phe Met Leu
 70                  75                  80 gac ctg tac aac gcc atg gcg gtg gag gag agc ggg ccg gac gga cag      403
Asp Leu Tyr Asn Ala Met Ala Val Glu Glu Ser Gly Pro Asp Gly Gln
 85                  90                  95                 100 ggc ttc tcc tac ccc tac aag gcc gtc ttc agt acc cag ggc ccc cct      451
Gly Phe Ser Tyr Pro Tyr Lys Ala Val Phe Ser Thr Gln Gly Pro Pro
                 105                 110                 115 tta gcc agc ctg cag gac agc cac ttc ctc act gac gcc gac atg gtc      499
Leu Ala Ser Leu Gln Asp Ser His Phe Leu Thr Asp Ala Asp Met Val
             120                 125                 130 atg agc ttc gtc aac cta gtg gaa cat gac aaa gaa ttc ttc cac cct      547
Met Ser Phe Val Asn Leu Val Glu His Asp Lys Glu Phe Phe His Pro
         135                 140                 145 cga tac cac cat cgg gag ttc cgg ttt gat ctt tcc aag atc ccc gag      595
Arg Tyr His His Arg Glu Phe Arg Phe Asp Leu Ser Lys Ile Pro Glu
     150                 155                 160 ggc gaa cgg gtg acc gca gcc gaa ttc agg atc tat aag gac tac atc      643
Gly Glu Arg Val Thr Ala Ala Glu Phe Arg Ile Tyr Lys Asp Tyr Ile
165                 170                 175                 180 cgg gag cga ttt gac aac gag acc ttc cag atc aca gtc tat cag gtg      691
Arg Glu Arg Phe Asp Asn Glu Thr Phe Gln Ile Thr Val Tyr Gln Val
                 185                 190                 195 ctc cag gag cac tca ggc agg gag tcg gac ctc ttc ttg ctg gac agc      739
Leu Gln Glu His Ser Gly Arg Glu Ser Asp Leu Phe Leu Leu Asp Ser
             200                 205                 210 cgc acc atc tgg gct tct gag gag ggc tgg ttg gtg ttt gat atc aca      787
Arg Thr Ile Trp Ala Ser Glu Glu Gly Trp Leu Val Phe Asp Ile Thr
         215                 220                 225 gcc acc agc aac cac tgg gtg gtc aac cct cgg cac aac ctg ggc tta      835
Ala Thr Ser Asn His Trp Val Val Asn Pro Arg His Asn Leu Gly Leu
     230                 235                 240 cag ctc tct gtg gag acc ctg gat ggg cag agc atc aac ccc aag ttg      883
Gln Leu Ser Val Glu Thr Leu Asp Gly Gln Ser Ile Asn Pro Lys Leu
245                 250                 255                 260 gca ggc ctg att gga cgg cat gga ccc cag aac aag caa ccc ttc atg      931
Ala Gly Leu Ile Gly Arg His Gly Pro Gln Asn Lys Gln Pro Phe Met
                 265                 270                 275 gtg gcc ttc ttc aag gcc acg gaa gtc cat ctc cgt agt atc cgg tcc      979
Val Ala Phe Phe Lys Ala Thr Glu Val His Leu Arg Ser Ile Arg Ser
             280                 285                 290 acg ggg ggc aag cag cgc agc cag aat cgc tcc aag acg cca aag aac     1027
Thr Gly Gly Lys Gln Arg Ser Gln Asn Arg Ser Lys Thr Pro Lys Asn
```

-continued

```
                    295                 300                 305
caa gag gcc ctg agg atg gcc agt gtg gca gaa aac agc agc agt gac        1075
Gln Glu Ala Leu Arg Met Ala Ser Val Ala Glu Asn Ser Ser Ser Asp
        310                 315                 320 cag agg cag gcc tgc aag aaa cat gag ctg tac gtc agc ttc cga gac        1123
Gln Arg Gln Ala Cys Lys Lys His Glu Leu Tyr Val Ser Phe Arg Asp
325                 330                 335                 340 ctt ggc tgg cag gac tgg atc att gca cct gaa ggc tat gct gcc tac        1171
Leu Gly Trp Gln Asp Trp Ile Ile Ala Pro Glu Gly Tyr Ala Ala Tyr
                    345                 350                 355 tac tgt gag gga gag tgc gcc ttc cct ctg aac tcc tac atg aac gcc        1219
Tyr Cys Glu Gly Glu Cys Ala Phe Pro Leu Asn Ser Tyr Met Asn Ala
                360                 365                 370 acc aac cac gcc atc gtc cag aca ctg gtt cac ttc atc aac cca gac        1267
Thr Asn His Ala Ile Val Gln Thr Leu Val His Phe Ile Asn Pro Asp
            375                 380                 385 aca gta ccc aag ccc tgc tgt gcg ccc acc cag ctc aac gcc atc tct        1315
Thr Val Pro Lys Pro Cys Cys Ala Pro Thr Gln Leu Asn Ala Ile Ser
        390                 395                 400 gtc ctc tac ttc gac gac agc tct aat gtc atc ctg aag aag tac aga        1363
Val Leu Tyr Phe Asp Asp Ser Ser Asn Val Ile Leu Lys Lys Tyr Arg
405                 410                 415                 420 aac atg gtg gtc cgg gcc tgt ggc tgc cac tagctcttcc tgagccctg          1413
Asn Met Val Val Arg Ala Cys Gly Cys His
                    425                 430 acctttgcgg ggccacacct ttccaaatct tcgatgtctc accatctaag tctctcactg    1473
cccaccttgg cgaggagaac agaccaacct ctcctgagcc ttccctcacc tcccaaccgg    1533
aagcatgtaa gggttccaga aacctgagcg tgcagcagct gatgagcgcc ctttccttct    1593
ggcacgtgac ggacaagatc ctaccagcta ccacagcaaa cgcctaagag caggaaaaat    1653
gtctgccagg aaagtgtcca ttggccacat ggccctggc gctctgagtc tttgaggagt     1713
aatcgcaagc ctcgttcagc tgcagcagaa ggaagggctt agccagggtg ggcgctggcg    1773
tctgtgttga agggaaacca agcagaagcc actgtaatga tatgtcacaa taaaacccat    1833
gaatgaaaaa aaaaaaaaaa aaaaaaaaaa aaaagaattc                          1873
```

<210> SEQ ID NO 19
<211> LENGTH: 430
<212> TYPE: PRT
<213> ORGANISM: Mus musculus

<400> SEQUENCE: 19

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110
```

```
Gln Gly Pro Pro Leu Ala Ser Leu Gln Asp Ser His Phe Leu Thr Asp
        115                 120                 125
Ala Asp Met Val Met Ser Phe Val Asn Leu Val Glu His Asp Lys Glu
130                 135                 140
Phe Phe His Pro Arg Tyr His His Arg Glu Phe Arg Phe Asp Leu Ser
145                 150                 155                 160
Lys Ile Pro Glu Gly Glu Arg Val Thr Ala Ala Glu Phe Arg Ile Tyr
                165                 170                 175
Lys Asp Tyr Ile Arg Glu Arg Phe Asp Asn Glu Thr Phe Gln Ile Thr
            180                 185                 190
Val Tyr Gln Val Leu Gln Glu His Ser Gly Arg Glu Ser Asp Leu Phe
        195                 200                 205
Leu Leu Asp Ser Arg Thr Ile Trp Ala Ser Glu Glu Gly Trp Leu Val
    210                 215                 220
Phe Asp Ile Thr Ala Thr Ser Asn His Trp Val Val Asn Pro Arg His
225                 230                 235                 240
Asn Leu Gly Leu Gln Leu Ser Val Glu Thr Leu Asp Gly Gln Ser Ile
                245                 250                 255
Asn Pro Lys Leu Ala Gly Leu Ile Gly Arg His Gly Pro Gln Asn Lys
            260                 265                 270
Gln Pro Phe Met Val Ala Phe Phe Lys Ala Thr Glu Val His Leu Arg
        275                 280                 285
Ser Ile Arg Ser Thr Gly Gly Lys Gln Arg Ser Gln Asn Arg Ser Lys
    290                 295                 300
Thr Pro Lys Asn Gln Glu Ala Leu Arg Met Ala Ser Val Ala Glu Asn
305                 310                 315                 320
Ser Ser Ser Asp Gln Arg Gln Ala Cys Lys Lys His Glu Leu Tyr Val
                325                 330                 335
Ser Phe Arg Asp Leu Gly Trp Gln Asp Trp Ile Ile Ala Pro Glu Gly
            340                 345                 350
Tyr Ala Ala Tyr Tyr Cys Glu Gly Glu Cys Ala Phe Pro Leu Asn Ser
        355                 360                 365
Tyr Met Asn Ala Thr Asn His Ala Ile Val Gln Thr Leu Val His Phe
    370                 375                 380
Ile Asn Pro Asp Thr Val Pro Lys Pro Cys Cys Ala Pro Thr Gln Leu
385                 390                 395                 400
Asn Ala Ile Ser Val Leu Tyr Phe Asp Asp Ser Ser Asn Val Ile Leu
                405                 410                 415
Lys Lys Tyr Arg Asn Met Val Val Arg Ala Cys Gly Cys His
            420                 425                 430

<210> SEQ ID NO 20
<211> LENGTH: 1723
<212> TYPE: DNA
<213> ORGANISM: Homo sapiens
<220> FEATURE:
<221> NAME/KEY: CDS
<222> LOCATION: (490)..(1695)
<223> OTHER INFORMATION:

<400> SEQUENCE: 20
ggcgccggca gagcaggagt ggctggagga gctgtggttg gagcaggagg tggcacggca      60
gggctggagg gctccctatg agtggcggag acggcccagg aggcgctgga gcaacagctc     120
ccacaccgca ccaagcggtg gctgcaggag ctcgcccatc gcccctgcgc tgctcggacc     180
gcggccacag ccggactggc gggtacggcg gcgacagacg gattggccga gagtcccagt     240
```

-continued

```
ccgcagagta gccccggcct cgaggcggtg gcgtcccggt cctctccgtc caggagccag      300
gacaggtgtc gcgcggcggg gctccaggga ccgcgcctga ggccggctgc ccgcccgtcc      360
cgccccgccc cgccgcccgc cgcccgccga gccagcctc cttgccgtcg ggcgtccccc       420
aggccctggg tcggccgcgg agccgatgcg cgcccgctga gcgcccagc tgagcgcccc       480 cggcctgcc atg acc gcg ctc ccc ggc ccg ctc tgg ctc ctg ggc ctg gcg      531
         Met Thr Ala Leu Pro Gly Pro Leu Trp Leu Leu Gly Leu Ala
           1               5                  10 cta tgc gcg ctg ggc ggg ggc ggc ccc ggc ctg cga ccc ccg ccc ggc        579
Leu Cys Ala Leu Gly Gly Gly Gly Pro Gly Leu Arg Pro Pro Pro Gly
 15              20                  25                  30 tgt ccc cag cga cgt ctg ggc gcg cgc gag cgc cgg gac gtg cag cgc        627
Cys Pro Gln Arg Arg Leu Gly Ala Arg Glu Arg Arg Asp Val Gln Arg
                 35                  40                  45 gag atc ctg gcg gtg ctc ggg ctg cct ggg cgg ccc cgg ccc cgc gcg        675
Glu Ile Leu Ala Val Leu Gly Leu Pro Gly Arg Pro Arg Pro Arg Ala
             50                  55                  60 cca ccc gcc gcc tcc cgg ctg ccc gcg tcc gcg ccg ctc ttc atg ctg        723
Pro Pro Ala Ala Ser Arg Leu Pro Ala Ser Ala Pro Leu Phe Met Leu
         65                  70                  75 gac ctg tac cac gcc atg gcc ggc gac gac gac gag gac ggc gcg ccc        771
Asp Leu Tyr His Ala Met Ala Gly Asp Asp Asp Glu Asp Gly Ala Pro
     80                  85                  90 gcg gag cgg cgc ctg ggc cgc gcc gac ctg gtc atg agc ttc gtt aac        819
Ala Glu Arg Arg Leu Gly Arg Ala Asp Leu Val Met Ser Phe Val Asn
 95                 100                 105                 110 atg gtg gag cga gac cgt gcc ctg ggc cac cag gag ccc cat tgg aag        867
Met Val Glu Arg Asp Arg Ala Leu Gly His Gln Glu Pro His Trp Lys
                 115                 120                 125 gag ttc cgc ttt gac ctg acc cag atc ccg gct ggg gag gcg gtc aca        915
Glu Phe Arg Phe Asp Leu Thr Gln Ile Pro Ala Gly Glu Ala Val Thr
             130                 135                 140 gct gcg gag ttc cgg att tac aag gtg ccc agc atc cac ctg ctc aac        963
Ala Ala Glu Phe Arg Ile Tyr Lys Val Pro Ser Ile His Leu Leu Asn
         145                 150                 155 agg acc ctc cac gtc agc atg ttc cag gtg gtc cag gag cag tcc aac       1011
Arg Thr Leu His Val Ser Met Phe Gln Val Val Gln Glu Gln Ser Asn
     160                 165                 170 agg gag tct gac ttg ttc ttt ttg gat ctt cag acg ctc cga gct gga       1059
Arg Glu Ser Asp Leu Phe Phe Leu Asp Leu Gln Thr Leu Arg Ala Gly
 175                 180                 185                 190 gac gag ggc tgg ctg gtg ctg gat gtc aca gca gcc agt gac tgc tgg       1107
Asp Glu Gly Trp Leu Val Leu Asp Val Thr Ala Ala Ser Asp Cys Trp
                 195                 200                 205 ttg ctg aag cgt cac aag gac ctg gga ctc cgc ctc tat gtg gag act       1155
Leu Leu Lys Arg His Lys Asp Leu Gly Leu Arg Leu Tyr Val Glu Thr
             210                 215                 220 gag gac ggg cac agc gtg gat cct ggc ctg gcc ggc ctg ctg ggt caa       1203
Glu Asp Gly His Ser Val Asp Pro Gly Leu Ala Gly Leu Leu Gly Gln
         225                 230                 235 cgg gcc cca cgc tcc caa cag cct ttc gtg gtc act ttc ttc agg gcc       1251
Arg Ala Pro Arg Ser Gln Gln Pro Phe Val Val Thr Phe Phe Arg Ala
     240                 245                 250 agt ccg agt ccc atc cgc acc cct cgg gca gtg agg cca ctg agg agg       1299
Ser Pro Ser Pro Ile Arg Thr Pro Arg Ala Val Arg Pro Leu Arg Arg
 255                 260                 265                 270 agg cag ccg aag aaa agc aac gag ctg ccg cag gcc aac cga ctc cca       1347
Arg Gln Pro Lys Lys Ser Asn Glu Leu Pro Gln Ala Asn Arg Leu Pro
```

-continued

```
                     275                 280                 285
ggg atc ttt gat gac gtc cac ggc tcc cac ggc cgg cag gtc tgc cgt          1395
Gly Ile Phe Asp Asp Val His Gly Ser His Gly Arg Gln Val Cys Arg
            290                 295                 300 cgg cac gag ctc tac gtc agc ttc cag gac ctc ggc tgg ctg gac tgg          1443
Arg His Glu Leu Tyr Val Ser Phe Gln Asp Leu Gly Trp Leu Asp Trp
        305                 310                 315 gtc atc gct ccc caa ggc tac tcg gcc tat tac tgt gag ggg gag tgc          1491
Val Ile Ala Pro Gln Gly Tyr Ser Ala Tyr Tyr Cys Glu Gly Glu Cys
320                 325                 330 tcc ttc cca ctg gac tcc tgc atg aat gcc acc aac cac gcc atc ctg          1539
Ser Phe Pro Leu Asp Ser Cys Met Asn Ala Thr Asn His Ala Ile Leu
335                 340                 345                 350 cag tcc ctg gtg cac ctg atg aag cca aac gca gtc ccc aag gcg tgc          1587
Gln Ser Leu Val His Leu Met Lys Pro Asn Ala Val Pro Lys Ala Cys
                355                 360                 365 tgt gca ccc acc aag ctg agc gcc acc tct gtg ctc tac tat gac agc          1635
Cys Ala Pro Thr Lys Leu Ser Ala Thr Ser Val Leu Tyr Tyr Asp Ser
            370                 375                 380 agc aac aac gtc atc ctg cgc aag cac cgc aac atg gtg gtc aag gcc          1683
Ser Asn Asn Val Ile Leu Arg Lys His Arg Asn Met Val Val Lys Ala
        385                 390                 395 tgc ggc tgc cac tgagtcagcc cgcccagccc tactgcag                           1723
Cys Gly Cys His
    400
```

<210> SEQ ID NO 21
<211> LENGTH: 402
<212> TYPE: PRT
<213> ORGANISM: Homo sapiens

<400> SEQUENCE: 21

```
Met Thr Ala Leu Pro Gly Pro Leu Trp Leu Leu Gly Leu Ala Leu Cys
1               5                   10                  15

Ala Leu Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
        35                  40                  45

Leu Ala Val Leu Gly Leu Pro Gly Arg Pro Arg Pro Arg Ala Pro Pro
    50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
    130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
```

```
                   195                 200                 205
Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
    290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
    370                 375                 380

Asn Val Ile Leu Arg Lys His Arg Asn Met Val Val Lys Ala Cys Gly
385                 390                 395                 400

Cys His

<210> SEQ ID NO 22
<211> LENGTH: 1926
<212> TYPE: DNA
<213> ORGANISM: Mus musculus
<220> FEATURE:
<221> NAME/KEY: CDS
<222> LOCATION: (93)..(1289)
<223> OTHER INFORMATION:

<400> SEQUENCE: 22
gccaggcaca  ggtgcgccgt  ctggtcctcc  ccgtctggcg  tcagccgagc  ccgaccagct      60
accagtggat  gcgcgccggc  tgaaagtccg  ag atg gct atg cgt ccc ggg cca          113
                                      Met Ala Met Arg Pro Gly Pro
                                        1               5 ctc tgg cta ttg ggc ctt gct ctg tgc gcg ctg gga ggc ggc cac ggt              161
Leu Trp Leu Leu Gly Leu Ala Leu Cys Ala Leu Gly Gly Gly His Gly
        10                  15                  20 ccg cgt ccc ccg cac acc tgt ccc cag cgt cgc ctg gga gcg cgc gag              209
Pro Arg Pro Pro His Thr Cys Pro Gln Arg Arg Leu Gly Ala Arg Glu
    25                  30                  35 cgc cgc gac atg cag cgt gaa atc ctg gcg gtg ctc ggg cta ccg gga              257
Arg Arg Asp Met Gln Arg Glu Ile Leu Ala Val Leu Gly Leu Pro Gly
40                  45                  50                  55 cgg ccc cga ccc cgt gca caa ccc gcc gct gcc cgg cag cca gcg tcc              305
Arg Pro Arg Pro Arg Ala Gln Pro Ala Ala Ala Arg Gln Pro Ala Ser
                60                  65                  70 gcg ccc ctc ttc atg ttg gac cta tac cac gcc atg acc gat gac gac              353
Ala Pro Leu Phe Met Leu Asp Leu Tyr His Ala Met Thr Asp Asp Asp
        75                  80                  85 gac ggc ggg cca cca cag gct cac tta ggc cgt gcc gac ctg gtc atg              401
```

```
Asp Gly Gly Pro Pro Gln Ala His Leu Gly Arg Ala Asp Leu Val Met
         90                  95                 100 agc ttc gtc aac atg gtg gaa cgc gac cgt acc ctg ggc tac cag gag    449
Ser Phe Val Asn Met Val Glu Arg Asp Arg Thr Leu Gly Tyr Gln Glu
    105                 110                 115 cca cac tgg aag gaa ttc cac ttt gac cta acc cag atc cct gct ggg    497
Pro His Trp Lys Glu Phe His Phe Asp Leu Thr Gln Ile Pro Ala Gly
120                 125                 130                 135 gag gct gtc aca gct gct gag ttc cgg atc tac aaa gaa ccc agc acc    545
Glu Ala Val Thr Ala Ala Glu Phe Arg Ile Tyr Lys Glu Pro Ser Thr
                140                 145                 150 cac ccg ctc aac aca acc ctc cac atc agc atg ttc gaa gtg gtc caa    593
His Pro Leu Asn Thr Thr Leu His Ile Ser Met Phe Glu Val Val Gln
            155                 160                 165 gag cac tcc aac agg gag tct gac ttg ttc ttt ttg gat ctt cag acg    641
Glu His Ser Asn Arg Glu Ser Asp Leu Phe Phe Leu Asp Leu Gln Thr
        170                 175                 180 ctc cga tct ggg gac gag ggc tgg ctg gtg ctg gac atc aca gca gcc    689
Leu Arg Ser Gly Asp Glu Gly Trp Leu Val Leu Asp Ile Thr Ala Ala
    185                 190                 195 agt gac cga tgg ctg ctg aac cat cac aag gac ctg gga ctc cgc ctc    737
Ser Asp Arg Trp Leu Leu Asn His His Lys Asp Leu Gly Leu Arg Leu
200                 205                 210                 215 tat gtg gaa acc gcg gat ggg cac agc atg gat cct ggc ctg gct ggt    785
Tyr Val Glu Thr Ala Asp Gly His Ser Met Asp Pro Gly Leu Ala Gly
                220                 225                 230 ctg ctt gga cga caa gca cca cgc tcc aga cag cct ttc atg gta acc    833
Leu Leu Gly Arg Gln Ala Pro Arg Ser Arg Gln Pro Phe Met Val Thr
            235                 240                 245 ttc ttc agg gcc agc cag agt cct gtg cgg gcc cct cgg gca gcg aga    881
Phe Phe Arg Ala Ser Gln Ser Pro Val Arg Ala Pro Arg Ala Ala Arg
        250                 255                 260 cca ctg aag agg agg cag cca aag aaa acg aac gag ctt ccg cac ccc    929
Pro Leu Lys Arg Arg Gln Pro Lys Lys Thr Asn Glu Leu Pro His Pro
    265                 270                 275 aac aaa ctc cca ggg atc ttt gat gat ggc cac ggt tcc cgc ggc aga    977
Asn Lys Leu Pro Gly Ile Phe Asp Asp Gly His Gly Ser Arg Gly Arg
280                 285                 290                 295 gag gtt tgc cgc agg cat gag ctc tac gtc agc ttc cgt gac ctt ggc    1025
Glu Val Cys Arg Arg His Glu Leu Tyr Val Ser Phe Arg Asp Leu Gly
                300                 305                 310 tgg ctg gac tgg gtc atc gcc ccc cag ggc tac tct gcc tat tac tgt    1073
Trp Leu Asp Trp Val Ile Ala Pro Gln Gly Tyr Ser Ala Tyr Tyr Cys
            315                 320                 325 gag ggg gag tgt gct ttc cca ctg gac tcc tgt atg aac gcc acc aac    1121
Glu Gly Glu Cys Ala Phe Pro Leu Asp Ser Cys Met Asn Ala Thr Asn
        330                 335                 340 cat gcc atc ttg cag tct ctg gtg cac ctg atg aag cca gat gtt gtc    1169
His Ala Ile Leu Gln Ser Leu Val His Leu Met Lys Pro Asp Val Val
    345                 350                 355 ccc aag gca tgc tgt gca ccc acc aaa ctg agt gcc acc tct gtg ctg    1217
Pro Lys Ala Cys Cys Ala Pro Thr Lys Leu Ser Ala Thr Ser Val Leu
360                 365                 370                 375 tac tat gac agc agc aac aat gtc atc ctg cgt aaa cac cgt aac atg    1265
Tyr Tyr Asp Ser Ser Asn Asn Val Ile Leu Arg Lys His Arg Asn Met
                380                 385                 390 gtg gtc aag gcc tgt ggc tgc cac tgaggccccg cccagcatcc tgcttctact    1319
Val Val Lys Ala Cys Gly Cys His
                395
```

-continued

```
accttaccat ctggccgggc ccctctccag aggcagaaac ccttctatgt tatcatagct    1379
cagacagggg caatgggagg cccttcactt ccctggcca cttcctgcta aaattctggt    1439
ctttcccagt tcctctgtcc ttcatggggt tcggggcta tcaccccgcc ctctccatcc    1499
tcctacccca agcatagact gaatgcacac agcatcccag agctatgcta actgagaggt    1559
ctggggtcag cactgaaggc ccacatgagg aagactgatc cttggccatc ctcagcccac    1619
aatggcaaat tctggatggt ctaagaagcc ctggaattct aaactagatg atctgggctc    1679
tctgcaccat tcattgtggc agttgggaca ttttaggta taacagacac atacacttag    1739
atcaatgcat cgctgtactc cttgaaatca gagctagctt gttagaaaaa gaatcagagc    1799
caggtatagc ggtgcatgtc attaatccca gcgctaaaga gacagagaca ggagaatctc    1859
tgtgagttca aggccacata gaaagagcct gtctcgggag caggaaaaaa aaaaaaaaac    1919
ggaattc                                                             1926
```

<210> SEQ ID NO 23
<211> LENGTH: 399
<212> TYPE: PRT
<213> ORGANISM: Mus musculus

<400> SEQUENCE: 23

```
Met Ala Met Arg Pro Gly Pro Leu Trp Leu Leu Gly Leu Ala Leu Cys
 1               5                  10                  15

Ala Leu Gly Gly Gly His Gly Pro Arg Pro Pro His Thr Cys Pro Gln
            20                  25                  30

Arg Arg Leu Gly Ala Arg Glu Arg Asp Met Gln Arg Glu Ile Leu
        35                  40                  45

Ala Val Leu Gly Leu Pro Gly Arg Pro Arg Pro Arg Ala Gln Pro Ala
    50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
    130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
    210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
```

-continued

```
                    260                 265                 270
    Thr Asn Glu Leu Pro His Pro Asn Lys Leu Pro Gly Ile Phe Asp Asp
            275                 280                 285

Gly His Gly Ser Arg Gly Arg Glu Val Cys Arg Arg His Glu Leu Tyr
            290                 295                 300

Val Ser Phe Arg Asp Leu Gly Trp Leu Asp Trp Val Ile Ala Pro Gln
    305                 310                 315                 320

Gly Tyr Ser Ala Tyr Tyr Cys Glu Gly Glu Cys Ala Phe Pro Leu Asp
                    325                 330                 335

Ser Cys Met Asn Ala Thr Asn His Ala Ile Leu Gln Ser Leu Val His
                340                 345                 350

Leu Met Lys Pro Asp Val Val Pro Lys Ala Cys Cys Ala Pro Thr Lys
                355                 360                 365

Leu Ser Ala Thr Ser Val Leu Tyr Tyr Asp Ser Ser Asn Asn Val Ile
            370                 375                 380

Leu Arg Lys His Arg Asn Met Val Val Lys Ala Cys Gly Cys His
    385                 390                 395

<210> SEQ ID NO 24
<211> LENGTH: 1368
<212> TYPE: DNA
<213> ORGANISM: Drosophila melanogaster
<220> FEATURE:
<221> NAME/KEY: CDS
<222> LOCATION: (1)..(1368)
<223> OTHER INFORMATION:

<400> SEQUENCE: 24 atg tcg gga ctg cga aac acc tcg gag gcc gtt gca gtg ctc gcc tcc        48
Met Ser Gly Leu Arg Asn Thr Ser Glu Ala Val Ala Val Leu Ala Ser
1               5                   10                  15 ctg gga ctc gga atg gtt ctg ctc atg ttc gtg gcg acc acg ccg ccg        96
Leu Gly Leu Gly Met Val Leu Leu Met Phe Val Ala Thr Thr Pro Pro
                20                  25                  30 gcc gtt gag gcc acc cag tcg ggg att tac ata gac aac ggc aag gac       144
Ala Val Glu Ala Thr Gln Ser Gly Ile Tyr Ile Asp Asn Gly Lys Asp
            35                  40                  45 cag acg atc atg cac aga gtg ctg agc gag gac gac aag ctg gac gtc       192
Gln Thr Ile Met His Arg Val Leu Ser Glu Asp Asp Lys Leu Asp Val
        50                  55                  60 tcg tac gag atc ctc gag ttc ctg ggc atc gcc gaa cgg ccg acg cac       240
Ser Tyr Glu Ile Leu Glu Phe Leu Gly Ile Ala Glu Arg Pro Thr His
65                  70                  75                  80 ctg agc agc cac cag ttg tcg ctg agg aag tcg gct ccc aag ttc ctg       288
Leu Ser Ser His Gln Leu Ser Leu Arg Lys Ser Ala Pro Lys Phe Leu
                85                  90                  95 ctg gac gtc tac cac cgc atc acg gcg gag gag ggt ctc agc gat cag       336
Leu Asp Val Tyr His Arg Ile Thr Ala Glu Glu Gly Leu Ser Asp Gln
                100                 105                 110 gat gag gac gac gac tac gaa cgc ggc cat cgg tcc agg agg agc gcc       384
Asp Glu Asp Asp Asp Tyr Glu Arg Gly His Arg Ser Arg Arg Ser Ala
            115                 120                 125 gac ctc gag gag gat gag ggc gag cag cag aag aac ttc atc acc gac       432
Asp Leu Glu Glu Asp Glu Gly Glu Gln Gln Lys Asn Phe Ile Thr Asp
        130                 135                 140 ctg gac aag cgg gcc atc gac gag agc gac atc atc atg acc ttc ctg       480
Leu Asp Lys Arg Ala Ile Asp Glu Ser Asp Ile Ile Met Thr Phe Leu
145                 150                 155                 160 aac aag cgc cac cac aat gtg gac gaa ctg cgt cac gag cac ggc cgt       528
```

```
                Asn Lys Arg His His Asn Val Asp Glu Leu Arg His Glu His Gly Arg
                                165                 170                 175 cgc ctg tgg ttc gac gtc tcc aac gtg ccc aac gac aac tac ctg gtg            576
Arg Leu Trp Phe Asp Val Ser Asn Val Pro Asn Asp Asn Tyr Leu Val
            180                 185                 190 atg gcc gag ctg cgc atc tat cag aac gcc aac gag ggc aag tgg ctg            624
Met Ala Glu Leu Arg Ile Tyr Gln Asn Ala Asn Glu Gly Lys Trp Leu
        195                 200                 205 acc gcc aac agg gag ttc acc atc acg gta tac gcc att ggc acc ggc            672
Thr Ala Asn Arg Glu Phe Thr Ile Thr Val Tyr Ala Ile Gly Thr Gly
    210                 215                 220 acg ctg ggc cag cac acc atg gag ccg ctg tcc tcg gtg aac acc acc            720
Thr Leu Gly Gln His Thr Met Glu Pro Leu Ser Ser Val Asn Thr Thr
225                 230                 235                 240 ggg gac tac gtg ggc tgg ttg gag ctc aac gtg acc gag ggc ctg cac            768
Gly Asp Tyr Val Gly Trp Leu Glu Leu Asn Val Thr Glu Gly Leu His
                245                 250                 255 gag tgg ctg gtc aag tcg aag gac aat cat ggc atc tac att gga gca            816
Glu Trp Leu Val Lys Ser Lys Asp Asn His Gly Ile Tyr Ile Gly Ala
            260                 265                 270 cac gct gtc aac cga ccc gac cgc gag gtg aag ctg gac gac att gga            864
His Ala Val Asn Arg Pro Asp Arg Glu Val Lys Leu Asp Asp Ile Gly
        275                 280                 285 ctg atc cac cgc aag gtg gac gac gag ttc cag ccc ttc atg atc ggc            912
Leu Ile His Arg Lys Val Asp Asp Glu Phe Gln Pro Phe Met Ile Gly
    290                 295                 300 ttc ttc cgc gga ccg gag ctg atc aag gcg acg gcc cac agc agc cac            960
Phe Phe Arg Gly Pro Glu Leu Ile Lys Ala Thr Ala His Ser Ser His
305                 310                 315                 320 cac agg agc aag cga agc gcc agc cat cca cgc aag cgc aag aag tcg           1008
His Arg Ser Lys Arg Ser Ala Ser His Pro Arg Lys Arg Lys Lys Ser
                325                 330                 335 gtg tcg ccc aac aac gtg ccg ctg ctg gaa ccg atg gag agc acg cgc           1056
Val Ser Pro Asn Asn Val Pro Leu Leu Glu Pro Met Glu Ser Thr Arg
            340                 345                 350 agc tgc cag atg cag acc ctg tac ata gac ttc aag gat ctg ggc tgg           1104
Ser Cys Gln Met Gln Thr Leu Tyr Ile Asp Phe Lys Asp Leu Gly Trp
        355                 360                 365 cat gac tgg atc atc gca cca gag ggc tat ggc gcc ttc tac tgc agc           1152
His Asp Trp Ile Ile Ala Pro Glu Gly Tyr Gly Ala Phe Tyr Cys Ser
    370                 375                 380 ggc gag tgc aat ttc ccg ctc aat gcg cac atg aac gcc acg aac cat           1200
Gly Glu Cys Asn Phe Pro Leu Asn Ala His Met Asn Ala Thr Asn His
385                 390                 395                 400 gcg atc gtc cag acc ctg gtc cac ctg ctg gag ccc aag aag gtg ccc           1248
Ala Ile Val Gln Thr Leu Val His Leu Leu Glu Pro Lys Lys Val Pro
                405                 410                 415 aag ccc tgc tgc gct ccg acc agg ctg gga gca cta ccc gtt ctg tac           1296
Lys Pro Cys Cys Ala Pro Thr Arg Leu Gly Ala Leu Pro Val Leu Tyr
            420                 425                 430 cac ctg aac gac gag aat gtg aac ctg aaa aag tat aga aac atg att           1344
His Leu Asn Asp Glu Asn Val Asn Leu Lys Lys Tyr Arg Asn Met Ile
        435                 440                 445 gtg aaa tcc tgc ggg tgc cat tga                                            1368
Val Lys Ser Cys Gly Cys His
    450                 455

<210> SEQ ID NO 25
<211> LENGTH: 455
<212> TYPE: PRT
```

<213> ORGANISM: Drosophila melanogaster

<400> SEQUENCE: 25

```
Met Ser Gly Leu Arg Asn Thr Ser Glu Ala Val Ala Val Leu Ala Ser
1               5                   10                  15
Leu Gly Leu Gly Met Val Leu Leu Met Phe Val Ala Thr Thr Pro Pro
                20                  25                  30
Ala Val Glu Ala Thr Gln Ser Gly Ile Tyr Ile Asp Asn Gly Lys Asp
            35                  40                  45
Gln Thr Ile Met His Arg Val Leu Ser Glu Asp Lys Leu Asp Val
    50                  55                  60
Ser Tyr Glu Ile Leu Glu Phe Leu Gly Ile Ala Glu Arg Pro Thr His
65                  70                  75                  80
Leu Ser Ser His Gln Leu Ser Leu Arg Lys Ser Ala Pro Lys Phe Leu
                85                  90                  95
Leu Asp Val Tyr His Arg Ile Thr Ala Glu Glu Gly Leu Ser Asp Gln
                100                 105                 110
Asp Glu Asp Asp Asp Tyr Glu Arg Gly His Arg Ser Arg Arg Ser Ala
            115                 120                 125
Asp Leu Glu Glu Asp Glu Gly Glu Gln Gln Lys Asn Phe Ile Thr Asp
        130                 135                 140
Leu Asp Lys Arg Ala Ile Asp Glu Ser Asp Ile Ile Met Thr Phe Leu
145                 150                 155                 160
Asn Lys Arg His His Asn Val Asp Glu Leu Arg His Glu His Gly Arg
                165                 170                 175
Arg Leu Trp Phe Asp Val Ser Asn Val Pro Asn Asp Asn Tyr Leu Val
                180                 185                 190
Met Ala Glu Leu Arg Ile Tyr Gln Asn Ala Asn Glu Gly Lys Trp Leu
            195                 200                 205
Thr Ala Asn Arg Glu Phe Thr Ile Thr Val Tyr Ala Ile Gly Thr Gly
        210                 215                 220
Thr Leu Gly Gln His Thr Met Glu Pro Leu Ser Ser Val Asn Thr Thr
225                 230                 235                 240
Gly Asp Tyr Val Gly Trp Leu Glu Leu Asn Val Thr Glu Gly Leu His
                245                 250                 255
Glu Trp Leu Val Lys Ser Lys Asp Asn His Gly Ile Tyr Ile Gly Ala
                260                 265                 270
His Ala Val Asn Arg Pro Asp Arg Glu Val Lys Leu Asp Asp Ile Gly
            275                 280                 285
Leu Ile His Arg Lys Val Asp Asp Glu Phe Gln Pro Phe Met Ile Gly
        290                 295                 300
Phe Phe Arg Gly Pro Glu Leu Ile Lys Ala Thr Ala His Ser Ser His
305                 310                 315                 320
His Arg Ser Lys Arg Ser Ala Ser His Pro Arg Lys Arg Lys Lys Ser
                325                 330                 335
Val Ser Pro Asn Asn Val Pro Leu Leu Glu Pro Met Glu Ser Thr Arg
                340                 345                 350
Ser Cys Gln Met Gln Thr Leu Tyr Ile Asp Phe Lys Asp Leu Gly Trp
            355                 360                 365
His Asp Trp Ile Ile Ala Pro Glu Gly Tyr Gly Ala Phe Tyr Cys Ser
        370                 375                 380
Gly Glu Cys Asn Phe Pro Leu Asn Ala His Met Asn Ala Thr Asn His
385                 390                 395                 400
```

Ala Ile Val Gln Thr Leu Val His Leu Leu Glu Pro Lys Lys Val Pro
            405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
            435                 440                 445

Val Lys Ser Cys Gly Cys His
            450                 455

<210> SEQ ID NO 26
<211> LENGTH: 104
<212> TYPE: PRT
<213> ORGANISM: Homo sapiens

<400> SEQUENCE: 26

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Ala Arg Ala Val Gly Val Val Pro Gly Ile
    50                  55                  60

Pro Glu Pro Cys Cys Val Pro Glu Lys Met Ser Ser Leu Ser Ile Leu
65                  70                  75                  80

Phe Phe Asp Glu Asn Lys Asn Val Val Leu Lys Val Tyr Pro Asn Met
                85                  90                  95

Thr Val Glu Ser Cys Ala Cys Arg
            100

<210> SEQ ID NO 27
<211> LENGTH: 102
<212> TYPE: PRT
<213> ORGANISM: Homo sapiens

<400> SEQUENCE: 27

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
    50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100

<210> SEQ ID NO 28
<211> LENGTH: 102
<212> TYPE: PRT
<213> ORGANISM: Homo sapiens

<400> SEQUENCE: 28

Cys Arg Lys His Glu Leu Tyr Val Ser Phe Gln Asp Leu Gly Trp Gln

```
                1               5                      10                      15
Asp Trp Ile Ile Ala Pro Lys Gly Tyr Ala Asn Tyr Cys Asp Gly
                    20                      25                      30

Glu Cys Ser Phe Pro Leu Asn Ala His Met Asn Ala Thr Asn His Ala
            35                      40                      45

Ile Val Gln Thr Leu Val His Leu Met Asn Pro Glu Tyr Val Pro Lys
        50                      55                      60

Pro Cys Cys Ala Pro Thr Lys Leu Asn Ala Ile Ser Val Leu Tyr Phe
65                      70                      75                      80

Asp Asp Asn Ser Asn Val Ile Leu Lys Lys Tyr Arg Asn Met Val Val
                    85                      90                      95

Arg Ala Cys Gly Cys His
            100

<210> SEQ ID NO 29
<211> LENGTH: 102
<212> TYPE: PRT
<213> ORGANISM: Artificial Sequence
<220> FEATURE:
<223> OTHER INFORMATION: Description of Artificial Sequence: Generic
      sequence OPX
<220> FEATURE:
<221> NAME/KEY: SITE
<222> LOCATION: (2)
<223> OTHER INFORMATION: Xaa=Lys or Arg
<220> FEATURE:
<221> NAME/KEY: SITE
<222> LOCATION: (3)
<223> OTHER INFORMATION: Xaa=Lys or Arg
<220> FEATURE:
<221> NAME/KEY: SITE
<222> LOCATION: (9)
<223> OTHER INFORMATION: Xaa=Ser, Asp or Glu
<220> FEATURE:
<221> NAME/KEY: SITE
<222> LOCATION: (11)
<223> OTHER INFORMATION: Xaa=Arg or Gln
<220> FEATURE:
<221> NAME/KEY: SITE
<222> LOCATION: (16)
<223> OTHER INFORMATION: Xaa=Gln or Leu
<220> FEATURE:
<221> NAME/KEY: SITE
<222> LOCATION: (19)
<223> OTHER INFORMATION: Xaa=Ile or Val
<220> FEATURE:
<221> NAME/KEY: SITE
<222> LOCATION: (23)
<223> OTHER INFORMATION: Xaa=Glu or Gln
<220> FEATURE:
<221> NAME/KEY: SITE
<222> LOCATION: (26)
<223> OTHER INFORMATION: Xaa=Ala or Ser
<220> FEATURE:
<221> NAME/KEY: SITE
<222> LOCATION: (35)
<223> OTHER INFORMATION: Xaa=Ala or Ser
<220> FEATURE:
<221> NAME/KEY: SITE
<222> LOCATION: (39)
<223> OTHER INFORMATION: Xaa=Asn or Asp
<220> FEATURE:
<221> NAME/KEY: SITE
<222> LOCATION: (41)
<223> OTHER INFORMATION: Xaa=Tyr or Cys
<220> FEATURE:
<221> NAME/KEY: SITE
<222> LOCATION: (50)
<223> OTHER INFORMATION: Xaa=Val or Leu
<220> FEATURE:
<221> NAME/KEY: SITE
<222> LOCATION: (52)
```

```
<223> OTHER INFORMATION: Xaa=Ser or Thr
<220> FEATURE:
<221> NAME/KEY: SITE
<222> LOCATION: (56)
<223> OTHER INFORMATION: Xaa=Phe or Leu
<220> FEATURE:
<221> NAME/KEY: SITE
<222> LOCATION: (57)
<223> OTHER INFORMATION: Xaa=Ile or Met
<220> FEATURE:
<221> NAME/KEY: SITE
<222> LOCATION: (58)
<223> OTHER INFORMATION: Xaa=Asn or Lys
<220> FEATURE:
<221> NAME/KEY: SITE
<222> LOCATION: (60)
<223> OTHER INFORMATION: Xaa=Glu, Asp or Asn
<220> FEATURE:
<221> NAME/KEY: SITE
<222> LOCATION: (61)
<223> OTHER INFORMATION: Xaa=Thr, Ala or Val
<220> FEATURE:
<221> NAME/KEY: SITE
<222> LOCATION: (65)
<223> OTHER INFORMATION: Xaa=Pro or Ala
<220> FEATURE:
<221> NAME/KEY: SITE
<222> LOCATION: (71)
<223> OTHER INFORMATION: Xaa=Gln or Lys
<220> FEATURE:
<221> NAME/KEY: SITE
<222> LOCATION: (73)
<223> OTHER INFORMATION: Xaa=Asn or Ser
<220> FEATURE:
<221> NAME/KEY: SITE
<222> LOCATION: (75)
<223> OTHER INFORMATION: Xaa=Ile or Thr
<220> FEATURE:
<221> NAME/KEY: SITE
<222> LOCATION: (80)
<223> OTHER INFORMATION: Xaa=Phe or Tyr
<220> FEATURE:
<221> NAME/KEY: SITE
<222> LOCATION: (82)
<223> OTHER INFORMATION: Xaa=Asp or Ser
<220> FEATURE:
<221> NAME/KEY: SITE
<222> LOCATION: (84)
<223> OTHER INFORMATION: Xaa=Ser or Asn
<220> FEATURE:
<221> NAME/KEY: SITE
<222> LOCATION: (89)
<223> OTHER INFORMATION: Xaa=Lys or Arg
<220> FEATURE:
<221> NAME/KEY: SITE
<222> LOCATION: (91)
<223> OTHER INFORMATION: Xaa=Tyr or His
<220> FEATURE:
<221> NAME/KEY: SITE
<222> LOCATION: (97)
<223> OTHER INFORMATION: Xaa=Arg or Lys

<400> SEQUENCE: 29

Cys Xaa Xaa His Glu Leu Tyr Val Xaa Phe Xaa Asp Leu Gly Trp Xaa
 1               5                  10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Val Pro Lys
    50                  55                  60

Xaa Cys Cys Ala Pro Thr Xaa Leu Xaa Ala Xaa Ser Val Leu Tyr Xaa
65                  70                  75                  80
```

```
Asp Xaa Ser Xaa Asn Val Xaa Leu Xaa Lys Xaa Arg Asn Met Val Val
            85                  90                  95

Xaa Ala Cys Gly Cys His
```

<210> SEQ ID NO 30
<211> LENGTH: 97
<212> TYPE: PRT
<213> ORGANISM: Artificial Sequence
<220> FEATURE:
<223> OTHER INFORMATION: Generic Sequence 5
<220> FEATURE:
<221> NAME/KEY: SITE
<222> LOCATION: (2)
<223> OTHER INFORMATION: Xaa=Tyr or Lys
<220> FEATURE:
<221> NAME/KEY: SITE
<222> LOCATION: (3)
<223> OTHER INFORMATION: Xaa=Val or Ile
<220> FEATURE:
<221> NAME/KEY: SITE
<222> LOCATION: (4)
<223> OTHER INFORMATION: Xaa=Ser, Asp or Glu
<220> FEATURE:
<221> NAME/KEY: SITE
<222> LOCATION: (6)
<223> OTHER INFORMATION: Xaa=Arg, Gln, Ser, Lys, or Ala
<220> FEATURE:
<221> NAME/KEY: SITE
<222> LOCATION: (7)
<223> OTHER INFORMATION: Xaa=Asp or Glu
<220> FEATURE:
<221> NAME/KEY: SITE
<222> LOCATION: (8)
<223> OTHER INFORMATION: Xaa=Leu, Val or Ile
<220> FEATURE:
<221> NAME/KEY: SITE
<222> LOCATION: (11)
<223> OTHER INFORMATION: Xaa=Gln, Leu, Asp, His, Asn, or Ser
<220> FEATURE:
<221> NAME/KEY: SITE
<222> LOCATION: (12)
<223> OTHER INFORMATION: Xaa=Asp, Arg, Asn, or Glu
<220> FEATURE:
<221> NAME/KEY: SITE
<222> LOCATION: (13)
<223> OTHER INFORMATION: Xaa=Trp or Ser
<220> FEATURE:
<221> NAME/KEY: SITE
<222> LOCATION: (14)
<223> OTHER INFORMATION: Xaa=Ile or Val
<220> FEATURE:
<221> NAME/KEY: SITE
<222> LOCATION: (15)
<223> OTHER INFORMATION: Xaa=Ile or Val
<220> FEATURE:
<221> NAME/KEY: SITE
<222> LOCATION: (16)
<223> OTHER INFORMATION: Xaa=Ala or Ser
<220> FEATURE:
<221> NAME/KEY: SITE
<222> LOCATION: (18)
<223> OTHER INFORMATION: Xaa=Glu, Gln, Leu, Lys, Pro, or Arg
<220> FEATURE:
<221> NAME/KEY: SITE
<222> LOCATION: (19)
<223> OTHER INFORMATION: Xaa=Gly or Ser
<220> FEATURE:
<221> NAME/KEY: SITE
<222> LOCATION: (20)
<223> OTHER INFORMATION: Xaa=Tyr or Phe
<220> FEATURE:
<221> NAME/KEY: SITE
<222> LOCATION: (21)
<223> OTHER INFORMATION: Xaa=Ala, Ser, Asp, Met, His, Gln, Leu, or Gly
<220> FEATURE:
<221> NAME/KEY: SITE
<222> LOCATION: (23)

```
<223> OTHER INFORMATION: Xaa=Tyr, Asn, or Phe
<220> FEATURE:
<221> NAME/KEY: SITE
<222> LOCATION: (26)
<223> OTHER INFORMATION: Xaa=Glu, His, Tyr, Asp, Gln, Leu, or Gly
<220> FEATURE:
<221> NAME/KEY: SITE
<222> LOCATION: (28)
<223> OTHER INFORMATION: Xaa=Glu, Lys, Asp, Gln, or Ala
<220> FEATURE:
<221> NAME/KEY: SITE
<222> LOCATION: (30)
<223> OTHER INFORMATION: Xaa=Ala, Ser, Pro, Gln, Ile, or Asn
<220> FEATURE:
<221> NAME/KEY: SITE
<222> LOCATION: (31)
<223> OTHER INFORMATION: Xaa=Phe, Leu or Tyr
<220> FEATURE:
<221> NAME/KEY: SITE
<222> LOCATION: (33)
<223> OTHER INFORMATION: Xaa=Leu, Val or Met
<220> FEATURE:
<221> NAME/KEY: SITE
<222> LOCATION: (34)
<223> OTHER INFORMATION: Xaa=Asn, Asp, Ala, Thr, or Pro
<220> FEATURE:
<221> NAME/KEY: SITE
<222> LOCATION: (35)
<223> OTHER INFORMATION: Xaa=Ser, Asp, Glu, Leu, Ala, or Lys
<220> FEATURE:
<221> NAME/KEY: SITE
<222> LOCATION: (36)
<223> OTHER INFORMATION: Xaa=Tyr, Cys, His, Ser, or Ile
<220> FEATURE:
<221> NAME/KEY: SITE
<222> LOCATION: (37)
<223> OTHER INFORMATION: Xaa=Met, Phe, Gly, or Leu
<220> FEATURE:
<221> NAME/KEY: SITE
<222> LOCATION: (38)
<223> OTHER INFORMATION: Xaa=Asn, Ser or Lys
<220> FEATURE:
<221> NAME/KEY: SITE
<222> LOCATION: (39)
<223> OTHER INFORMATION: Xaa=Ala, Ser, Gly, or Pro
<220> FEATURE:
<221> NAME/KEY: SITE
<222> LOCATION: (40)
<223> OTHER INFORMATION: Xaa=Thr, Leu or Ser
<220> FEATURE:
<221> NAME/KEY: SITE
<222> LOCATION: (44)
<223> OTHER INFORMATION: Xaa=Ile, Val or Thr
<220> FEATURE:
<221> NAME/KEY: SITE
<222> LOCATION: (45)
<223> OTHER INFORMATION: Xaa=Val, Leu, Met, or Ile
<220> FEATURE:
<221> NAME/KEY: SITE
<222> LOCATION: (46)
<223> OTHER INFORMATION: Xaa=Gln or Arg
<220> FEATURE:
<221> NAME/KEY: SITE
<222> LOCATION: (47)
<223> OTHER INFORMATION: Xaa=Thr, Ala or Ser
<220> FEATURE:
<221> NAME/KEY: SITE
<222> LOCATION: (48)
<223> OTHER INFORMATION: Xaa=Leu or Ile
<220> FEATURE:
<221> NAME/KEY: SITE
<222> LOCATION: (49)
<223> OTHER INFORMATION: Xaa=Val or Met
<220> FEATURE:
<221> NAME/KEY: SITE
<222> LOCATION: (50)
<223> OTHER INFORMATION: Xaa=His, Asn or Arg
<220> FEATURE:
<221> NAME/KEY: SITE
```

```
<222> LOCATION: (51)
<223> OTHER INFORMATION: Xaa=Phe, Leu, Asn, Ser, Ala, or Val
<220> FEATURE:
<221> NAME/KEY: SITE
<222> LOCATION: (52)
<223> OTHER INFORMATION: Xaa=Ile, Met, Asn, Ala, Val, Gly, or Leu
<220> FEATURE:
<221> NAME/KEY: SITE
<222> LOCATION: (53)
<223> OTHER INFORMATION: Xaa=Asn, Lys, Ala, Glu, Gly, or Phe
<220> FEATURE:
<221> NAME/KEY: SITE
<222> LOCATION: (54)
<223> OTHER INFORMATION: Xaa=Pro, Ser or Val
<220> FEATURE:
<221> NAME/KEY: SITE
<222> LOCATION: (55)
<223> OTHER INFORMATION: Xaa=Glu, Asp, Asn, Gly, Val, Pro, or Lys
<220> FEATURE:
<221> NAME/KEY: SITE
<222> LOCATION: (56)
<223> OTHER INFORMATION: Xaa=Thr, Ala, Val, Lys, Asp, Tyr, Ser, Gly,
      Ile, or His
<220> FEATURE:
<221> NAME/KEY: SITE
<222> LOCATION: (57)
<223> OTHER INFORMATION: Xaa=Val, Ala or Ile
<220> FEATURE:
<221> NAME/KEY: SITE
<222> LOCATION: (58)
<223> OTHER INFORMATION: Xaa=Pro or Asp
<220> FEATURE:
<221> NAME/KEY: SITE
<222> LOCATION: (59)
<223> OTHER INFORMATION: Xaa=Lys, Leu or Glu
<220> FEATURE:
<221> NAME/KEY: SITE
<222> LOCATION: (60)
<223> OTHER INFORMATION: Xaa=Pro, Val or Ala
<220> FEATURE:
<221> NAME/KEY: SITE
<222> LOCATION: (63)
<223> OTHER INFORMATION: Xaa=Ala or Val
<220> FEATURE:
<221> NAME/KEY: SITE
<222> LOCATION: (65)
<223> OTHER INFORMATION: Xaa=Thr, Ala or Glu
<220> FEATURE:
<221> NAME/KEY: SITE
<222> LOCATION: (66)
<223> OTHER INFORMATION: Xaa=Gln, Lys, Arg, or Glu
<220> FEATURE:
<221> NAME/KEY: SITE
<222> LOCATION: (67)
<223> OTHER INFORMATION: Xaa=Leu, Met or Val
<220> FEATURE:
<221> NAME/KEY: SITE
<222> LOCATION: (68)
<223> OTHER INFORMATION: Xaa=Asn, Ser, Asp, or Gly
<220> FEATURE:
<221> NAME/KEY: SITE
<222> LOCATION: (69)
<223> OTHER INFORMATION: Xaa=Ala, Pro or Ser
<220> FEATURE:
<221> NAME/KEY: SITE
<222> LOCATION: (70)
<223> OTHER INFORMATION: Xaa=Ile, Thr, Val, or Leu
<220> FEATURE:
<221> NAME/KEY: SITE
<222> LOCATION: (71)
<223> OTHER INFORMATION: Xaa=Ser, Ala or Pro
<220> FEATURE:
<221> NAME/KEY: SITE
<222> LOCATION: (72)
<223> OTHER INFORMATION: Xaa=Val, Leu, Met, or Ile
<220> FEATURE:
<221> NAME/KEY: SITE
<222> LOCATION: (74)
<223> OTHER INFORMATION: Xaa=Tyr or Phe
```

```
<220> FEATURE:
<221> NAME/KEY: SITE
<222> LOCATION: (75)
<223> OTHER INFORMATION: Xaa=Phe, Tyr, Leu, or His
<220> FEATURE:
<221> NAME/KEY: SITE
<222> LOCATION: (76)
<223> OTHER INFORMATION: Xaa=Asp, Asn or Leu
<220> FEATURE:
<221> NAME/KEY: SITE
<222> LOCATION: (77)
<223> OTHER INFORMATION: Xaa=Asp, Glu, Asn, Arg, or Ser
<220> FEATURE:
<221> NAME/KEY: SITE
<222> LOCATION: (78)
<223> OTHER INFORMATION: Xaa=Ser, Gln, Asn, Tyr, or Asp
<220> FEATURE:
<221> NAME/KEY: SITE
<222> LOCATION: (79)
<223> OTHER INFORMATION: Xaa=Ser, Asn, Asp, Glu, or Lys
<220> FEATURE:
<221> NAME/KEY: SITE
<222> LOCATION: (80)
<223> OTHER INFORMATION: Xaa=Asn, Thr or Lys
<220> FEATURE:
<221> NAME/KEY: SITE
<222> LOCATION: (82)
<223> OTHER INFORMATION: Xaa=Ile, Val or Asn
<220> FEATURE:
<221> NAME/KEY: SITE
<222> LOCATION: (84)
<223> OTHER INFORMATION: Xaa=Lys or Arg
<220> FEATURE:
<221> NAME/KEY: SITE
<222> LOCATION: (85)
<223> OTHER INFORMATION: Xaa=Lys, Asn, Gln, His, Arg, or Val
<220> FEATURE:
<221> NAME/KEY: SITE
<222> LOCATION: (86)
<223> OTHER INFORMATION: Xaa=Tyr, Glu or His
<220> FEATURE:
<221> NAME/KEY: SITE
<222> LOCATION: (87)
<223> OTHER INFORMATION: Xaa=Arg, Gln, Glu, or Pro
<220> FEATURE:
<221> NAME/KEY: SITE
<222> LOCATION: (88)
<223> OTHER INFORMATION: Xaa=Asn, Glu, Trp, or Asp
<220> FEATURE:
<221> NAME/KEY: SITE
<222> LOCATION: (90)
<223> OTHER INFORMATION: Xaa=Val, Thr, Ala, or Ile
<220> FEATURE:
<221> NAME/KEY: SITE
<222> LOCATION: (92)
<223> OTHER INFORMATION: Xaa=Arg, Lys, Val, Asp, Gln, or Glu
<220> FEATURE:
<221> NAME/KEY: SITE
<222> LOCATION: (93)
<223> OTHER INFORMATION: Xaa=Ala, Gly, Glu, or Ser
<220> FEATURE:
<221> NAME/KEY: SITE
<222> LOCATION: (95)
<223> OTHER INFORMATION: Xaa=Gly or Ala
<220> FEATURE:
<221> NAME/KEY: SITE
<222> LOCATION: (97)
<223> OTHER INFORMATION: Xaa=His or Arg

<400> SEQUENCE: 30

Leu Xaa Xaa Xaa Phe Xaa Xaa Xaa Gly Trp Xaa Xaa Trp Xaa Xaa Xaa
 1               5                  10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Xaa
        35                  40                  45
```

```
Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95

Xaa

<210> SEQ ID NO 31
<211> LENGTH: 102
<212> TYPE: PRT
<213> ORGANISM: Artificial Sequence
<220> FEATURE:
<223> OTHER INFORMATION: Description of Artificial Sequence: Generic
      sequence 6
<220> FEATURE:
<221> NAME/KEY: SITE
<222> LOCATION: (2)
<223> OTHER INFORMATION: Xaa=Lys, Arg, Ala, or Gln
<220> FEATURE:
<221> NAME/KEY: SITE
<222> LOCATION: (3)
<223> OTHER INFORMATION: Xaa=Lys, Arg or Met
<220> FEATURE:
<221> NAME/KEY: SITE
<222> LOCATION: (4)
<223> OTHER INFORMATION: Xaa=His, Arg or Gln
<220> FEATURE:
<221> NAME/KEY: SITE
<222> LOCATION: (5)
<223> OTHER INFORMATION: Xaa=Glu, Ser, His, Gly, Arg, Pro, Thr, or Tyr
<220> FEATURE:
<221> NAME/KEY: SITE
<222> LOCATION: (7)
<223> OTHER INFORMATION: Xaa=Tyr or Lys
<220> FEATURE:
<221> NAME/KEY: SITE
<222> LOCATION: (8)
<223> OTHER INFORMATION: Xaa=Val or Ile
<220> FEATURE:
<221> NAME/KEY: SITE
<222> LOCATION: (9)
<223> OTHER INFORMATION: Xaa=Ser, Asp or Glu
<220> FEATURE:
<221> NAME/KEY: SITE
<222> LOCATION: (11)
<223> OTHER INFORMATION: Xa=Arg, Gln, Ser, Lys, or Ala
<220> FEATURE:
<221> NAME/KEY: SITE
<222> LOCATION: (12)
<223> OTHER INFORMATION: Xaa=Asp or Glu
<220> FEATURE:
<221> NAME/KEY: SITE
<222> LOCATION: (13)
<223> OTHER INFORMATION: Xaa=Leu, Val or Ile
<220> FEATURE:
<221> NAME/KEY: SITE
<222> LOCATION: (16)
<223> OTHER INFORMATION: Xaa=Gln, Leu, Asp, His, Asn, or Ser
<220> FEATURE:
<221> NAME/KEY: SITE
<222> LOCATION: (17)
<223> OTHER INFORMATION: Xaa=Asp, Arg, Asn, or Glu
<220> FEATURE:
<221> NAME/KEY: SITE
<222> LOCATION: (18)
<223> OTHER INFORMATION: Xaa=Trp or Ser
<220> FEATURE:
<221> NAME/KEY: SITE
<222> LOCATION: (19)
<223> OTHER INFORMATION: Xaa=Ile or Val
<220> FEATURE:
<221> NAME/KEY: SITE
<222> LOCATION: (20)
```

```
<223> OTHER INFORMATION: Xaa=Tyr or Phe
<220> FEATURE:
<221> NAME/KEY: SITE
<222> LOCATION: (21)
<223> OTHER INFORMATION: Xaa=Ala or Ser
<220> FEATURE:
<221> NAME/KEY: SITE
<222> LOCATION: (23)
<223> OTHER INFORMATION: Xaa=Glu, Gln, Leu, Lys, Pro, or Arg
<220> FEATURE:
<221> NAME/KEY: SITE
<222> LOCATION: (24)
<223> OTHER INFORMATION: Xaa=Gly or Ser
<220> FEATURE:
<221> NAME/KEY: SITE
<222> LOCATION: (25)
<223> OTHER INFORMATION: Xaa=Tyr or Phe
<220> FEATURE:
<221> NAME/KEY: SITE
<222> LOCATION: (26)
<223> OTHER INFORMATION: Xaa=Ala, Ser, Asp, Met, His, Gln, Leu, or Gly
<220> FEATURE:
<221> NAME/KEY: SITE
<222> LOCATION: (28)
<223> OTHER INFORMATION: Xaa=Tyr, Asn or Phe
<220> FEATURE:
<221> NAME/KEY: SITE
<222> LOCATION: (31)
<223> OTHER INFORMATION: Xaa=Glu, His, Tyr, Asp, Gln, Ala, or Ser
<220> FEATURE:
<221> NAME/KEY: SITE
<222> LOCATION: (33)
<223> OTHER INFORMATION: Xaa=Glu, Lys, Asp, Gln, or Ala
<220> FEATURE:
<221> NAME/KEY: SITE
<222> LOCATION: (35)
<223> OTHER INFORMATION: Xaa=Ala, Ser, Pro, Gln, Ile, or Asn
<220> FEATURE:
<221> NAME/KEY: SITE
<222> LOCATION: (36)
<223> OTHER INFORMATION: Xaa=Phe, Leu or Tyr
<220> FEATURE:
<221> NAME/KEY: SITE
<222> LOCATION: (38)
<223> OTHER INFORMATION: Xaa=Leu, Val or Met
<220> FEATURE:
<221> NAME/KEY: SITE
<222> LOCATION: (39)
<223> OTHER INFORMATION: Xaa=Asn, Asp, Ala, Thr, or Pro
<220> FEATURE:
<221> NAME/KEY: SITE
<222> LOCATION: (40)
<223> OTHER INFORMATION: Xaa=Ser, Asp, Glu, Leu, Ala, or Lys
<220> FEATURE:
<221> NAME/KEY: SITE
<222> LOCATION: (41)
<223> OTHER INFORMATION: Xaa=Tyr, Cys, His, Ser, or Ile
<220> FEATURE:
<221> NAME/KEY: SITE
<222> LOCATION: (42)
<223> OTHER INFORMATION: Xaa=Met, Phe, Gly, or Leu
<220> FEATURE:
<221> NAME/KEY: SITE
<222> LOCATION: (43)
<223> OTHER INFORMATION: Xaa=Asn, Ser, or Lys
<220> FEATURE:
<221> NAME/KEY: SITE
<222> LOCATION: (44)
<223> OTHER INFORMATION: Xaa=Ala, Ser, Gly, or Pro
<220> FEATURE:
<221> NAME/KEY: SITE
<222> LOCATION: (45)
<223> OTHER INFORMATION: Xaa=Thr, Leu or Ser
<220> FEATURE:
<221> NAME/KEY: SITE
<222> LOCATION: (49)
<223> OTHER INFORMATION: Xaa=Ile, Val or Thr
<220> FEATURE:
<221> NAME/KEY: SITE
```

-continued

```
<222> LOCATION: (50)
<223> OTHER INFORMATION: Xaa=Val, Leu, Met, or Ile
<220> FEATURE:
<221> NAME/KEY: SITE
<222> LOCATION: (51)
<223> OTHER INFORMATION: Xaa=Gln or Arg
<220> FEATURE:
<221> NAME/KEY: SITE
<222> LOCATION: (52)
<223> OTHER INFORMATION: Xaa=Thr, Ala or Ser
<220> FEATURE:
<221> NAME/KEY: SITE
<222> LOCATION: (53)
<223> OTHER INFORMATION: Xaa=Leu or Ile
<220> FEATURE:
<221> NAME/KEY: SITE
<222> LOCATION: (54)
<223> OTHER INFORMATION: Xaa=Val or Met
<220> FEATURE:
<221> NAME/KEY: SITE
<222> LOCATION: (55)
<223> OTHER INFORMATION: Xaa=His, Asn or Arg
<220> FEATURE:
<221> NAME/KEY: SITE
<222> LOCATION: (56)
<223> OTHER INFORMATION: Xaa=Phe, Leu, Asn, Ser, Ala, or Val
<220> FEATURE:
<221> NAME/KEY: SITE
<222> LOCATION: (57)
<223> OTHER INFORMATION: Xaa=Ile, Met, Asn, Ala, Val, Gly, or Leu
<220> FEATURE:
<221> NAME/KEY: SITE
<222> LOCATION: (58)
<223> OTHER INFORMATION: Xaa=Asn, Lys, Ala, Glu, Gly, or Phe
<220> FEATURE:
<221> NAME/KEY: SITE
<222> LOCATION: (59)
<223> OTHER INFORMATION: Xaa=Pro, Ser or Val
<220> FEATURE:
<221> NAME/KEY: SITE
<222> LOCATION: (60)
<223> OTHER INFORMATION: Xaa=Glu, Asp, Asn, Gly, Val, Pro, or Lys
<220> FEATURE:
<221> NAME/KEY: SITE
<222> LOCATION: (61)
<223> OTHER INFORMATION: Xaa=Thr, Ala, Val, Lys, Asp, Tyr, Ser, Gly,
      Ile, or His
<220> FEATURE:
<221> NAME/KEY: SITE
<222> LOCATION: (62)
<223> OTHER INFORMATION: Xaa=Val, Ala or Ile
<220> FEATURE:
<221> NAME/KEY: SITE
<222> LOCATION: (63)
<223> OTHER INFORMATION: Xaa=Pro or Asp
<220> FEATURE:
<221> NAME/KEY: SITE
<222> LOCATION: (64)
<223> OTHER INFORMATION: Xaa=Lys, Leu or Glu
<220> FEATURE:
<221> NAME/KEY: SITE
<222> LOCATION: (65)
<223> OTHER INFORMATION: Xaa=Pro, Val or Ala
<220> FEATURE:
<221> NAME/KEY: SITE
<222> LOCATION: (68)
<223> OTHER INFORMATION: Xaa=Ala or Val
<220> FEATURE:
<221> NAME/KEY: SITE
<222> LOCATION: (70)
<223> OTHER INFORMATION: Xaa=Thr, Ala or Glu
<220> FEATURE:
<221> NAME/KEY: SITE
<222> LOCATION: (71)
<223> OTHER INFORMATION: Xaa=Gln, Lys, Arg, or Glu
<220> FEATURE:
<221> NAME/KEY: SITE
<222> LOCATION: (72)
<223> OTHER INFORMATION: Xaa=Leu, Met or Val
```

```
<220> FEATURE:
<221> NAME/KEY: SITE
<222> LOCATION: (73)
<223> OTHER INFORMATION: Xaa=Asn, Ser, Asp, or Gly
<220> FEATURE:
<221> NAME/KEY: SITE
<222> LOCATION: (74)
<223> OTHER INFORMATION: Xaa=Ala, Pro or Ser
<220> FEATURE:
<221> NAME/KEY: SITE
<222> LOCATION: (75)
<223> OTHER INFORMATION: Xaa=Ile, Thr, Val, or Leu
<220> FEATURE:
<221> NAME/KEY: SITE
<222> LOCATION: (76)
<223> OTHER INFORMATION: Xaa=Ser, Ala or Pro
<220> FEATURE:
<221> NAME/KEY: SITE
<222> LOCATION: (77)
<223> OTHER INFORMATION: Xaa=Val, Leu, Met, or Ile
<220> FEATURE:
<221> NAME/KEY: SITE
<222> LOCATION: (79)
<223> OTHER INFORMATION: Xaa=Tyr or Phe
<220> FEATURE:
<221> NAME/KEY: SITE
<222> LOCATION: (80)
<223> OTHER INFORMATION: Xaa=Phe, Tyr, Leu, or His
<220> FEATURE:
<221> NAME/KEY: SITE
<222> LOCATION: (81)
<223> OTHER INFORMATION: Xaa=Asp, Asn or Leu
<220> FEATURE:
<221> NAME/KEY: SITE
<222> LOCATION: (82)
<223> OTHER INFORMATION: Xaa=Asp, Glu, Asn, Arg, or Ser
<220> FEATURE:
<221> NAME/KEY: SITE
<222> LOCATION: (83)
<223> OTHER INFORMATION: Xaa=Ser, Gln, Asn, Tyr, or Asp
<220> FEATURE:
<221> NAME/KEY: SITE
<222> LOCATION: (84)
<223> OTHER INFORMATION: Xaa=Ser, Asn, Asp, Glu, or Lys
<220> FEATURE:
<221> NAME/KEY: SITE
<222> LOCATION: (85)
<223> OTHER INFORMATION: Xaa=Asn, Thr or Lys
<220> FEATURE:
<221> NAME/KEY: SITE
<222> LOCATION: (87)
<223> OTHER INFORMATION: Xaa=Ile, Val or Asn
<220> FEATURE:
<221> NAME/KEY: SITE
<222> LOCATION: (89)
<223> OTHER INFORMATION: Xaa=Lys or Arg
<220> FEATURE:
<221> NAME/KEY: SITE
<222> LOCATION: (90)
<223> OTHER INFORMATION: Xaa=Lys, Asn, Gln, His, Arg, or Val
<220> FEATURE:
<221> NAME/KEY: SITE
<222> LOCATION: (91)
<223> OTHER INFORMATION: Xaa=Tyr, Glu or His
<220> FEATURE:
<221> NAME/KEY: SITE
<222> LOCATION: (92)
<223> OTHER INFORMATION: Xaa=Arg, Gln, Glu, or Pro
<220> FEATURE:
<221> NAME/KEY: SITE
<222> LOCATION: (93)
<223> OTHER INFORMATION: Xaa=Asn, Glu, Trp, or Asp
<220> FEATURE:
<221> NAME/KEY: SITE
<222> LOCATION: (95)
<223> OTHER INFORMATION: Xaa=Val, Thr, Ala, or Ile
<220> FEATURE:
<221> NAME/KEY: SITE
<222> LOCATION: (97)
```

-continued

```
<223> OTHER INFORMATION: Xaa=Arg, Lys, Val, Asp, Gln, or Glu
<220> FEATURE:
<221> NAME/KEY: SITE
<222> LOCATION: (98)
<223> OTHER INFORMATION: Xaa=Ala, Gly, Glu, or Ser
<220> FEATURE:
<221> NAME/KEY: SITE
<222> LOCATION: (100)
<223> OTHER INFORMATION: Xaa=Gly or Ala
<220> FEATURE:
<221> NAME/KEY: SITE
<222> LOCATION: (102)
<223> OTHER INFORMATION: Xaa=His or Arg

<400> SEQUENCE: 31

Cys Xaa Xaa Xaa Xaa Leu Xaa Xaa Xaa Phe Xaa Xaa Xaa Gly Trp Xaa
 1               5                  10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
 65              70                  75                  80

Xaa Xaa Xaa Xaa Xaa Val Xaa Leu Xaa Xaa Xaa Xaa Met Xaa Val
                85                  90                  95

Xaa Xaa Cys Xaa Cys Xaa
            100

<210> SEQ ID NO 32
<211> LENGTH: 1247
<212> TYPE: DNA
<213> ORGANISM: Homo sapiens
<220> FEATURE:
<221> NAME/KEY: CDS
<222> LOCATION: (84)..(1202)
<223> OTHER INFORMATION:

<400> SEQUENCE: 32
ggggacaccg gccccgccct cagcccactg gtcccgggcc gccgcggacc ctgcgcactc     60
tctggtcatc gcctgggagg aag atg cca ccg ccg cag caa ggt ccc tgc ggc    113
                         Met Pro Pro Pro Gln Gln Gly Pro Cys Gly
                          1               5                  10 cac cac ctc ctc ctc ctc ctg gcc ctg ctg ctg ccc tcg ctg ccc ctg      161
His His Leu Leu Leu Leu Leu Ala Leu Leu Leu Pro Ser Leu Pro Leu
                15                  20                  25 acc cgc gcc ccc gtg ccc cca ggc cca gcc gcc gcc ctg ctc cag gct      209
Thr Arg Ala Pro Val Pro Pro Gly Pro Ala Ala Ala Leu Leu Gln Ala
            30                  35                  40 cta gga ctg cgc gat gag ccc cag ggt gcc ccc agg ctc cgg ccg gtt      257
Leu Gly Leu Arg Asp Glu Pro Gln Gly Ala Pro Arg Leu Arg Pro Val
        45                  50                  55 ccc ccg gtc atg tgg cgc ctg ttt cga cgc cgg gac ccc cag gag acc      305
Pro Pro Val Met Trp Arg Leu Phe Arg Arg Arg Asp Pro Gln Glu Thr
    60                  65                  70 agg tct ggc tcg cgg cgg acg tcc cca ggg gtc acc ctg caa ccg tgc      353
Arg Ser Gly Ser Arg Arg Thr Ser Pro Gly Val Thr Leu Gln Pro Cys
 75                  80                  85                  90 cac gtg gag gag ctg ggg gtc gcc gga aac atc gtg cgc cac atc ccg      401
His Val Glu Glu Leu Gly Val Ala Gly Asn Ile Val Arg His Ile Pro
                 95                 100                 105
```

```
gac cgc ggt gcg ccc acc cgg gcc tcg gag cct gtc tcg gcc gcg ggg      449
Asp Arg Gly Ala Pro Thr Arg Ala Ser Glu Pro Val Ser Ala Ala Gly
            110                 115                 120 cat tgc cct gag tgg aca gtc gtc ttc gac ctg tcg gct gtg gaa ccc      497
His Cys Pro Glu Trp Thr Val Val Phe Asp Leu Ser Ala Val Glu Pro
        125                 130                 135 gct gag cgc ccg agc cgg gcc cgc ctg gag ctg cgt ttc gcg gcg gcg      545
Ala Glu Arg Pro Ser Arg Ala Arg Leu Glu Leu Arg Phe Ala Ala Ala
    140                 145                 150 gcg gcg gca gcc ccg gag ggc ggc tgg gag ctg agc gtg gca caa gcg      593
Ala Ala Ala Ala Pro Glu Gly Gly Trp Glu Leu Ser Val Ala Gln Ala
155                 160                 165                 170 ggc cag ggc gcg ggc gcg gac ccc ggg ccg gtg ctc ctc cgc cag ttg      641
Gly Gln Gly Ala Gly Ala Asp Pro Gly Pro Val Leu Leu Arg Gln Leu
                175                 180                 185 gtg ccc gcc ctg ggg ccg cca gtg cgc gcg gag ctg ctg ggc gcc gct      689
Val Pro Ala Leu Gly Pro Pro Val Arg Ala Glu Leu Leu Gly Ala Ala
            190                 195                 200 tgg gct cgc aac gcc tca tgg ccg cgc agc ctc cgc ctg gcg ctg gcg      737
Trp Ala Arg Asn Ala Ser Trp Pro Arg Ser Leu Arg Leu Ala Leu Ala
        205                 210                 215 cta cgc ccc cgg gcc cct gcc gcc tgc gcg cgc ctg gcc gag gcc tcg      785
Leu Arg Pro Arg Ala Pro Ala Ala Cys Ala Arg Leu Ala Glu Ala Ser
    220                 225                 230 ctg ctg ctg gtg acc ctc gac ccg cgc ctg tgc cac ccc ctg gcc cgg      833
Leu Leu Leu Val Thr Leu Asp Pro Arg Leu Cys His Pro Leu Ala Arg
235                 240                 245                 250 ccg cgg cgc gac gcc gaa ccc gtg ttg ggc ggc ggc ccc ggg ggc gct      881
Pro Arg Arg Asp Ala Glu Pro Val Leu Gly Gly Gly Pro Gly Gly Ala
                255                 260                 265 tgt cgc gcg cgg cgg ctg tac gtg agc ttc cgc gag gtg ggc tgg cac      929
Cys Arg Ala Arg Arg Leu Tyr Val Ser Phe Arg Glu Val Gly Trp His
            270                 275                 280 cgc tgg gtc atc gcg ccg cgc ggc ttc ctg gcc aac tac tgc cag ggt      977
Arg Trp Val Ile Ala Pro Arg Gly Phe Leu Ala Asn Tyr Cys Gln Gly
        285                 290                 295 cag tgc gcg ctg ccc gtc gcg ctg tcg ggg tcc ggg ggg ccg ccg gcg     1025
Gln Cys Ala Leu Pro Val Ala Leu Ser Gly Ser Gly Gly Pro Pro Ala
    300                 305                 310 ctc aac cac gct gtg ctg cgc gcg ctc atg cac gcg gcc gcc ccg gga     1073
Leu Asn His Ala Val Leu Arg Ala Leu Met His Ala Ala Ala Pro Gly
315                 320                 325                 330 gcc gcc gac ctg ccc tgc tgc gtg ccc gcg cgc ctg tcg ccc atc tcc     1121
Ala Ala Asp Leu Pro Cys Cys Val Pro Ala Arg Leu Ser Pro Ile Ser
                335                 340                 345 gtg ctc ttc ttt gac aac agc gac aac gtg gtg ctg cgg cag tat gag     1169
Val Leu Phe Phe Asp Asn Ser Asp Asn Val Val Leu Arg Gln Tyr Glu
            350                 355                 360 gac atg gtg gtg gac gag tgc ggc tgc cgc taa cccggggcgg gcagggaccc   1222
Asp Met Val Val Asp Glu Cys Gly Cys Arg
        365                 370 gggcccaaca ataaatgccg cgtgg                                         1247

<210> SEQ ID NO 33
<211> LENGTH: 372
<212> TYPE: PRT
<213> ORGANISM: Homo sapiens

<400> SEQUENCE: 33

Met Pro Pro Pro Gln Gln Gly Pro Cys Gly His His Leu Leu Leu Leu
```

-continued

| | | | | | | | | | | | | | | | |
|---|---|---|---|---|---|---|---|---|---|---|---|---|---|---|---|
| 1 | | | | 5 | | | | | 10 | | | | | 15 | |
| Leu | Ala | Leu | Leu | Leu | Pro | Ser | Leu | Pro | Leu | Thr | Arg | Ala | Pro | Val | Pro |
| | | 20 | | | | | 25 | | | | | 30 | | | |
| Pro | Gly | Pro | Ala | Ala | Ala | Leu | Leu | Gln | Ala | Leu | Gly | Leu | Arg | Asp | Glu |
| | | 35 | | | | | 40 | | | | | 45 | | | |
| Pro | Gln | Gly | Ala | Pro | Arg | Leu | Arg | Pro | Val | Pro | Val | Met | Trp | Arg | |
| | | 50 | | | | | 55 | | | | | 60 | | | |
| Leu | Phe | Arg | Arg | Arg | Asp | Pro | Gln | Glu | Thr | Arg | Ser | Gly | Ser | Arg | Arg |
| 65 | | | | | 70 | | | | | 75 | | | | | 80 |
| Thr | Ser | Pro | Gly | Val | Thr | Leu | Gln | Pro | Cys | His | Val | Glu | Glu | Leu | Gly |
| | | | | 85 | | | | | 90 | | | | | 95 | |
| Val | Ala | Gly | Asn | Ile | Val | Arg | His | Ile | Pro | Asp | Arg | Gly | Ala | Pro | Thr |
| | | | 100 | | | | | 105 | | | | | 110 | | |
| Arg | Ala | Ser | Glu | Pro | Val | Ser | Ala | Ala | Gly | His | Cys | Pro | Glu | Trp | Thr |
| | | | 115 | | | | | 120 | | | | | 125 | | |
| Val | Val | Phe | Asp | Leu | Ser | Ala | Val | Glu | Pro | Ala | Glu | Arg | Pro | Ser | Arg |
| | | | 130 | | | | | 135 | | | | | 140 | | |
| Ala | Arg | Leu | Glu | Leu | Arg | Phe | Ala | Ala | Ala | Ala | Ala | Ala | Ala | Pro | Glu |
| 145 | | | | | 150 | | | | | 155 | | | | | 160 |
| Gly | Gly | Trp | Glu | Leu | Ser | Val | Ala | Gln | Ala | Gly | Gln | Gly | Ala | Gly | Ala |
| | | | | 165 | | | | | 170 | | | | | 175 | |
| Asp | Pro | Gly | Pro | Val | Leu | Leu | Arg | Gln | Leu | Val | Pro | Ala | Leu | Gly | Pro |
| | | | 180 | | | | | 185 | | | | | 190 | | |
| Pro | Val | Arg | Ala | Glu | Leu | Leu | Gly | Ala | Ala | Trp | Ala | Arg | Asn | Ala | Ser |
| | | 195 | | | | | 200 | | | | | 205 | | | |
| Trp | Pro | Arg | Ser | Leu | Arg | Leu | Ala | Leu | Ala | Leu | Arg | Pro | Arg | Ala | Pro |
| | | 210 | | | | | 215 | | | | | 220 | | | |
| Ala | Ala | Cys | Ala | Arg | Leu | Ala | Glu | Ala | Ser | Leu | Leu | Leu | Val | Thr | Leu |
| 225 | | | | | 230 | | | | | 235 | | | | | 240 |
| Asp | Pro | Arg | Leu | Cys | His | Pro | Leu | Ala | Arg | Pro | Arg | Arg | Asp | Ala | Glu |
| | | | | 245 | | | | | 250 | | | | | 255 | |
| Pro | Val | Leu | Gly | Gly | Gly | Pro | Gly | Gly | Ala | Cys | Arg | Ala | Arg | Arg | Leu |
| | | | 260 | | | | | 265 | | | | | 270 | | |
| Tyr | Val | Ser | Phe | Arg | Glu | Val | Gly | Trp | His | Arg | Trp | Val | Ile | Ala | Pro |
| | | 275 | | | | | 280 | | | | | 285 | | | |
| Arg | Gly | Phe | Leu | Ala | Asn | Tyr | Cys | Gln | Gly | Gln | Cys | Ala | Leu | Pro | Val |
| | 290 | | | | | 295 | | | | | 300 | | | | |
| Ala | Leu | Ser | Gly | Ser | Gly | Gly | Pro | Pro | Ala | Leu | Asn | His | Ala | Val | Leu |
| 305 | | | | | 310 | | | | | 315 | | | | | 320 |
| Arg | Ala | Leu | Met | His | Ala | Ala | Ala | Pro | Gly | Ala | Ala | Asp | Leu | Pro | Cys |
| | | | | 325 | | | | | 330 | | | | | 335 | |
| Cys | Val | Pro | Ala | Arg | Leu | Ser | Pro | Ile | Ser | Val | Leu | Phe | Phe | Asp | Asn |
| | | | 340 | | | | | 345 | | | | | 350 | | |
| Ser | Asn | Asn | Val | Val | Leu | Arg | Gln | Tyr | Glu | Asp | Met | Val | Val | Asp | Glu |
| | | 355 | | | | | 360 | | | | | 365 | | | |
| Cys | Gly | Cys | Arg | | | | | | | | | | | | |
| | | 370 | | | | | | | | | | | | | |

What is claimed is:

1. A therapeutic treatment method for preventing loss of bone mass or increasing bone mass in an individual, the method comprising: systemically administering to the individual a therapeutically effective morphogen in an amount and for a time sufficient to prevent loss of or to increase bone mass in said individual, wherein the morphogen comprises an amino acid sequence selected from the group consisting of a sequence:

(a) having at least 70% homology with the C-terminal seven-cysteine skeleton of human OP-1 as set forth in residues 330–431 of SEQ ID NO: 5;

(b) having greater than 60% amino acid sequence identity with said C-terminal seven-cysteine skeleton of human OP-1; and (c) defined by OPX, SEQ ID NO: 29, wherein said morphogen stimulates endochondral bone formation in an in vivo bone assay.

2. The method of claim 1 wherein said loss of bone mass results from a metabolic bone disease.

3. The method of claim 2 wherein said metabolic bone disease comprises osteoporosis or osteomalacia.

4. The method of claim 1 wherein said loss of bone mass results from an imbalance in bone resorption or bone formation.

5. The method of claim 1 wherein said loss of bone mass results from an imbalance of calcium or phosphate metabolism.

6. The method of claim 1 wherein said loss of bone mass results from a vitamin D imbalance in the individual.

7. The method of claim 1 wherein said loss of bone mass is nutritionally or hormonally induced.

8. The method of claim 3 wherein said osteoporosis is postmenopausal or senile osteoporosis.

9. The method of claim 1 wherein said morphogen comprises an amino acid sequence sharing at least 70% homology with one of the sequences selected from the group consisting of: OP-1, OP-2, CBMP2, Vgl(fx), Vgr(fx), DPP (fx), GDF-1(fx) and 60A(fx).

10. The method of claim 1 wherein said morphogen comprises an amino acid sequence sharing at least 80% homology with one of the sequences selected from the group consisting of: OP-1, OP-2, CBMP2, Vgl(fx), Vgr(fx), DPP (fx), GDF-1(fx), and 60A(fx).

11. The method of claim 1 wherein said morphogen comprises an amino acid sequence having greater than 60% amino acid identity with the sequence defined by residues 43–139 of Seq. ID No. 5 (hOP1).

12. The method of claim 1 wherein said morphogen comprises an amino acid sequence having greater than 65% amino acid identity with the sequence defined by residues 43–139 of Seq. ID No. 5 (hOP1).

13. The method of claim 1 wherein said morphogen comprises an amino acid sequence defined by residues 43–139 of Seq. ID No. 5 (hOP1), including allelic and species variants thereof.

14. The method of claim 1 wherein said morphogen comprises an amino acid sequence defined by Generic Sequences 1, 2, 3, 4, 5 or 6 (Seq. ID Nos. 1, 2, 3, 4, 30 or 31).

15. The method of claim 1 wherein said morphogen comprises an amino acid sequence defined by OPX (Seq. ID No. 29).

16. A method for repairing defects in bone tissue microstructure, comprising: systemically administering to an individual a therapeutically effective morphogen in an amount and for a time sufficient to repair defects in said microstructure, wherein the morphogen comprises an amino acid sequence selected from the group consisting of a sequence:

(a) having at least 70% homology with the C-terminal seven-cysteine skeleton of human OP-1 as set forth in residues 330–431 of SEQ ID NO: 5;

(b) having greater than 60% amino acid sequence identity with said C-terminal seven-cysteine skeleton of human OP-1; and (c) defined by OPX, SEQ ID NO: 29, wherein said morphogen stimulates endochondral bone formation in an in vivo bone assay.

17. The method of claim 16 wherein said defect is a fracture.

18. The method of claim 16 wherein said defect results from a metabolic bone disease.

19. The method of claim 18 wherein said metabolic bone disease comprises osteoporosis or osteomalacia.

20. A method for protecting an individual at risk for loss of bone mass, the method comprising: systemically administering to the individual a therapeutically effective morphogen in an amount and for a time sufficient to protect said individual from loss of bone mass, wherein the morphogen comprises an amino acid sequence selected from the group consisting of a sequence:

(a) having at least 70% homology with the C-terminal seven-cysteine skeleton of human OP-1 as set forth in residues 330–431 of SEQ ID NO: 5;

(b) having greater than 60% amino acid sequence identity with said C-terminal seven-cysteine skeleton of human OP-1; and (c) defined by OPX, SEQ ID NO: 29, wherein said morphogen stimulates endochondral bone formation in an in vivo bone assay.

21. The method of claim 20 wherein said individual is a postmenopausal female.

22. The method of claim 20 wherein said individual is at risk for loss of bone mass as a result of senile osteoporosis.

23. The method of claim 20 wherein said individual is undergoing dialysis.

24. The method of claim 16 or 20 wherein said morphogen comprises an amino acid sequence sharing at least 70% homology with one of the sequences selected from the group consisting of: OP-1, OP-2, CBMP2, Vgl(fx), Vgr(fx), DPP (fx), GDF-1(fx) and 60A(fx).

25. The method of claim 16 or 20 wherein said morphogen comprises an amino acid sequence sharing at least 80% homology with one of the sequences selected from the group consisting of: OP-1, OP-2, CBMP2, Vgl(fx), Vgr(fx), DPP (fx), GDF-1(fx), and 60A(fx).

26. The method of claim 16 or 20 wherein said morphogen comprises an amino acid sequence having greater than 60% amino acid identity with the sequence defined by residues 43–139 of Seq. ID No. 5 (hOP1).

27. The method of claim 16 or 20 wherein said morphogen comprises an amino acid sequence having greater than 65% amino acid identity with the sequence defined by residues 43–139 of Seq. ID No. 5 (hOP1).

28. The method of claim 16 or 20 wherein said morphogen comprises an amino acid sequence defined by residues 43–139 of Seq. ID No. 5 (hOP1), including allelic and species variants thereof.

29. The method of claim 16 or 20 wherein said morphogen comprises an amino acid sequence defined by Generic Sequences 1, 2, 3, 4, 5 or 6 (Seq. ID Nos. 1, 2, 3, 4, 30 or 31).

30. The method of claim 16 or 20 wherein said morphogen comprises an amino acid sequence defined by OPX (Seq. ID No. 29).

31. The method of claim 1, 16 or 20, wherein said morphogen or said morphogen-stimulating agent is provided to the individual by oral administration.

32. The method of claim 1, 16 or 20, wherein said morphogen or morphogen-stimulating agent is provided to the individual by parenteral administration.

33. The method of claim 1 or 20 wherein said morphogen is provided to said individual in association with a molecule capable of enhancing the solubility of said morphogen.

34. The method of claim 33 wherein said molecule comprises casein or part or all of the pro domain of a morphogen.

35. The method of claim 34 wherein said pro domain comprises part or all of the sequence described by residues 30 to 292 of Seq. ID No. 16.

36. The method of claim 1, 16, or 20 wherein said morphogen is provide to the individual in association with a molecule capable of targeting said morphogen to bone tissue.

37. The method of claim 36 wherein said targeting molecule comprises tetracycline, diphosphonates, or an antibody that binds specifically to a molecule on the surface of bone tissue cells.

38. The method of claim 1 or 20 wherein the morphogen is administered parenterally.

39. The method of claim 1 or 20 wherein the morphogen is administered orally.

40. The method of claim 1 or 20 further comprising administering vitamin D3, calcitonin, prostaglandins, parathyroid hormone, dexamethasone, estrogen or insulin-like growth factor (IGF) to the subject.

* * * * *

UNITED STATES PATENT AND TRADEMARK OFFICE
CERTIFICATE OF CORRECTION

PATENT NO. : 7,056,882 B2
APPLICATION NO. : 09/952318
DATED : June 6, 2006
INVENTOR(S) : Cohen et al.

It is certified that error appears in the above-identified patent and that said Letters Patent is hereby corrected as shown below:

Col. 120, line 67, change "330-431" to --38-139-- ;

Col. 121, line 61, change "330-431" to --38-139--;

Col. 122, line 15, change "330-431" to --38-139--.

Signed and Sealed this

Fifteenth Day of August, 2006

JON W. DUDAS
*Director of the United States Patent and Trademark Office*